US012344839B2

(12) United States Patent
Khvorova et al.

(10) Patent No.: US 12,344,839 B2
(45) Date of Patent: Jul. 1, 2025

(54) DUAL-ACTING siRNA BASED MODULATION OF C9orf72

(71) Applicant: UNIVERSITY OF MASSACHUSETTS, Boston, MA (US)

(72) Inventors: Anastasia Khvorova, Westborough, MA (US); Bruno Miguel da Cruz Godinho, Worcester, MA (US); James W. Gilbert, Worcester, MA (US)

(73) Assignee: UNIVERSITY OF MASSACHUSETTS, Westborough, MA (US)

(*) Notice: Subject to any disclaimer, the term of this patent is extended or adjusted under 35 U.S.C. 154(b) by 354 days.

(21) Appl. No.: 17/213,887

(22) Filed: Mar. 26, 2021

(65) Prior Publication Data
US 2021/0340535 A1 Nov. 4, 2021

Related U.S. Application Data

(60) Provisional application No. 63/000,899, filed on Mar. 27, 2020.

(51) Int. Cl.
*C12N 15/113* (2010.01)
*C12Q 1/68* (2018.01)

(52) U.S. Cl.
CPC ........ *C12N 15/113* (2013.01); *C12N 2310/11* (2013.01); *C12N 2310/314* (2013.01); *C12N 2310/315* (2013.01); *C12N 2310/321* (2013.01); *C12N 2310/322* (2013.01); *C12N 2310/3233* (2013.01); *C12N 2310/332* (2013.01); *C12N 2310/351* (2013.01); *C12N 2320/30* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,328,470 A | 7/1994 | Nabel et al. |
| 5,684,143 A | 11/1997 | Gryaznov et al. |
| 5,814,014 A | 9/1998 | Elsberry et al. |
| 5,858,988 A | 1/1999 | Wang |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 7,459,547 B2 | 12/2008 | Zamore et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 2005/0220766 A1 | 10/2005 | Amalfitano et al. |
| 2006/0078542 A1 | 4/2006 | Mah et al. |
| 2007/0259827 A1 | 11/2007 | Aronin et al. |
| 2008/0269149 A1 | 10/2008 | Bowles et al. |
| 2010/0186103 A1 | 7/2010 | Gao et al. |
| 2014/0296486 A1 | 10/2014 | Gao et al. |
| 2015/0259679 A1 | 9/2015 | Bennett et al. |
| 2016/0251655 A1* | 9/2016 | Freier ............... A61P 25/16 514/44 A |
| 2016/0319278 A1* | 11/2016 | Khvorova ............ A61P 43/00 |
| 2017/0233735 A1 | 8/2017 | Corey et al. |
| 2017/0312367 A1 | 11/2017 | Khvorova et al. |
| 2020/0385737 A1 | 12/2020 | Khvorova et al. |
| 2023/0114649 A1* | 4/2023 | Fishilevich .......... C12N 15/113 514/44 A |

FOREIGN PATENT DOCUMENTS

| | | |
|---|---|---|
| CA | 3164599 A1 | 6/2021 |
| WO | WO 2003/029459 A2 | 4/2003 |
| WO | WO 2015/054676 A2 | 4/2015 |
| WO | WO 2016/112132 A1 | 7/2016 |
| WO | WO 2017/109757 A1 | 6/2017 |
| WO | WO 2021/119226 A1 | 6/2021 |

OTHER PUBLICATIONS

Alisky et al., "Gene therapy for amyotrophic lateral sclerosis and other motor neuron diseases", Hum Gene Ther., 11(17):2315-2329, doi: 10.1089/104303400750038435, (Nov. 20, 2000).
Altschul, et al., "Basic local alignment search tool", J Mol Biol., 215(3):403-10, doi: 10.1016/S0022-2836(05)80360-2, (Oct. 5, 1990).
Altschul, et al., "Gapped BLAST and PSI-BLAST: A New Generation Of Protein Database Search Programs", Nucleic Acids Research, vol. 25, No. 17, pp. 3389-3402, 1997.
Alvarez-Erviti et al., "Delivery of siRNA to the mouse brain by systemic injection of targeted exosomes", Nat Biotechnol., 29(4):341-345, doi: 10.1038/nbt.1807, (Apr. 2011).
Ambros et al., "MicroRNAs and other tiny endogenous RNAs in C. elegans", Curr Biol, 13, 807-18, doi:10.1016/S0960-9822(03)00287-2, (2003).
Atwell et al., "Stable heterodimers from remodeling the domain interface of a homodimer using a phage display library", J Mol Biol., 270(1):26-35, doi: 10.1006/jmbi.1997.1116, (Jul. 4, 1997).
Ausubel et al., "Short Protocols In Molecular Biology", 4th Ed. John Wiley & Sons, NY, ISBN 0-471-32938-X, (1999).

(Continued)

*Primary Examiner* — Sean McGarry
(74) *Attorney, Agent, or Firm* — LATHROP GPM LLP; James H. Velema, Esq.; Michael J. Spellberg, Esq.

(57) ABSTRACT

This disclosure relates to novel C9ORF72 targeting sequences. Novel sense and antisense dual-targeting oligonucleotides for the treatment of neurodegenerative diseases are also provided.

32 Claims, 31 Drawing Sheets
Specification includes a Sequence Listing.

(56) References Cited

OTHER PUBLICATIONS

Billy et al., "Specific interference with gene expression induced by long, double-stranded RNA in mouse embryonal teratocarcinoma cell lines", Proc Natl Acad Sci USA, 98(25): 14428-14233, doi: 10.1073/pnas.261562698. (Dec. 4, 2001).
Braasch et al., "RNA Interference in Mammalian Cells by Chemically-Modified RNA", Biochemistry, 42:7967-7975, (2003).
Brummelkamp et al., "A System for Stable Expression of Short Interfering RNAs in Mammalian Cells", Science, 296, 550-553, (2002).
Carter et al., "Handbook of Parvoviruses", ed., p. Tijsser, CRC Press, 1990, pp. 155-168.
Chen et al., "Gene therapy for brain tumors: Regression of experimental gliomas by adenovirus-mediated gene transfer in vivo", Proc. Natl. Acad. Sci. USA, 91, 3054-3057, (1994).
Davidson et al., "A model system for in vivo gene transfer into the central nervous system using an adenoviral vector", Nat Genet., 3(3):219-23, doi: 10.1038/ng0393-219, (Mar. 1993).
Davidson et al., "Recombinant adeno-associated virus type 2, 4, and 5 vectors: Transduction of variant cell types and regions in the mammalian central nervous system", PNAS, 97(7):3428-3432, doi.org/10.1073/pnas.97.7.3428, (Mar. 28, 2000).
Doench et al., "siRNAs can function as miRNAs", Genes Dev., 17(4):438-42, doi: 10.1101/gad.1064703, (Feb. 15, 2003).
Eckstein, "Phosphorothioate oligodeoxynucleotides: what is their origin and what is unique about them?", Antisense Nucleic Acid Drug Dev., 10(2):117-121, (Apr. 2000).
Egusquiaguirre et al., "Nanoparticle delivery systems for cancer therapy: advances in clinical and preclinical research", Clin Transl Oncol., 14(2):83-93, doi: 10.1007/s12094-012-0766-6, (Feb. 2012).
El Andaloussi et al., "Exosomes for targeted siRNA delivery across biological barriers", Adv Drug Deliv Rev., 65(3):391-397, doi: 10.1016/j.addr.2012.08.008, (Mar. 2013).
El Andaloussi et al., "Extracellular vesicles: biology and emerging therapeutic opportunities", Nat Rev Drug Discov., 12(5):347-357, doi: 10.1038/nrd3978, (May 2013).
El-Andaloussi et al., "Exosome-mediated delivery of siRNA in vitro and in vivo", Nat Protoc., 7(12):2112-2126, doi: 10.1038/nprot.2012.131, (2012).
Elmen et al., "Locked nucleic acid (LNA) mediated improvements in siRNA stability and functionality", Nucleic Acids Res., 33(1):439-447, doi: 10.1093/nar/gki193, (Jan. 14, 2005).
Fattal et al., "Biodegradable polyalkylcyanoacrylate nanoparticles for the delivery of oligonucleotides", J Control Release, 53(1-3):137-43, doi: 10.1016/s0168-3659(97)00246-0, (Apr. 30, 1998).
Fisher et al., "Transduction with Recombinant Adeno-Associated Virus for Gene Therapy Is Limited by Leading-Strand Synthesis", J Virol., 70:520 532, (Jan. 1996).
Godard et al., "Antisense effects of cholesterol-oligodeoxynucleotide conjugates associated with poly(alkylcyanoacrylate) nanoparticles", Eur J Biochem., 232(2):404-410, (Sep. 1, 1995).
Goodson, in Medical Applications of Controlled Release, vol. 2, pp. 115-138, (1984).
Grad et al., "Computational and experimental identification of C. elegans microRNAs", Mol Cell., May 2003, 11(5):1253-1263, doi: 10.1016/s1097-2765(03)00153-9.
Griffiths-Jones, "The microRNA Registry", Nucleic Acids Res., 32(Database issue): D109-D111, doi: 10.1093/nar/gkh023, (Jan. 1, 2004).
Haeusler et al., "The expanding biology of the C9orf72 nucleotide repeat expansion in neurodegenerative disease", Nature Reviews Neuroscience, vol. 17, pp. 383-395 (2016).
Hamajima et al., "Intranasal administration of HIV-DNA vaccine formulated with a polymer, carboxymethylcellulose, augments mucosal antibody production and cell-mediated immune response", Clin Immunol Immunopathol., 88(2):205-210, doi: 10.1006/clin.1998.4566, (Aug. 1998).
Hutvagner et al., "A microRNA in a multiple-turnover RNAi enzyme complex", Science, 297(5589):2056-2060, doi: 10.1126/science.1073827, (Aug. 1, 2002).

International Search Report and Written Opinion of PCT/US2021/024379, mailed Jul. 13, 2021.
Karlin et al., "Applications and Statistics For Multiple High-Scoring Segments In Molecular Sequences", Proceedings of the National Academy of Sciences of the USA, vol. 90, pp. 5873-5877, Jun. 1, 1993.
Karlin et al., "Methods for assessing the statistical significance of molecular sequence features by using general scoring schemes", Proc. Natl. Acad. Sci. USA, 87:2264-2268, (Mar. 1990).
Kontermann et al., "Antibody Engineering Springer-Verlag", New York, 790, pp. ISBN 3-540-41354-5, (2001).
Lagos-Quintana et al., "Identification of novel genes coding for small expressed RNAs", Science, 294(5543):853-858, doi: 10.1126/science.1064921, (Oct. 26, 2001).
Lagos-Quintana et al., "Identification of tissue-specific microRNAs from mouse", Curr Biol., 12(9):735-739, doi: 10.1016/s0960-9822(02)00809-6, (Apr. 30, 2002).
Lai et al., "Computational identification of DrosophilamicroRNA genes", Genome Biol., 2003, 4(7):R42. doi: 10.1186/GB-2003-4-7-r42. (Jun. 30, 2003).
Lam, et al., "A New Type of Synthetic Peptide Library For Identifying Ligand-Binding Activity", Nature, vol. 354, pp. 82-84, Nov. 7, 1991.
Lambert et al., "Nanoparticulate systems for the delivery of antisense oligonucleotides", Adv Drug Deliv Rev., 47(1):99-112, doi: 10.1016/s0169-409x(00)00116-2, (Mar. 23, 2001).
Lau et al., "An abundant class of tiny RNAs with probable regulatory roles in Caenorhabditis elegans", Science, 294(5543):858-862, doi: 10.1126/science.1065062, (Oct. 26, 2001).
Lee et al., "An extensive class of small RNAs in Caenorhabditis elegans", Science, 294(5543):862-864, doi: 10.1126/science.1065329, (Oct. 26, 2001).
Lee et al., "Recent Developments in Nanoparticle-Based siRNA Delivery for Cancer Therapy", BioMed Research International, vol. Article ID 782041, 10 pages, doi:10.1155/2013/782041, (2013).
Lim et al., "The microRNAs of Caenorhabditis elegans", Genes Dev., Apr. 15, 2003, 17(8):991-1008, doi: 10.1101/gad.1074403.
Lim et al., "Vertebrate microRNA genes", Science, 299(5612): 1540, doi: 10.1126/science.1080372, (Mar. 7, 2003).
McCaffrey et al., "Gene Expression: RNA interference in adult mice", Nature, 418(6893):38-39, doi: 10.1038/418038a, (Jul. 4, 2002).
Miyagishi et al., "U6 promoter-driven siRNAs with four uridine 3' overhangs efficiently suppress targeted gene expression in mammalian cells", Nat Biotechnol., 20(5):497-500, doi: 10.1038/nbt0502-497, (May 2002).
Mourelatos et al., "miRNPs: a novel class of ribonucleoproteins containing numerous microRNAs", Genes Dev., 16(6): 720-728, (Mar. 15, 2002).
Nielsen, et al., "Sequence-selective recognition of DNA by strand displacement with a thymine-substituted polyamide", Science;254(5037): 1497-1500, doi: 10.1126/science.1962210, (Dec. 6, 1991).
O'Rourke et al., "C9orf72 BAC Transgenic Mice Display Typical Pathologic Features of ALS/FTD", Neuron, vol. 88, No. 5, pp. 892-901, Dec. 2, 2015.
Petersen et al., "LNA: a versatile tool for therapeutics and genomics", Trends Biotechnol., 21(2):74-81, doi: 10.1016/S0167-7799(02)00038-0, (Feb. 2003).
Putnam, "Antisense strategies and therapeutic applications", Am. J. Health Syst. Pharm., 53(2), 151-160, (1996).
Reinhart et al., "Small RNAs correspond to centromere heterochromatic repeats", Science, 297(5588):1831, doi: 10.1126/science.1077183, (Aug. 22, 2002).
Rusckowski et al., "Biodistribution and metabolism of a mixed backbone oligonucleotide (GEM 231) following single and multiple dose administration in mice", Antisense Nucleic Acid Drug Dev., 10(5):333-345, doi: 10.1089/oli.1.2000.10.333, (Oct. 2000).
Sambrook, et al., "Molecular Cloning: A Laboratory Manual", Chapters 9 and 11, Cold Spring Harbor Laboratory Press, Cold Spring Harbor, 1989.

(56) References Cited

OTHER PUBLICATIONS

Schwab et al., "An approach for new anticancer drugs: oncogene-targeted antisense DNA", Ann Oncol., 5 Suppl 4:55-58, doi: 10.1093/annonc/5.suppl_4.s55, (1994).
Stein et al., "Systemic and Central Nervous System Correction of Lysosomal Storage in Mucopolysaccharidosis Type VII Mice", J Virol, 73:3424-3429, (1999).
Stein, "Inhibition of Vesivirus infections in mammalian tissue culture with antisense morpholino oligomers", Antisense Nucleic Acid Drug Dev., 11(5):317-325, doi: 10.1089/108729001753231696, (Oct. 2001).
Vorobjev et al. "Nuclease resistance and RNase H sensitivity of oligonucleotides bridged by oligomethylenediol and oligoethylene glycol linkers", Antisense Nucleic Acid Drug Dev., 11(2):77-85, doi: 10.1089/108729001750171290, (Apr. 2001).
Wang et al., "Nanoparticle-based delivery system for application of siRNA in vivo", Curr Drug Metab., 11(2):182-196, doi: 10.2174/138920010791110863, (Feb. 2010).
Wright et al., "Identification of Factors that Contribute to Recombinant AAV2 Particle Aggregation and Methods to Prevent Its Occurrence during Vector Purification and Formulation", Molecular Therapy, 12:171-178, (2005).
Xia et al., "siRNA-mediated gene silencing in vitro and in vivo", Nat Biotechnol., 20(10):1006-1010, doi: 10.1038/nbt739, (Sep. 16, 2002).
Yekta et al., "MicroRNA-directed cleavage of HOXB8 mRNA", Science, 304(5670):594-596, doi: 10.1126/science.1097434, (Apr. 23, 2004).
Yuan et al, "Recent advances of siRNA delivery by nanoparticles", Expert Opinion on Drug Delivery, vol. 8, No. 4, pp. 521-536, (2011).
Zeng et al., "Both natural and designed micro RNAs can inhibit the expression of cognate mRNAs when expressed in human cells", Mol. Cell, 9(6):1327-1333, doi: 10.1016/s1097-2765(02)00541-5, (Jun. 2002).
Zeng et al., "Sequence requirements for micro RNA processing and function in human cells", RNA, 9(1):112-123, doi: 10.1261/rna.2780503, (Jan. 2003).
Zhang et al., "Several rAAV vectors efficiently cross the blood-brain barrier and transduce neurons and astrocytes in the neonatal mouse central nervous system", Mol. Ther., 19(8):1440-1448, doi: 10.1038/mt.2011.98, (May 24, 2011).
Aviñó et al. "Branched RNA: A New Architecture for RNA Interference", Journal of Nucleic Acids, Mar. 6, 2010, 2011: 1-7. doi: 10.4061/2011/568935.
Extended European Search Report for European Patent Application No. 21775632.3, dated May 8, 2025.
Hu et al., "Engineering Duplex RNAs for Challenging Targets: Recognition of GGGGCC/CCCCGG Repeats at the ALS/FTD C9orf72 Locus", Chemistry & Biology, Nov. 12, 2015, 22(11): 1505-1511.
Vickers et al., "Efficient reduction of target RNAs by small interfering RNA and RNase H-dependent antisense agents. A comparative analysis", Journal of Biological Chemistry, Feb. 28, 2003, 278(9): 7108-7118. doi: 10.1074/jbc.M210326200. Epub Dec. 23, 2002.

\* cited by examiner

Non-selective targeting: siRNA targeting region from 6686-7110 of exon 2

Selective targeting: siRNA targeting regions consisting of exon 1a and intron1 prior to $G_4C_2$ repeat, from positions 18 to 306

Pathological (Sense)

Pathological (Antisense)

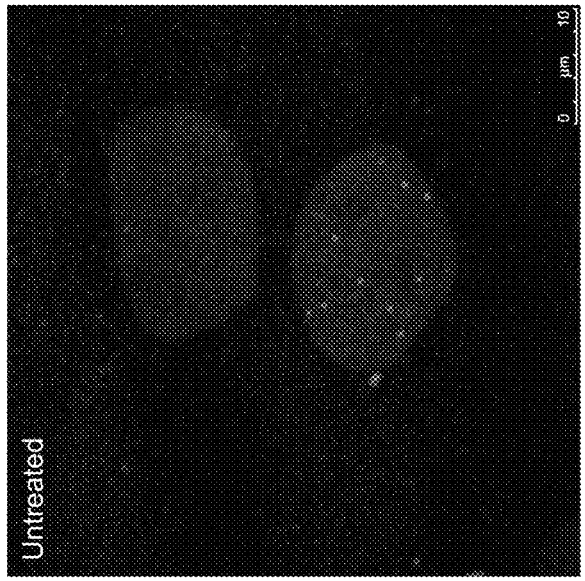
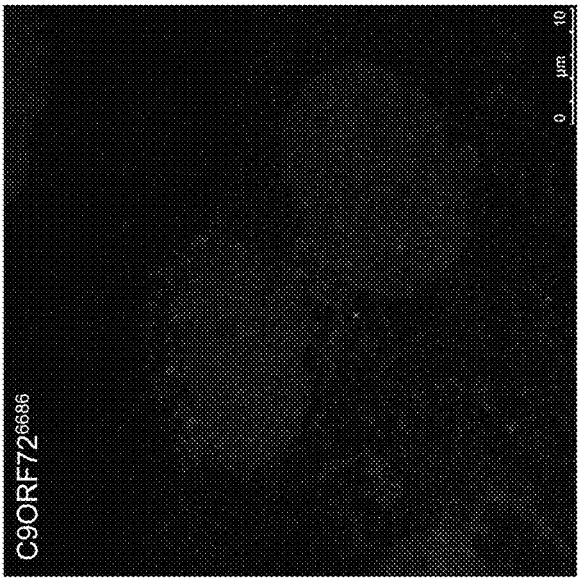
Fig. 13A
Fig. 13B

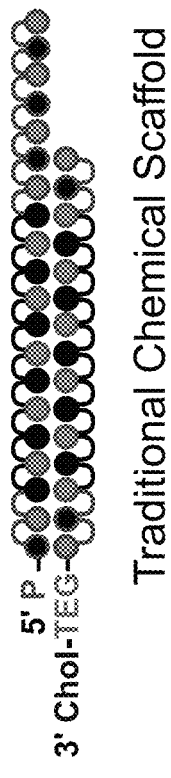
Fig. 24A   Traditional Chemical Scaffold
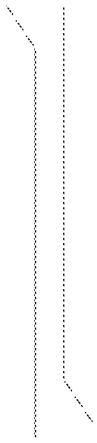
Fig. 24B   Proposed Dual Acting Chemical Scaffold

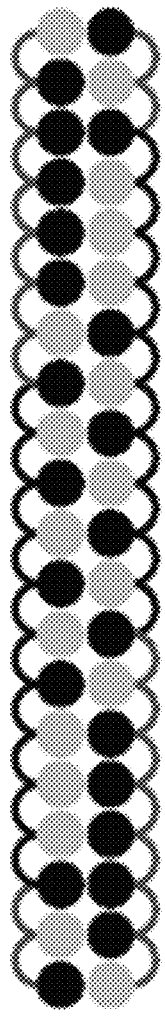
Fig. 27A
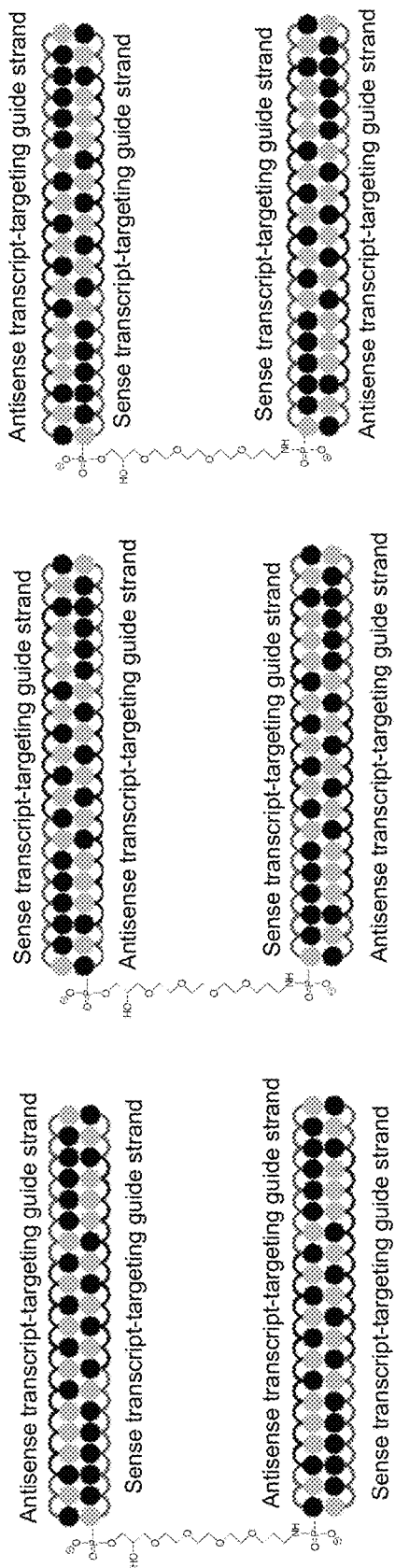
Fig. 27B
Fig. 27C
Fig. 27D

SEQUENCE LISTING

<160> NUMBER OF SEQ ID NOS: 432

<210> SEQ ID NO 1
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
acaagaaaag accugauaaa gauuaaccag aagaaaacaa ggagg            45

<210> SEQ ID NO 2
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agaaaagacc ugauaaagau uaaccagaag aaaacaagga gggaa            45

<210> SEQ ID NO 3
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ucccuccuug uuucuucug guuaaucuuu aucaggucuu uucuu            45

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aagauuaacc agaagaaaac            20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5 guuucuucu gguuaaucua            20

<210> SEQ ID NO 6
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucccuccugu uuucuucugg uuaaucuuua ucaggucuuu ucuu            44

<210> SEQ ID NO 7
<211> LENGTH: 45
<212> TYPE: DNA
<213> ORGANISM: Homo sapiens

<400> SEQUENCE: 7
acaagaaaag acctgataaa gattaaccag aagaaaacaa ggagg            45

<210> SEQ ID NO 8
<211> LENGTH: 45
<212> TYPE: DNA
<213> ORGANISM: Homo sapiens

<400> SEQUENCE: 8
tccctccttg ttttcttctg gttaatcttt atcaggtctt ttctt            45

<210> SEQ ID NO 9
<211> LENGTH: 45
<212> TYPE: DNA
<213> ORGANISM: Homo sapiens

<400> SEQUENCE: 9
gtaacctacg gtgtcccgct aggaaagaga ggtgcgtcaa acagc            45

<210> SEQ ID NO 10
<211> LENGTH: 45
<212> TYPE: DNA
<213> ORGANISM: Homo sapiens

<400> SEQUENCE: 10
gtgtcccgct aggaaagaga ggtgcgtcaa acagcgacaa gttcc            45

<210> SEQ ID NO 11
<211> LENGTH: 45
<212> TYPE: DNA
<213> ORGANISM: Homo sapiens

<400> SEQUENCE: 11
tcccgctagg aaagagaggt gcgtcaaaca gcgacaagtt ccgcc            45

<210> SEQ ID NO 12
<211> LENGTH: 45
<212> TYPE: DNA
<213> ORGANISM: Homo sapiens

<400> SEQUENCE: 12
gctaggaaag agaggtgcgt caaacagcga caagttccgc ccacg            45

<210> SEQ ID NO 13
<211> LENGTH: 45
<212> TYPE: DNA
<213> ORGANISM: Homo sapiens

<400> SEQUENCE: 13
ggtgcgtcaa acagcgacaa gttccgccca cgtaaaagat gacgc            45

<210> SEQ ID NO 14
<211> LENGTH: 45
<212> TYPE: DNA
<213> ORGANISM: Homo sapiens

<400> SEQUENCE: 14

```
cgtcaaacag cgacaagttc cgcccacgta aaagatgacg cttgg              45
```

\<210\> SEQ ID NO 15
\<211\> LENGTH: 45
\<212\> TYPE: DNA
\<213\> ORGANISM: Homo sapiens

\<400\> SEQUENCE: 15

```
aaacagcgac aagttccgcc cacgtaaaag atgacgcttg gtgtg              45
```

\<210\> SEQ ID NO 16
\<211\> LENGTH: 45
\<212\> TYPE: DNA
\<213\> ORGANISM: Homo sapiens

\<400\> SEQUENCE: 16

```
tctcttttgg gggcggggtc tagcaagagc aggtgtgggt ttagg              45
```

\<210\> SEQ ID NO 17
\<211\> LENGTH: 45
\<212\> TYPE: DNA
\<213\> ORGANISM: Homo sapiens

\<400\> SEQUENCE: 17

```
tcttttgggg gcggggtcta gcaagagcag gtgtgggttt aggag              45
```

\<210\> SEQ ID NO 18
\<211\> LENGTH: 45
\<212\> TYPE: DNA
\<213\> ORGANISM: Homo sapiens

\<400\> SEQUENCE: 18

```
ggggcggggt ctagcaagag caggtgtggg tttaggaggt gtgtg              45
```

\<210\> SEQ ID NO 19
\<211\> LENGTH: 45
\<212\> TYPE: DNA
\<213\> ORGANISM: Homo sapiens

\<400\> SEQUENCE: 19

```
ggtctagcaa gagcaggtgt gggtttagga ggtgtgtgtt tttgt              45
```

\<210\> SEQ ID NO 20
\<211\> LENGTH: 45
\<212\> TYPE: DNA
\<213\> ORGANISM: Homo sapiens

\<400\> SEQUENCE: 20

```
agcaagagca ggtgtgggtt taggaggtgt gtgttttttgt ttttc             45
```

\<210\> SEQ ID NO 21
\<211\> LENGTH: 45
\<212\> TYPE: DNA
\<213\> ORGANISM: Homo sapiens

\<400\> SEQUENCE: 21

```
gcaagagcag gtgtgggttt aggaggtgtg tgttttttgtt tttcc             45
```

\<210\> SEQ ID NO 22
\<211\> LENGTH: 45
\<212\> TYPE: DNA
\<213\> ORGANISM: Homo sapiens

\<400\> SEQUENCE: 22 caagagcagg tgtgggttta ggaggtgtgt gtttttgttt ttccc    45

<210> SEQ ID NO 23
<211> LENGTH: 45
<212> TYPE: DNA
<213> ORGANISM: Homo sapiens

<400> SEQUENCE: 23
gtttttgttt tcccaccct ctctccccac tacttgctct cacag    45

<210> SEQ ID NO 24
<211> LENGTH: 45
<212> TYPE: DNA
<213> ORGANISM: Homo sapiens

<400> SEQUENCE: 24
ttttgttttt cccaccctct ctccccacta cttgctctca cagta    45

<210> SEQ ID NO 25
<211> LENGTH: 45
<212> TYPE: DNA
<213> ORGANISM: Homo sapiens

<400> SEQUENCE: 25
tttttcccac cctctctccc cactacttgc tctcacagta ctcgc    45

<210> SEQ ID NO 26
<211> LENGTH: 45
<212> TYPE: DNA
<213> ORGANISM: Homo sapiens

<400> SEQUENCE: 26
tcccaccctc tctccccact acttgctctc acagtactcg ctgag    45

<210> SEQ ID NO 27
<211> LENGTH: 45
<212> TYPE: DNA
<213> ORGANISM: Homo sapiens

<400> SEQUENCE: 27
ctccccacta cttgctctca cagtactcgc tgagggtgaa caaga    45

<210> SEQ ID NO 28
<211> LENGTH: 45
<212> TYPE: DNA
<213> ORGANISM: Homo sapiens

<400> SEQUENCE: 28
acttgctctc acagtactcg ctgagggtga acaagaaaag acctg    45

<210> SEQ ID NO 29
<211> LENGTH: 45
<212> TYPE: DNA
<213> ORGANISM: Homo sapiens

<400> SEQUENCE: 29
tgctctcaca gtactcgctg agggtgaaca agaaaagacc tgata    45

<210> SEQ ID NO 30
<211> LENGTH: 45
<212> TYPE: DNA
<213> ORGANISM: Homo sapiens

```
<400> SEQUENCE: 30
gctctcacag tactcgctga gggtgaacaa gaaaagacct gataa          45

<210> SEQ ID NO 31
<211> LENGTH: 45
<212> TYPE: DNA
<213> ORGANISM: Homo sapiens

<400> SEQUENCE: 31
tcacagtact cgctgagggt gaacaagaaa agacctgata aagat          45

<210> SEQ ID NO 32
<211> LENGTH: 45
<212> TYPE: DNA
<213> ORGANISM: Homo sapiens

<400> SEQUENCE: 32
actcgctgag ggtgaacaag aaaagacctg ataaagatta accag          45

<210> SEQ ID NO 33
<211> LENGTH: 45
<212> TYPE: DNA
<213> ORGANISM: Homo sapiens

<400> SEQUENCE: 33
gtgaacaaga aaagacctga taaagattaa ccagaagaaa acaag          45

<210> SEQ ID NO 34
<211> LENGTH: 45
<212> TYPE: DNA
<213> ORGANISM: Homo sapiens

<400> SEQUENCE: 34
aagaaaagac ctgataaaga ttaaccagaa gaaaacaagg aggga          45

<210> SEQ ID NO 35
<211> LENGTH: 45
<212> TYPE: DNA
<213> ORGANISM: Homo sapiens

<400> SEQUENCE: 35
agaaaagacc tgataaagat taaccagaag aaaacaagga gggaa          45

<210> SEQ ID NO 36
<211> LENGTH: 45
<212> TYPE: DNA
<213> ORGANISM: Homo sapiens

<400> SEQUENCE: 36
gacctgataa agattaacca gaagaaaaca aggagggaaa caacc          45

<210> SEQ ID NO 37
<211> LENGTH: 45
<212> TYPE: DNA
<213> ORGANISM: Homo sapiens

<400> SEQUENCE: 37
acctgataaa gattaaccag aagaaaacaa ggagggaaac aaccg          45

<210> SEQ ID NO 38
<211> LENGTH: 45
<212> TYPE: DNA
<213> ORGANISM: Homo sapiens
```

```
<400> SEQUENCE: 38
agaaaacaag gagggaaaca accgcagcct gtagcaagct ctgga            45

<210> SEQ ID NO 39
<211> LENGTH: 45
<212> TYPE: DNA
<213> ORGANISM: Homo sapiens

<400> SEQUENCE: 39
aaacaaggag ggaaacaacc gcagcctgta gcaagctctg gaact            45

<210> SEQ ID NO 40
<211> LENGTH: 45
<212> TYPE: DNA
<213> ORGANISM: Homo sapiens

<400> SEQUENCE: 40
gagggaaaca accgcagcct gtagcaagct ctggaactca ggagt            45

<210> SEQ ID NO 41
<211> LENGTH: 45
<212> TYPE: DNA
<213> ORGANISM: Homo sapiens

<400> SEQUENCE: 41
aacaaccgca gcctgtagca agctctggaa ctcaggagtc gcgcg            45

<210> SEQ ID NO 42
<211> LENGTH: 45
<212> TYPE: DNA
<213> ORGANISM: Homo sapiens

<400> SEQUENCE: 42
aaccgcagcc tgtagcaagc tctggaactc aggagtcgcg cgcta            45

<210> SEQ ID NO 43
<211> LENGTH: 45
<212> TYPE: DNA
<213> ORGANISM: Homo sapiens

<400> SEQUENCE: 43
cgcagcctgt agcaagctct ggaactcagg agtcgcgcgc taggg            45

<210> SEQ ID NO 44
<211> LENGTH: 45
<212> TYPE: DNA
<213> ORGANISM: Homo sapiens

<400> SEQUENCE: 44
gcaagctctg gaactcagga gtcgcgcgct aggggccggg gccgg            45

<210> SEQ ID NO 45
<211> LENGTH: 45
<212> TYPE: DNA
<213> ORGANISM: Homo sapiens

<400> SEQUENCE: 45
caagctctgg aactcaggag tcgcgcgcta ggggccgggg ccggg            45

<210> SEQ ID NO 46
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 46
ccgcuaggaa agagaggugc                                                     20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
agagaggugc gucaaacagc                                                     20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
gaggugcguc aaacagcgac                                                     20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugcgucaaac agcgacaagu                                                     20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gacaaguucc gcccacguaa                                                     20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
aguuccgccc acguaaaaga                                                     20

<210> SEQ ID NO 52
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 52
ccgcccacgu aaaagaugac                                                      20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
gggucuagca agagcaggug                                                      20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
gucuagcaag agcaggugug                                                      20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
aagagcaggu gugguuuag                                                       20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gguguggguu uaggaggugu                                                      20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ggguuuagga ggugugguu                                                       20

<210> SEQ ID NO 58
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 58
gguuuaggag gugugueuuu                                                 20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
guuuaggagg uguguguuuu                                                 20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
acccucucuc cccacuacuu                                                 20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ccucucuccc cacuacuugc                                                 20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
cuccccacua cuugcucuca                                                 20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ccacuacuug cucucacagu                                                 20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
ucucacagua cucgcugagg                                               20

<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
acucgcugag ggugaacaag                                               20

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cgcugagggu gaacaagaaa                                               20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gcugagggug aacaagaaaa                                               20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
agggugaaca agaaaagacc                                               20

<210> SEQ ID NO 69
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
acaagaaaag accugauaaa                                               20

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 70
ccugauaaag auuaaccaga                                          20

<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
aaccagaaga aacaaggag                                           20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
accagaagaa aacaaggagg                                          20

<210> SEQ ID NO 73
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaacaaccgc agccuguagc                                          20

<210> SEQ ID NO 74
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
caaccgcagc cuguagcaag                                          20

<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
agccuguagc aagcucugga                                          20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 76
uagcaagcuc uggaacucag                                            20

<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
caagcucugg aacucaggag                                            20

<210> SEQ ID NO 78
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gcucuggaac ucaggagucg                                            20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
caggagucgc gcgcuagggg                                            20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
aggagucgcg cgcuaggggc                                            20

<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
ucaccucucu uuccuagcgg                                            20

<210> SEQ ID NO 82
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
```
ucuguuugac gcaccucucu                                          20

<210> SEQ ID NO 83
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uucgcuguuu gacgcaccuc                                          20

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ucuugucgcu guuugacgca                                          20

<210> SEQ ID NO 85
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uuacgugggc ggaacuuguc                                          20

<210> SEQ ID NO 86
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
ucuuuuacgu gggcggaacu                                          20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
uucaucuuuu acgugggcgg                                          20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uaccugcucu ugcuagaccc                                          20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
uacaccugcu cuugcuagac                                          20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uuaaacccac accugcucuu                                          20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
ucaccuccua aacccacacc                                          20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uacacacacc uccuaaaccc                                          20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uaacacacac cuccuaaacc                                          20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
uaaacacaca ccuccuaaac                                          20

<210> SEQ ID NO 95
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95 uaguagugggg gagagagggu                                              20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucaaguagug gggagagagg                                               20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ugagagcaag uagugggggag                                              20

<210> SEQ ID NO 98
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucugugagag caaguagugg                                               20

<210> SEQ ID NO 99
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ucucagcgag uacugugaga                                               20

<210> SEQ ID NO 100
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uuuguucacc cucagcgagu                                               20

```
<210> SEQ ID NO 101
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uuucuuguuc acccucagcg                                                    20

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
uuuucuuguu cacccucagc                                                    20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ugucuuuucu uguucacccu                                                    20

<210> SEQ ID NO 104
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uuuaucaggu cuuuucuugu                                                    20

<210> SEQ ID NO 105
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucugguuaau cuuuaucagg                                                    20

<210> SEQ ID NO 106
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
uuuuucuucu gguuaaucuu                                                    20
```

```
<210> SEQ ID NO 107
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
uuccuuguuu ucuucugguu                                                    20

<210> SEQ ID NO 108
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ucuccuuguu uucuucuggu                                                    20

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ucuacaggcu gcgguuguuu                                                    20

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
uuugcuacag gcugcgguug                                                    20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
uccagagcuu gcuacaggcu                                                    20

<210> SEQ ID NO 112
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
uugaguucca gagcuugcua                                                    20

<210> SEQ ID NO 113
```

-continued

<210> SEQ ID NO 113
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuccugaguu ccagagcuug                                              20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
ugacuccuga guuccagagc                                              20

<210> SEQ ID NO 115
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
ucccuagcgc gcgacuccug                                              20

<210> SEQ ID NO 116
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
uccccuagcg cgcgacuccu                                              20

<210> SEQ ID NO 117
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ucaccucucu uuccuagcgg                                              20

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
ucuguuugac gcaccucucu                                              20

<210> SEQ ID NO 119
<211> LENGTH: 20

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
uucgcuguuu gacgcaccuc                                                     20

<210> SEQ ID NO 120
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ucuugucgcu guuugacgca                                                     20

<210> SEQ ID NO 121
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
uuacgugggc ggaacuuguc                                                     20

<210> SEQ ID NO 122
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
ucuuuuacgu gggcggaacu                                                     20

<210> SEQ ID NO 123
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
uucaucuuuu acgugggcgg                                                     20

<210> SEQ ID NO 124
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
uaccugcucu ugcuagaccc                                                     20

<210> SEQ ID NO 125
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 125
uacaccugcu cuugcuagac                                                  20

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uuaaacccac accugcucuu                                                  20

<210> SEQ ID NO 127
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ucaccuccua aacccacacc                                                  20

<210> SEQ ID NO 128
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
uacacacacc uccuaaaccc                                                  20

<210> SEQ ID NO 129
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uaacacacac cuccuaaacc                                                  20

<210> SEQ ID NO 130
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
uaaacacaca ccuccuaaac                                                  20

<210> SEQ ID NO 131
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 131
uaguaguggg gagagagggu                                                    20

<210> SEQ ID NO 132
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucaaguagug gggagagagg                                                    20

<210> SEQ ID NO 133
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ugagagcaag uagugggag                                                     20

<210> SEQ ID NO 134
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ucugugagag caaguagugg                                                    20

<210> SEQ ID NO 135
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ucucagcgag uacugugaga                                                    20

<210> SEQ ID NO 136
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
uuuguucacc cucagcgagu                                                    20

<210> SEQ ID NO 137
<211> LENGTH: 20
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 137
uuucuuguuc acccucagcg                                                   20

<210> SEQ ID NO 138
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
uuuucuuguu cacccucagc                                                   20

<210> SEQ ID NO 139
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
ugucuuuucu uguucacccu                                                   20

<210> SEQ ID NO 140
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
uuuaucaggu cuuuucuugu                                                   20

<210> SEQ ID NO 141
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
ucugguuaau cuuuaucagg                                                   20

<210> SEQ ID NO 142
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uuuuucuucu gguuaaucuu                                                   20

<210> SEQ ID NO 143
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 143
uuccuuguuu ucuucgguu                                              20

<210> SEQ ID NO 144
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ucuccuuguu uucuucggu                                              20

<210> SEQ ID NO 145
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ucuacaggcu gcgguuguuu                                             20

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uuugcuacag gcugcgguug                                             20

<210> SEQ ID NO 147
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uccagagcuu gcuacaggcu                                             20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
uugaguucca gagcuugcua                                             20

<210> SEQ ID NO 149
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 149
uuccugaguu ccagagcuug                                                      20

<210> SEQ ID NO 150
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
ugacuccuga guuccagagc                                                      20

<210> SEQ ID NO 151
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
ucccuagcgc gcgacuccug                                                      20

<210> SEQ ID NO 152
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
uccccuagcg cgcgacuccu                                                      20

<210> SEQ ID NO 153
<211> LENGTH: 45
<212> TYPE: DNA
<213> ORGANISM: Homo sapiens

<400> SEQUENCE: 153
tctagcaaga gcaggtgtgg gtttaggagg tgtgtgtttt tgttt                          45

<210> SEQ ID NO 154
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
gcaccucucu uuccuagcga                                                      20

<210> SEQ ID NO 155
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
gcuguuugac gcaccucuca                                                      20
```

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
gucgcuguuu gacgcaccua                                                20

<210> SEQ ID NO 157
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157 acugucgcu guuugacgca                                                 20

<210> SEQ ID NO 158
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
uuacgugggc ggaacuugua                                                20

<210> SEQ ID NO 159
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ucuuuuacgu gggcggaaca                                                20

<210> SEQ ID NO 160
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
gucaucuuuu acgugggcga                                                20

<210> SEQ ID NO 161
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
caccugcucu ugcuagacca                                                20

```
<210> SEQ ID NO 162
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
cacaccugcu cuugcuagaa                                                  20

<210> SEQ ID NO 163
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
cuaaacccac accugcucua                                                  20

<210> SEQ ID NO 164
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
acaccuccua aacccacaca                                                  20

<210> SEQ ID NO 165
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aacacacacc uccuaaacca                                                  20

<210> SEQ ID NO 166
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
aaacacacac cuccuaaaca                                                  20

<210> SEQ ID NO 167
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
aaaacacaca ccuccuaaaa                                                  20
```

<210> SEQ ID NO 168
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
aaguaguggg gagagaggga                                               20

<210> SEQ ID NO 169
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gcaaguagug gggagagaga                                               20

<210> SEQ ID NO 170
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
ugagagcaag uaguggggaa                                               20

<210> SEQ ID NO 171
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
acugugagag caaguaguga                                               20

<210> SEQ ID NO 172
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
ccucagcgag uacugugaga                                               20

<210> SEQ ID NO 173
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cuuguucacc cucagcgaga                                               20

<210> SEQ ID NO 174

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
uuucuuguuc acccucagca                                                     20

<210> SEQ ID NO 175
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uuuucuuguu cacccucaga                                                     20

<210> SEQ ID NO 176
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
ggucuuuucu uguucaccca                                                     20

<210> SEQ ID NO 177
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
uuuaucaggu cuuuucuuga                                                     20

<210> SEQ ID NO 178
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
ucugguuaau cuuuaucaga                                                     20

<210> SEQ ID NO 179
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cuccuuguuu ucuucuggua                                                     20

<210> SEQ ID NO 180
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ccuccuuguu uucuucugga                                              20

<210> SEQ ID NO 181
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
gcuacaggcu gcgguuguua                                              20

<210> SEQ ID NO 182
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
cuugcuacag gcugcgguua                                              20

<210> SEQ ID NO 183
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uccagagcuu gcuacaggca                                              20

<210> SEQ ID NO 184
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
cugaguucca gagcuugcua                                              20

<210> SEQ ID NO 185
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
cuccugaguu ccagagcuua                                              20

<210> SEQ ID NO 186
<211> LENGTH: 20
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 186
cgacuccuga guuccagaga 20

<210> SEQ ID NO 187
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 187
ccccuagcgc gcgacuccua 20

<210> SEQ ID NO 188
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 188
gccccuagcg cgcgacucca 20

<210> SEQ ID NO 189
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 189
ucgcuaggaa agagaggugc 20

<210> SEQ ID NO 190
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 190
ugagaggugc gucaaacagc 20

<210> SEQ ID NO 191
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 191
uaggugcguc aaacagcgac 20

<210> SEQ ID NO 192
<211> LENGTH: 20
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 192
uacaaguucc gcccacguaa                                                    20

<210> SEQ ID NO 193
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uguuccgccc acguaaaaga                                                    20

<210> SEQ ID NO 194
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ucgcccacgu aaaagaugac                                                    20

<210> SEQ ID NO 195
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
uggucuagca agagcaggug                                                    20

<210> SEQ ID NO 196
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
uucuagcaag agcaggugug                                                    20

<210> SEQ ID NO 197
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uagagcaggu gugggguuuag                                                   20

<210> SEQ ID NO 198
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 198
uguguggguu uaggaggugu                                                    20

<210> SEQ ID NO 199
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
ugguuuagga gguguguguu                                                    20

<210> SEQ ID NO 200
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uguuuaggag guguguguuu                                                    20

<210> SEQ ID NO 201
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uuuuaggagg uguguguuuu                                                    20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
ucccucucuc cccacuacuu                                                    20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
ucucucuccc cacuacuugc                                                    20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 204
uuccccacua cuugcucuca                                              20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
ucacuacuug cucucacagu                                              20

<210> SEQ ID NO 206
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
ucucgcugag ggugaacaag                                              20

<210> SEQ ID NO 207
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ugcugagggu gaacaagaaa                                              20

<210> SEQ ID NO 208
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
ucugagggug aacaagaaaa                                              20

<210> SEQ ID NO 209
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
ugggugaaca agaaaagacc                                              20

<210> SEQ ID NO 210
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
ucaagaaaag accugauaaa                                           20

<210> SEQ ID NO 211
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
ucugauaaag auuaaccaga                                           20

<210> SEQ ID NO 212
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
uagauuaacc agaagaaaac                                           20

<210> SEQ ID NO 213
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
uaccagaaga aaacaaggag                                           20

<210> SEQ ID NO 214
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
uccagaagaa aacaaggagg                                           20

<210> SEQ ID NO 215
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
uaacaaccgc agccuguagc                                           20

<210> SEQ ID NO 216
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 216
uaaccgcagc cguuagcaag                                               20

<210> SEQ ID NO 217
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
ugccuguagc aagcucugga                                               20

<210> SEQ ID NO 218
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
uaagcucugg aacucaggag                                               20

<210> SEQ ID NO 219
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
ucucuggaac ucaggagucg                                               20

<210> SEQ ID NO 220
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
uaggagucgc gcgcuagggg                                               20

<210> SEQ ID NO 221
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uggagucgcg cgcuaggggc                                               20

<210> SEQ ID NO 222
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
```
ucgcuaggaa agagaggugc                                              20

<210> SEQ ID NO 223
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
ugagaggugc gucaaacagc                                              20

<210> SEQ ID NO 224
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
uaggugcguc aaacagcgac                                              20

<210> SEQ ID NO 225
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
ugcgucaaac agcgacaagu                                              20

<210> SEQ ID NO 226
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
uacaaguucc gcccacguaa                                              20

<210> SEQ ID NO 227
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
uguuccgccc acguaaaaga                                              20

<210> SEQ ID NO 228
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
ucgcccacgu aaaagaugac                                            20

<210> SEQ ID NO 229
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
uggucuagca agagcaggug                                            20

<210> SEQ ID NO 230
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
uucuagcaag agcaggugug                                            20

<210> SEQ ID NO 231
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uagagcaggu gugguuuag                                             20

<210> SEQ ID NO 232
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
uguguggguu uaggaggugu                                            20

<210> SEQ ID NO 233
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ugguuuagga gguguguguu                                            20

<210> SEQ ID NO 234
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
uguuuaggag guguguguuu                                            20

<210> SEQ ID NO 235
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
uuuuaggagg uguguguuuu                                                    20

<210> SEQ ID NO 236
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
ucccucucuc cccacuacuu                                                    20

<210> SEQ ID NO 237
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
ucucucuccc cacuacuugc                                                    20

<210> SEQ ID NO 238
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
uuccccacua cuugcucuca                                                    20

<210> SEQ ID NO 239
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
ucacuacuug cucucacagu                                                    20

<210> SEQ ID NO 240
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
ucucacagua cucgcugagg                                                    20

<210> SEQ ID NO 241
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
ucucgcugag ggugaacaag                                              20

<210> SEQ ID NO 242
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
ugcugagggu gaacaagaaa                                              20

<210> SEQ ID NO 243
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
ucugagggug aacaagaaaa                                              20

<210> SEQ ID NO 244
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
ugggugaaca agaaaagacc                                              20

<210> SEQ ID NO 245
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
ucaagaaaag accugauaaa                                              20

<210> SEQ ID NO 246
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
ucugauaaag auuaaccaga                                              20

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
vuucuucugg uuaaucuuua u                                              21

<210> SEQ ID NO 248
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uagauuaacc agaagaaaac                                                20

<210> SEQ ID NO 249
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
uaccagaaga aaacaaggag                                                20

<210> SEQ ID NO 250
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
uccagaagaa aacaaggagg                                                20

<210> SEQ ID NO 251
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
uaacaaccgc agccuguagc                                                20

<210> SEQ ID NO 252
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
uaaccgcagc cuguagcaag                                                20

<210> SEQ ID NO 253

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
ugccuguagc aagcucugga                                               20

<210> SEQ ID NO 254
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
uagcaagcuc uggaacucag                                               20

<210> SEQ ID NO 255
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
uaagcucugg aacucaggag                                               20

<210> SEQ ID NO 256
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
ucucuggaac ucaggagucg                                               20

<210> SEQ ID NO 257
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
uaggagucgc gcgcuagggg                                               20

<210> SEQ ID NO 258
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
uggagucgcg cgcuaggggc                                               20

<210> SEQ ID NO 259
<211> LENGTH: 45
```

<212> TYPE: DNA
<213> ORGANISM: Homo sapiens

<400> SEQUENCE: 259
gctcgacgca tttttacttt ccctctcatt tctctgaccg aagct            45

<210> SEQ ID NO 260
<211> LENGTH: 45
<212> TYPE: DNA
<213> ORGANISM: Homo sapiens

<400> SEQUENCE: 260
agatgacaca gacttgctta aaggaagtga ctattgtgac ttggg            45

<210> SEQ ID NO 261
<211> LENGTH: 45
<212> TYPE: DNA
<213> ORGANISM: Homo sapiens

<400> SEQUENCE: 261
ggtaatcagt tgtctaaaga agtgcacaga ttacatgtcc gtgtg            45

<210> SEQ ID NO 262
<211> LENGTH: 45
<212> TYPE: DNA
<213> ORGANISM: Homo sapiens

<400> SEQUENCE: 262
gggagagtag ttgcctggtt gtggcagttg gtaaatttct attca            45

<210> SEQ ID NO 263
<211> LENGTH: 45
<212> TYPE: DNA
<213> ORGANISM: Homo sapiens

<400> SEQUENCE: 263
ctggcattac ttctactttt gtacaaagga tcaaaaaaaa aaaag            45

<210> SEQ ID NO 264
<211> LENGTH: 45
<212> TYPE: DNA
<213> ORGANISM: Homo sapiens

<400> SEQUENCE: 264
tctacgttaa ttagatagtt cccaggagga ctaggttagc ctacc            45

<210> SEQ ID NO 265
<211> LENGTH: 45
<212> TYPE: DNA
<213> ORGANISM: Homo sapiens

<400> SEQUENCE: 265
tttaggatcc tgcttctctt tgggctggga gaaaataaac agcat            45

<210> SEQ ID NO 266
<211> LENGTH: 45
<212> TYPE: DNA
<213> ORGANISM: Homo sapiens

<400> SEQUENCE: 266
tgagctgatt ttttcagct gcatttgcat gtatggattt ttctc             45

<210> SEQ ID NO 267

```
<210> SEQ ID NO 267
<211> LENGTH: 45
<212> TYPE: DNA
<213> ORGANISM: Homo sapiens

<400> SEQUENCE: 267
gcatttgcat gtatggattt ttctcaccaa agacgatgac ttcaa          45

<210> SEQ ID NO 268
<211> LENGTH: 45
<212> TYPE: DNA
<213> ORGANISM: Homo sapiens

<400> SEQUENCE: 268
ttgctccagg gttcagttct gttttaggaa atacttttat tttca          45

<210> SEQ ID NO 269
<211> LENGTH: 45
<212> TYPE: DNA
<213> ORGANISM: Homo sapiens

<400> SEQUENCE: 269
aatgatgaaa tattagagtt gtaatattgc ctttatgatt atcca          45

<210> SEQ ID NO 270
<211> LENGTH: 45
<212> TYPE: DNA
<213> ORGANISM: Homo sapiens

<400> SEQUENCE: 270
tcttgacaag atgtggatga aattctttaa gtaaaattgt ttact          45

<210> SEQ ID NO 271
<211> LENGTH: 45
<212> TYPE: DNA
<213> ORGANISM: Homo sapiens

<400> SEQUENCE: 271
attgcaattc ttttacttt cagtcttaga taacaagtct tcaat           45

<210> SEQ ID NO 272
<211> LENGTH: 45
<212> TYPE: DNA
<213> ORGANISM: Homo sapiens

<400> SEQUENCE: 272
attaggcgat tttgtcatta tgcaaacatc atagagtgta cttac          45

<210> SEQ ID NO 273
<211> LENGTH: 45
<212> TYPE: DNA
<213> ORGANISM: Homo sapiens

<400> SEQUENCE: 273
tttaactttt aaaatactta gcttgaaaca caaatacatt gtata          45

<210> SEQ ID NO 274
<211> LENGTH: 45
<212> TYPE: DNA
<213> ORGANISM: Homo sapiens

<400> SEQUENCE: 274
gtagtttatt atcaagtgtt gtacactgta ataattgtat gtgct          45
```

-continued

```
<210> SEQ ID NO 275
<211> LENGTH: 45
<212> TYPE: DNA
<213> ORGANISM: Homo sapiens

<400> SEQUENCE: 275
actaccatca tatatgcagt ctaccattga ctgaaacgtt acatg            45

<210> SEQ ID NO 276
<211> LENGTH: 45
<212> TYPE: DNA
<213> ORGANISM: Homo sapiens

<400> SEQUENCE: 276
aaatgctgta ttggtttctt ggctagcata ttaaatattt ttatc            45

<210> SEQ ID NO 277
<211> LENGTH: 45
<212> TYPE: DNA
<213> ORGANISM: Homo sapiens

<400> SEQUENCE: 277
atattaaata tttttatctt tgtcttgata cttcaatgtc gtttt            45

<210> SEQ ID NO 278
<211> LENGTH: 45
<212> TYPE: DNA
<213> ORGANISM: Homo sapiens

<400> SEQUENCE: 278
tttttttttt ttttgacctt ttagcggctt taaagtattt ctgtt            45

<210> SEQ ID NO 279
<211> LENGTH: 45
<212> TYPE: DNA
<213> ORGANISM: Homo sapiens

<400> SEQUENCE: 279
cctttcttgc cttgtagttt caacaatcca gtatctgcct tttgt            45

<210> SEQ ID NO 280
<211> LENGTH: 45
<212> TYPE: DNA
<213> ORGANISM: Homo sapiens

<400> SEQUENCE: 280
ggaattgaac atatcttttt gggggacaca attcaaccca caagt            45

<210> SEQ ID NO 281
<211> LENGTH: 45
<212> TYPE: DNA
<213> ORGANISM: Homo sapiens

<400> SEQUENCE: 281
atttctaaat gtatgccctg aatataagta acaagttacc atgtc            45

<210> SEQ ID NO 282
<211> LENGTH: 45
<212> TYPE: DNA
<213> ORGANISM: Homo sapiens

<400> SEQUENCE: 282
ccacatcttt gacttaagag gacaaaccaa atatgtctaa atcat            45
```

```
<210> SEQ ID NO 283
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
acuuucccuc ucauuucucu                                                    20

<210> SEQ ID NO 284
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
gcuuaaagga agugacuauu                                                    20

<210> SEQ ID NO 285
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aaagaagugc acagauuaca                                                    20

<210> SEQ ID NO 286
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ugguuguggc aguugguaaa                                                    20

<210> SEQ ID NO 287
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
cuuuuguaca aaggaucaaa                                                    20

<210> SEQ ID NO 288
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
uaguucccag gaggacuagg                                                    20
```

```
<210> SEQ ID NO 289
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
cucuuugggc ugggagaaaa                                                  20

<210> SEQ ID NO 290
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
cagcugcauu ugcauguaug                                                  20

<210> SEQ ID NO 291
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291 gauuuucuc accaaagacg                                                   20

<210> SEQ ID NO 292
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
guucuguuuu aggaaauacu                                                  20

<210> SEQ ID NO 293
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
gaguuguaau auugccuuua                                                  20

<210> SEQ ID NO 294
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
gaugaaauuc uuuaaguaaa                                                  20

<210> SEQ ID NO 295
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
acuuucaguc uuagauaaca                                                    20

<210> SEQ ID NO 296
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
cauuaugcaa acaucauaga                                                    20

<210> SEQ ID NO 297
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
acuuagcuug aaacacaaau                                                    20

<210> SEQ ID NO 298
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
guguuguaca cuguaauaau                                                    20

<210> SEQ ID NO 299
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gcagucuacc auugacugaa                                                    20

<210> SEQ ID NO 300
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
uucuuggcua gcauauuaaa                                                    20

<210> SEQ ID NO 301
<211> LENGTH: 20
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
aucuuugucu ugauacuuca                                              20

<210> SEQ ID NO 302
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
accuuuuagc ggcuuuaaag                                              20

<210> SEQ ID NO 303
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aguuucaaca auccaguauc                                              20

<210> SEQ ID NO 304
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
uuuuuggggg acacaauuca                                              20

<210> SEQ ID NO 305
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
cccugaauau aaguaacaag                                              20

<210> SEQ ID NO 306
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
aagaggacaa accaaauaug                                              20

<210> SEQ ID NO 307
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 307
ugagaaauga gagggaaagu                                                   20

<210> SEQ ID NO 308
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
uauagucacu uccuuuaagc                                                   20

<210> SEQ ID NO 309
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
uguaaucugu gcacuucuuu                                                   20

<210> SEQ ID NO 310
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
uuuaccaacu gccacaacca                                                   20

<210> SEQ ID NO 311
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
uuugauccuu uguacaaaag                                                   20

<210> SEQ ID NO 312
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ucuaguccuc cugggaacua                                                   20

<210> SEQ ID NO 313
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 313
uuuucuccca gcccaaagag                                                    20

<210> SEQ ID NO 314
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
uauacaugca aaugcagcug                                                    20

<210> SEQ ID NO 315
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ugucuuuggu gagaaaaauc                                                    20

<210> SEQ ID NO 316
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uguauuuccu aaaacagaac                                                    20

<210> SEQ ID NO 317
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
uaaaggcaau auuacaacuc                                                    20

<210> SEQ ID NO 318
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
uuuacuuaaa gaauuucauc                                                    20

<210> SEQ ID NO 319
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 319
uguuaucuaa gacugaaagu                                                      20

<210> SEQ ID NO 320
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ucuaugaugu uugcauaaug                                                      20

<210> SEQ ID NO 321
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
uuuuguguuu caagcuaagu                                                      20

<210> SEQ ID NO 322
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uuuauuacag uguacaacac                                                      20

<210> SEQ ID NO 323
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
uucagucaau gguagacugc                                                      20

<210> SEQ ID NO 324
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
uuuaauaugc uagccaagaa                                                      20

<210> SEQ ID NO 325
<211> LENGTH: 20
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 325
ugaaguauca agacaaagau                                               20

<210> SEQ ID NO 326
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
uuuuaaagcc gcuaaaaggu                                               20

<210> SEQ ID NO 327
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uauacuggau uguugaaacu                                               20

<210> SEQ ID NO 328
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
ugaauugugu cccccaaaaa                                               20

<210> SEQ ID NO 329
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
uuuguuacuu auauucaggg                                               20

<210> SEQ ID NO 330
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
uauauuuggu uuguccucuu                                               20

<210> SEQ ID NO 331
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 331
ugagaaauga gagggaaagu                                              20

<210> SEQ ID NO 332
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
uauagucacu uccuuuaagc                                              20

<210> SEQ ID NO 333
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
uguaaucugu gcacuucuuu                                              20

<210> SEQ ID NO 334
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
uuuaccaacu gccacaacca                                              20

<210> SEQ ID NO 335
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
uuugauccuu uguacaaaag                                              20

<210> SEQ ID NO 336
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
ucuaguccuc cugggaacua                                              20

<210> SEQ ID NO 337
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 337
uuuucuccca gcccaaagag                                               20

<210> SEQ ID NO 338
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
uauacaugca aaugcagcug                                               20

<210> SEQ ID NO 339
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
ugucuuuggu gagaaaaauc                                               20

<210> SEQ ID NO 340
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
uguauuuccu aaaacagaac                                               20

<210> SEQ ID NO 341
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
uaaaggcaau auuacaacuc                                               20

<210> SEQ ID NO 342
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
uuuacuuaaa gaauuucauc                                               20

<210> SEQ ID NO 343
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
```
uguuaucuaa gacugaaagu                                            20

<210> SEQ ID NO 344
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
ucuaugaugu uugcauaaug                                            20

<210> SEQ ID NO 345
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
uuuuguguuu caagcuaagu                                            20

<210> SEQ ID NO 346
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
uuuauuacag uguacaacac                                            20

<210> SEQ ID NO 347
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
uucagucaau gguagacugc                                            20

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
uuuaauaugc uagccaagaa                                            20

<210> SEQ ID NO 349
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ugaaguauca agacaaagau 20

<210> SEQ ID NO 350
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
uuuuaaagcc gcuaaaaggu 20

<210> SEQ ID NO 351
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uauacuggau uguugaaacu 20

<210> SEQ ID NO 352
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
ugaauugugu cccccaaaaa 20

<210> SEQ ID NO 353
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
uuuguuacuu auauucaggg 20

<210> SEQ ID NO 354
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uauauuuggu uuguccucuu 20

<210> SEQ ID NO 355
<211> LENGTH: 45
<212> TYPE: DNA
<213> ORGANISM: Homo sapiens

<400> SEQUENCE: 355
cctaatcatt ggtttcatat gtcattgttt agatatctcc ggagc 45

<210> SEQ ID NO 356

<211> LENGTH: 45
<212> TYPE: DNA
<213> ORGANISM: Homo sapiens

<400> SEQUENCE: 356
atatgtcatt gtttagatat ctccggagca tttggataat gtgac          45

<210> SEQ ID NO 357
<211> LENGTH: 45
<212> TYPE: DNA
<213> ORGANISM: Homo sapiens

<400> SEQUENCE: 357
gcatttggat aatgtgacag ttggaatgca gtgatgtcga ctctt          45

<210> SEQ ID NO 358
<211> LENGTH: 45
<212> TYPE: DNA
<213> ORGANISM: Homo sapiens

<400> SEQUENCE: 358
ctgttgccaa gacagagatt gctttaagtg gcaaatcacc tttat          45

<210> SEQ ID NO 359
<211> LENGTH: 45
<212> TYPE: DNA
<213> ORGANISM: Homo sapiens

<400> SEQUENCE: 359
agacagagat tgctttaagt ggcaaatcac ctttattagc agcta          45

<210> SEQ ID NO 360
<211> LENGTH: 45
<212> TYPE: DNA
<213> ORGANISM: Homo sapiens

<400> SEQUENCE: 360
aagacagaac aggtacttct cagtgatgga gaaataactt ttctt          45

<210> SEQ ID NO 361
<211> LENGTH: 45
<212> TYPE: DNA
<213> ORGANISM: Homo sapiens

<400> SEQUENCE: 361
acagaacagg tacttctcag tgatggagaa ataacttttc ttgcc          45

<210> SEQ ID NO 362
<211> LENGTH: 45
<212> TYPE: DNA
<213> ORGANISM: Homo sapiens

<400> SEQUENCE: 362
ccttcgaaat gcagagagtg gtgctataga tgtaaagttt tttgt          45

<210> SEQ ID NO 363
<211> LENGTH: 45
<212> TYPE: DNA
<213> ORGANISM: Homo sapiens

<400> SEQUENCE: 363
gtaaagtttt tgtcttgtc tgaaaaggga gtgattattg tttca          45

```
<210> SEQ ID NO 364
<211> LENGTH: 45
<212> TYPE: DNA
<213> ORGANISM: Homo sapiens

<400> SEQUENCE: 364
aaagggagtg attattgttt cattaatctt tgatggaaac tggaa              45

<210> SEQ ID NO 365
<211> LENGTH: 45
<212> TYPE: DNA
<213> ORGANISM: Homo sapiens

<400> SEQUENCE: 365
ggagtgatta ttgtttcatt aatctttgat ggaaactgga atggg              45

<210> SEQ ID NO 366
<211> LENGTH: 45
<212> TYPE: DNA
<213> ORGANISM: Homo sapiens

<400> SEQUENCE: 366
ccacagacag aacttagttt ctacctccca cttcatagag tgtgt              45

<210> SEQ ID NO 367
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
cauaugucau uguuuagaua                                          20

<210> SEQ ID NO 368
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
gauaucuccg gagcauuugg                                          20

<210> SEQ ID NO 369
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
gacaguugga augcagugau                                          20

<210> SEQ ID NO 370
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
```
agauugcuuu aaguggcaaa                                              20

<210> SEQ ID NO 371
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
uaaguggcaa aucaccuuua                                              20

<210> SEQ ID NO 372
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
cuucucagug auggagaaau                                              20

<210> SEQ ID NO 373
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
cucagugaug gagaaauaac                                              20

<210> SEQ ID NO 374
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
gaguggugcu auagauguaa                                              20

<210> SEQ ID NO 375
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
uugucugaaa agggagugau                                              20

<210> SEQ ID NO 376
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
uguuucauua aucuuugaug                                              20

<210> SEQ ID NO 377
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ucauuaaucu uugauggaaa                                               20

<210> SEQ ID NO 378
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aguuucuacc ucccacuuca                                               20

<210> SEQ ID NO 379
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
uaucuaaaca augacauaug                                               20

<210> SEQ ID NO 380
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ucaaaugcuc cggagauauc                                               20

<210> SEQ ID NO 381
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
uucacugcau uccaacuguc                                               20

<210> SEQ ID NO 382
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
uuugccacuu aaagcaaucu                                               20

<210> SEQ ID NO 383
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
uaaaggugau uugccacuua                                              20

<210> SEQ ID NO 384
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uuuucuccau cacugagaag                                              20

<210> SEQ ID NO 385
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
uuuauuucuc caucacugag                                              20

<210> SEQ ID NO 386
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
uuacaucuau agcaccacuc                                              20

<210> SEQ ID NO 387
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uucacucccu uuucagacaa                                              20

<210> SEQ ID NO 388
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
uaucaaagau uaaugaaaca                                              20

```
<210> SEQ ID NO 389
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
uuuccaucaa agauuaauga                                                    20

<210> SEQ ID NO 390
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
ugaaguggga gguagaaacu                                                    20

<210> SEQ ID NO 391
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
uaucuaaaca augacauaug                                                    20

<210> SEQ ID NO 392
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ucaaaugcuc cggagauauc                                                    20

<210> SEQ ID NO 393
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
uucacugcau uccaacuguc                                                    20

<210> SEQ ID NO 394
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uuugccacuu aaagcaaucu                                                    20

<210> SEQ ID NO 395
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uaaaggugau uugccacuua                                                     20

<210> SEQ ID NO 396
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
uuuucuccau cacugagaag                                                     20

<210> SEQ ID NO 397
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
uuuauuucuc caucacugag                                                     20

<210> SEQ ID NO 398
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
uuacaucuau agcaccacuc                                                     20

<210> SEQ ID NO 399
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
uucacucccu uuucagacaa                                                     20

<210> SEQ ID NO 400
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uaucaaagau uaaugaaaca                                                     20

<210> SEQ ID NO 401
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
uuuccaucaa agauuaauga                                              20

<210> SEQ ID NO 402
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
ugaaguggga gguagaaacu                                              20

<210> SEQ ID NO 403
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
uaucuaaaca augacauaua                                              20

<210> SEQ ID NO 404
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
ccaaaugcuc cggagauaua                                              20

<210> SEQ ID NO 405
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
aucacugcau uccaacugua                                              20

<210> SEQ ID NO 406
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uuugccacuu aaagcaauca                                              20

<210> SEQ ID NO 407
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 407
auuucuccau cacugagaaa                                                    20

<210> SEQ ID NO 408
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
guuauuucuc caucacugaa                                                    20

<210> SEQ ID NO 409
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
uuacaucuau agcaccacua                                                    20

<210> SEQ ID NO 410
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aucacucccu uuucagacaa                                                    20

<210> SEQ ID NO 411
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
caucaaagau uaaugaaaca                                                    20

<210> SEQ ID NO 412
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
ugaaguggga gguagaaaca                                                    20

<210> SEQ ID NO 413
<211> LENGTH: 20
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 413
uauaugucau uguuuagaua                                                    20

<210> SEQ ID NO 414
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uauaucuccg gagcauuugg                                                    20

<210> SEQ ID NO 415
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
uacaguugga augcagugau                                                    20

<210> SEQ ID NO 416
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ugauugcuuu aaguggcaaa                                                    20

<210> SEQ ID NO 417
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
uuucucagug auggagaaau                                                    20

<210> SEQ ID NO 418
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uucagugaug gagaaauaac                                                    20

<210> SEQ ID NO 419
<211> LENGTH: 20
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 419
uaguggugcu auagauguaa                                                     20

<210> SEQ ID NO 420
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
uguuucuacc ucccacuuca                                                     20

<210> SEQ ID NO 421
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
uauaugucau uguuuagaua                                                     20

<210> SEQ ID NO 422
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
uauaucuccg gagcauuugg                                                     20

<210> SEQ ID NO 423
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
uacaguugga augcagugau                                                     20

<210> SEQ ID NO 424
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
ugauugcuuu aaguggcaaa                                                     20

<210> SEQ ID NO 425
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 425
uaaguggcaa aucaccuuua                                           20

<210> SEQ ID NO 426
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uuucucagug auggagaaau                                           20

<210> SEQ ID NO 427
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
uucagugaug gagaaauaac                                           20

<210> SEQ ID NO 428
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
uaguggugcu auagauguaa                                           20

<210> SEQ ID NO 429
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
uugucugaaa agggagugau                                           20

<210> SEQ ID NO 430
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
uguuucauua aucuuugaug                                           20

<210> SEQ ID NO 431
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 431
ucauuaaucu uugauggaaa                                          20

<210> SEQ ID NO 432
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
uguuucuacc ucccacuuca                                          20
```

DUAL-ACTING siRNA BASED MODULATION OF C9orf72

CROSS-REFERENCE TO RELATED APPLICATIONS

This application claims the benefit of U.S. Provisional Application Ser. No. 63/000,899, filed Mar. 27, 2020, the entire disclosure of which is incorporated herein by reference.

STATEMENT REGARDING FEDERALLY SPONSORED RESEARCH OR DEVELOPMENT

This present application was made with government support under Grant Nos. NS104022, HD086111, OD020012, and GM108803 awarded by the National Institutes of Health. The Government has certain rights in the application.

SEQUENCE LISTING

The instant application contains a Sequence Listing which has been submitted electronically in ASCII format and is hereby incorporated by reference in its entirety. Said ASCII copy, created on Jul. 27, 2021, is named 716260_UM9-245_ST25.txt and is 95,467 bytes in size.

FIELD OF THE PRESENT APPLICATION

This disclosure relates to novel C9orf72 targeting sequences, novel oligonucleotides, and novel methods for treating and preventing neurodegeneration in diseases, such as Amyotrophic Lateral Sclerosis and Frontotemporal Dementia.

BACKGROUND

Amyotrophic Lateral Sclerosis (ALS) is a fast-progressing, fatal, neurodegenerative disease that affects motor neurons both in the brain and spinal cord, resulting in the paralysis of voluntary muscles at later stages of disease. ALS affects about 6 persons per 100,000 people and typically leads to death within 3 to 5 years after the onset of symptoms, with no cure available. However, the United States Food and Drug Administration (FDA) approved riluzole for the treatment of ALS in 1995. In fact, riluzole neither improves the clinical state nor stops disease progression, only extending ventilation-free survival by 2 to 3 months for patients with the sporadic or inherited (familial) forms of the disease. More recently, the FDA approved treatment of ALS with edaravone. Unfortunately, edaravone shows no treatment benefit for the majority of ALS patients, with only a specific subset of patients experiencing a slowing of disease progression. Thus, the development of therapeutics that fulfil this clearly unmet medical need is key to transforming not only survival but the quality of life of patients with ALS.

SOD1 and C9orf72 mutations account for the vast majority of inherited cases of ALS (familial ALS, fALS), and cause the death of upper and lower motor neurons through distinct mechanisms. Although SOD1 is a well-established historical target, point mutations in this gene only account for less 10% of the disease cases. On the other hand, recently identified C9 has been associated with more than 40% of patients with fALS and in patients with fronto-temporal dementia (FTD). The $G_4C_2$ hexanucleotide expansion within intron 1 of the C9 gene leads to the formation of nuclear and cytoplasmic RNA foci, but also causes toxic Repeated-Associated Non-ATG (RAN) di-peptides in the cytoplasm. Expression of mutant C9 hexanucleotide occurs both in the sense and antisense direction, which is not included in all C9 mRNA transcripts variants. Thus, C9 has emerged as a promising and well-defined genetic target that can be modulated by therapeutic gene silencing technologies. Moreover, silencing of both the sense and antisense transcript may be important to treat C9-related diseases. Accordingly, there exists a need to effectively silence both the sense and antisense C9 transcripts.

SUMMARY

In one aspect of the present disclosure, there is provided a double-acting RNA silencing agent including a first oligonucleotide strand and a second oligonucleotide strand, each strand comprising a 5' end and a 3' end, wherein the first strand inhibits the expression of a C9orf72 sense transcript and the second strand inhibits the expression of a C9orf72 antisense transcript, wherein the first and second oligonucleotide strand are substantially complementary to a non-repeat region in the C9ORF72 sense and antisense transcript. Target transcripts can include non-mature RNA featuring intronic regions and mature, messenger RNA. The first strand and the second strand can be guide strands forming an siRNA or duplex that is 15 to 30 nucleotides in length. In one exemplary embodiment, the first strand and second strand independently each include at least 16, at least 17, at least 18, at least 19, or at least 20 contiguous nucleotides, and each strand is substantially complementary to a target sequence. In a non-limiting embodiment, the double-acting RNA silencing agent further includes a hydrophobic moiety which can be alkyl, alkenyl, aryl, vitamin, vitamin derivative, cholesterol, cholesterol derivative, lipophilic amino acid, or combinations thereof. In another non-limiting embodiment, the double-acting RNA silencing agent further includes a hydrophilic moiety, for example, an aptamer. In a representative embodiment, the first strand includes a region of complementarity, which is substantially complementary to 5' ACAAGAAAAGAC-CUGAUAAAGAUUAACCAGAAGAAAACAAGGAGG 3' (SEQ ID NO: 1). In a representative embodiment, the first strand comprises a region of complementarity, which is substantially complementary to 5' AGAAAAGAC-CUGAUAAAGAUUAACCAGAAGAAAACAAGGAGG-GAA3' (SEQ ID NO: 2). In another embodiment, the second strand includes a region of complementarity, which is substantially complementary to 5'UCCCUCCUUGUUUUC-UUCUGGUUAAUCUUUAUCAGGUCUUUUCUU 3' (SEQ ID NO: 3). In a representative embodiment, the first strand comprises a region of complementarity, which is substantially complementary to 5' AAGAUUAACCAGAAGAAAAC 3' (SEQ ID NO: 4). In a representative embodiment, the second strand comprises a region of complementarity, which is substantially complementary to 5' GUUUUCUUCUGGUUAAUCUA 3' (SEQ ID NO: 5).

Each of the two strands can include at least one chemically-modified nucleotide. Each modified nucleotide can be a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or combinations thereof. In a further embodiment, there is provided a pharmaceutical composition including the double-acting RNA silencing agent and a pharmaceutically acceptable carrier. In an additional embodiment, there is provided a method for treating or managing a disease or disorder, the method including administering to a subject having a disease- or disorder-associated nucleotide repeat sequence within the C9orf72 gene, a therapeutically effective amount of the double-acting RNA silencing agent. The disease can be amyotrophic lateral sclerosis or frontotemporal dementia.

In a further aspect of the present disclosure, there is provided another type of double-acting RNA silencing agent including a first guide strand and a second guide strand, wherein: (a) the first guide strand and a first passenger strand form a first siRNA; (b) the second guide strand a second passenger strand form a second siRNA, and (c) the first siRNA and the second siRNA are connected to one another by one or more moieties, such as a linker, a spacer, a branching point, or combinations thereof. In a representative embodiment, each siRNA is independently connected to a linker, a spacer, or a branching point at the 3' end or at the 5' end of the guide strand or the passenger strand. For example, each passenger strand can be connected to the linker, spacer, or branching point at the 3' end. Each linker can be an ethylene glycol chain, an alkyl chain, a peptide, an RNA, a DNA, a phosphate, a phosphonate, a phosphoramidate, an ester, an amide, a triazole, or a combination thereof, wherein any carbon or oxygen atom of the linker can optionally be replaced with a nitrogen atom, bear a hydroxyl substituent, or bear an oxo substituent. In a non-limiting embodiment, the double-acting RNA silencing agent further includes a hydrophobic moiety, which can be alkyl, alkenyl, aryl, vitamin, vitamin derivative, cholesterol, cholesterol derivative, lipophilic amino acid, combination thereof. In a representative embodiment, the first strand includes a region of complementarity, which is substantially complementary to 5' ACAAGAAAAGACCUGAUAAAGAUUAACCAGAAGAAAACAAGGAGG 3' (SEQ ID NO: 1). In another embodiment, the second strand includes a region of complementarity which is substantially complementary to 5'UCCCUCCUUGUUUUCUUCUGGUUAAUCUUUAUCAGGUCUUUUCUU3' (SEQ ID NO: 3). Each of the two strands can include at least one chemically-modified nucleotide. Each modified nucleotide can independently be a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a combination thereof.

In certain embodiments, the first oligonucleotide strand is substantially complementary to the second oligonucleotide strand.

In certain embodiments, at least one nucleotide is mismatched between the first strand 5' end and second strand 3' end, and at least one nucleotide is mismatched between the first strand 3' end and second strand 5' end.

In certain embodiments, the RNA silencing agent comprises at least one single stranded nucleotide overhang.

In certain embodiments, the first strand 5' end and second strand 5' end each comprise a 1 nucleotide to 6 nucleotide single stranded nucleotide overhang (e.g., a 1 nucleotide single stranded nucleotide overhang, a 2 nucleotide single stranded nucleotide overhang, a 3 nucleotide single stranded nucleotide overhang, a 4 nucleotide single stranded nucleotide overhang, a 5 nucleotide single stranded nucleotide overhang, or a 6 nucleotide single stranded nucleotide overhang).

In certain embodiments, the first strand 3' end and second strand 3' end each comprise a 1 nucleotide to 6 nucleotide single stranded nucleotide overhang (e.g., a 1 nucleotide single stranded nucleotide overhang, a 2 nucleotide single stranded nucleotide overhang, a 3 nucleotide single stranded nucleotide overhang, a 4 nucleotide single stranded nucleotide overhang, a 5 nucleotide single stranded nucleotide overhang, or a 6 nucleotide single stranded nucleotide overhang).

In a further embodiment, there is provided a pharmaceutical composition including the double-acting RNA silencing agent and a pharmaceutically acceptable carrier. In an additional embodiment, there is provided a method for treating or managing a disease or disorder, the method including administering to a subject having a disease- or disorder-associated nucleotide repeat sequence within the C9orf72 gene, a therapeutically effective amount of the double-acting RNA silencing agent. The disease can be amyotrophic lateral sclerosis or frontotemporal dementia.

In an additional aspect of the present disclosure, there is provided a double-acting, double stranded (ds) RNA including a first guide strand and a second guide strand, wherein at least one nucleotide is mismatched between the first strand 5' end/second strand 3' end and at least one nucleotide is mismatched between the first strand 3' end/second strand 5' end, wherein the first guide strand inhibits the expression of a sense mRNA target and the second guide strand inhibits the expression of an antisense mRNA target. In an exemplary embodiment, the first guide strand 5' end/second guide strand 3' end includes three nucleotide mismatches and the first guide strand 3' end/second guide strand 5' end includes three nucleotide mismatches. In a further embodiment, the dsRNA includes at least one single stranded nucleotide overhang. In example embodiments, each strand of the of the dsRNA can independently include at least one modified nucleotide. Each modified nucleotide can independently be a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, or a combination thereof. In a representative embodiment, the first guide strand includes a region of complementarity which is substantially complementary to 5' ACAAGAAAAGACCUGAUAAAGAUUAACCAGAAGAAAACAAGGAGG3' (SEQ ID NO: 1). In another embodiment, the second strand includes a region of complementarity, which is substantially complementary to 5'UCCCUCCUUGUUUUCUUCUGGUUAAUCUUUAUCAGGUCUUUUCUU 3' (SEQ ID NO: 3). In an embodiment of the dsRNA, at least one of the first target and second target is a disease-associated nucleotide sequence. In certain embodiments, the first guide strand comprises a region of complementarity, which is substantially complementary to 5' AAGAUUAACCAGAAGAAAAC 3' (SEQ ID NO: 4). In certain embodiments, the second guide strand comprises a region of complementarity, which is substantially complementary to 5' GUUUUCUUCUGGUUAAUCUA 3' (SEQ ID NO: 5). In certain embodiments, the first guide strand is substantially complementary to the second guide strand. In certain embodiments, at least one nucleotide is mismatched between the first guide strand 5' end and second guide strand 3' end, and at least one nucleotide is mismatched between the first guide strand 3' end and second guide strand 5' end. In certain embodiments, the first strand 5' end and second strand 5' end each comprise a 1 nucleotide to 6 nucleotide single stranded nucleotide overhang. In certain embodiments, the first strand 3' end and second strand 3' end each comprise a 1 nucleotide to 6 nucleotide single stranded nucleotide overhang.

In a further embodiment, there is provided a pharmaceutical composition including the dsRNA and a pharmaceutically acceptable carrier. In an additional embodiment, there is provided a method for treating or managing a disease or disorder, the method including administering to a subject having a disease- or disorder-associated nucleotide repeat sequence a therapeutically effective amount of the double-acting dsRNA. The repeat sequence can be within the C9orf72 gene, and the disease can be amyotrophic lateral sclerosis or frontotemporal dementia.

In some embodiments, the dsRNA comprises an antisense strand having complementarity to a segment of from 15 to 35 contiguous nucleotides of the nucleic acid sequence of any one of N5' ACAAGAAAAGAC-CUGAUAAAGAUUAACCAGAAGAAAACAAGGAGG 3' (SEQ ID NO: 1) or 5' UCCCUCCUGUUUUCUUCUG-GUUAAUCUUUAUCAGGUCUUUUCUU 3' (SEQ ID NO: 6). In some embodiments, the antisense strand may have complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, 25 contiguous nucleotides, 26 contiguous nucleotides, 27 contiguous nucleotides, 28 contiguous nucleotides, 29 contiguous nucleotides, 30 contiguous nucleotides, 31 contiguous nucleotides, 32 contiguous nucleotides, 33 contiguous nucleotides, 34 contiguous nucleotides, or 35 contiguous nucleotides of 5' ACAAGAAAAGAC-CUGAUAAAGAUUAACCAGAAGAAAACAAGGAGG 3' (SEQ ID NO: 1). In some embodiments, the antisense strand may have complementarity to a segment of 15 contiguous nucleotides, 16 contiguous nucleotides, 17 contiguous nucleotides, 18 contiguous nucleotides, 19 contiguous nucleotides, 20 contiguous nucleotides, 21 contiguous nucleotides, 22 contiguous nucleotides, 23 contiguous nucleotides, 24 contiguous nucleotides, 25 contiguous nucleotides, 26 contiguous nucleotides, 27 contiguous nucleotides, 28 contiguous nucleotides, 29 contiguous nucleotides, 30 contiguous nucleotides, 31 contiguous nucleotides, 32 contiguous nucleotides, 33 contiguous nucleotides, 34 contiguous nucleotides, or 35 contiguous nucleotides of 5' UCCCUCCUGUUUUCUUCUG-GUUAAUCUUUAUCAGGUCUUUUCUU 3' (SEQ ID NO: 6). In some embodiments, the dsRNA comprises an antisense strand that is fully complementary to a C9ORF72 nucleic acid sequence of 5' ACAAGAAAAGAC-CUGAUAAAGAUUAACCAGAAGAAAACAAGGAGG3' (SEQ ID NO: 1) or 5' UCCCUCCUGUUUUCUUCUG-GUUAAUCUUUAUCAGGUCUUUUCUU 3' (SEQ ID NO: 6).

In some embodiments, the antisense strand and/or sense strand comprises about 13 nucleotides to 35 nucleotides in length. For example, In some embodiments, the antisense strand and/or sense strand is 13, 14, 15, 16, 17, 18, 19, 20, 21, 22, 23, 24, 25, 26, 27, 28, 29, 30, 31, 32, 33, 34, or 35 nucleotides in length.

In some embodiments of any one of the foregoing aspects, the antisense strand is 14 nucleotides in length. In some embodiments of any one of the foregoing aspects, the antisense strand is 15 nucleotides in length. In some embodiments, the antisense strand is 16 nucleotides in length. In some embodiments, the antisense strand is 17 nucleotides in length. In some embodiments, the antisense strand is 18 nucleotides in length. In some embodiments, the antisense strand is 19 nucleotides in length. In some embodiments, the antisense strand is 20 nucleotides in length. In some embodiments, the antisense strand is 21 nucleotides in length. In some embodiments, the antisense strand is 22 nucleotides in length. In some embodiments, the antisense strand is 23 nucleotides in length. In some embodiments, the antisense strand is 24 nucleotides in length. In some embodiments, the antisense strand is 25 nucleotides in length. In some embodiments, the antisense strand is 26 nucleotides in length. In some embodiments, the antisense strand is 27 nucleotides in length. In some embodiments, the antisense strand is 28 nucleotides in length. In some embodiments, the antisense strand is 29 nucleotides in length. In some embodiments, the antisense strand is 30 nucleotides in length. In some embodiments, the antisense strand is 31 nucleotides in length. In some embodiments, the antisense strand is 32 nucleotides in length. In some embodiments, the antisense strand is 33 nucleotides in length. In some embodiments, the antisense strand is 34 nucleotides in length. In some embodiments, the antisense strand is 35 nucleotides in length.

In some embodiments, the sense strand is 13 nucleotides in length. In some embodiments, the sense strand is 14 nucleotides in length. In some embodiments, the sense strand is 15 nucleotides in length. In some embodiments, the sense strand is 16 nucleotides in length. In some embodiments, the sense strand is 18 nucleotides in length. In some embodiments, the sense strand is 20 nucleotides in length. In some embodiments, the sense strand is 21 nucleotides in length. In some embodiments, the sense strand is 22 nucleotides in length. In some embodiments, the sense strand is 23 nucleotides in length. In some embodiments, the sense strand is 24 nucleotides in length. In some embodiments, the sense strand is 25 nucleotides in length. In some embodiments, the sense strand is 26 nucleotides in length. In some embodiments, the sense strand is 27 nucleotides in length. In some embodiments, the sense strand is 29 nucleotides in length. In some embodiments, the sense strand is 30 nucleotides in length. In some embodiments, the sense strand is 31 nucleotides in length. In some embodiments, the sense strand is 32 nucleotides in length. In some embodiments, the sense strand is 33 nucleotides in length. In some embodiments, the sense strand is 34 nucleotides in length. In some embodiments, the sense strand is 35 nucleotides in length.

In some embodiments, the antisense strand is 18 nucleotides in length and the sense strand is 14 nucleotides in length.

In some embodiments, the antisense strand is 18 nucleotides in length and the sense strand is 15 nucleotides in length.

In some embodiments, the antisense strand is 18 nucleotides in length and the sense strand is 16 nucleotides in length.

In some embodiments, the antisense strand is 18 nucleotides in length and the sense strand is 17 nucleotides in length.

In some embodiments, the antisense strand is 18 nucleotides in length and the sense strand is 18 nucleotides in length.

In some embodiments, the antisense strand is 19 nucleotides in length and the sense strand is 14 nucleotides in length.

In some embodiments, the antisense strand is 19 nucleotides in length and the sense strand is 15 nucleotides in length.

In some embodiments, the antisense strand is 19 nucleotides in length and the sense strand is 16 nucleotides in length.

In some embodiments, the antisense strand is 19 nucleotides in length and the sense strand is 17 nucleotides in length.

In some embodiments, the antisense strand is 19 nucleotides in length and the sense strand is 18 nucleotides in length.

In some embodiments, the antisense strand is 19 nucleotides in length and the sense strand is 19 nucleotides in length.

In some embodiments, the antisense strand is 20 nucleotides in length and the sense strand is 14 nucleotides in length.

In some embodiments, the antisense strand is 20 nucleotides in length and the sense strand is 15 nucleotides in length.

In some embodiments, the antisense strand is 20 nucleotides in length and the sense strand is 16 nucleotides in length.

In some embodiments, the antisense strand is 20 nucleotides in length and the sense strand is 17 nucleotides in length.

In some embodiments, the antisense strand is 20 nucleotides in length and the sense strand is 18 nucleotides in length.

In some embodiments, the antisense strand is 20 nucleotides in length and the sense strand is 19 nucleotides in length.

In some embodiments, the antisense strand is 20 nucleotides in length and the sense strand is 20 nucleotides in length.

In some embodiments, the antisense strand is 21 nucleotides in length and the sense strand is 14 nucleotides in length.

In some embodiments, the antisense strand is 21 nucleotides in length and the sense strand is 15 nucleotides in length.

In some embodiments, the antisense strand is 21 nucleotides in length and the sense strand is 16 nucleotides in length.

In some embodiments, the antisense strand is 21 nucleotides in length and the sense strand is 17 nucleotides in length.

In some embodiments, the antisense strand is 21 nucleotides in length and the sense strand is 18 nucleotides in length.

In some embodiments, the antisense strand is 21 nucleotides in length and the sense strand is 19 nucleotides in length.

In some embodiments, the antisense strand is 21 nucleotides in length and the sense strand is 20 nucleotides in length.

In some embodiments, the antisense strand is 21 nucleotides in length and the sense strand is 21 nucleotides in length.

In some embodiments, the antisense strand is 22 nucleotides in length and the sense strand is 14 nucleotides in length.

In some embodiments, the antisense strand is 22 nucleotides in length and the sense strand is 15 nucleotides in length.

In some embodiments, the antisense strand is 22 nucleotides in length and the sense strand is 16 nucleotides in length.

In some embodiments, the antisense strand is 22 nucleotides in length and the sense strand is 17 nucleotides in length.

In some embodiments, the antisense strand is 22 nucleotides in length and the sense strand is 18 nucleotides in length.

In some embodiments, the antisense strand is 22 nucleotides in length and the sense strand is 19 nucleotides in length.

In some embodiments, the antisense strand is 22 nucleotides in length and the sense strand is 20 nucleotides in length.

In some embodiments, the antisense strand is 22 nucleotides in length and the sense strand is 21 nucleotides in length.

In some embodiments, the antisense strand is 22 nucleotides in length and the sense strand is 22 nucleotides in length.

In some embodiments, the antisense strand is 23 nucleotides in length and the sense strand is 14 nucleotides in length.

In some embodiments, the antisense strand is 23 nucleotides in length and the sense strand is 15 nucleotides in length.

In some embodiments, the antisense strand is 23 nucleotides in length and the sense strand is 16 nucleotides in length.

In some embodiments, the antisense strand is 23 nucleotides in length and the sense strand is 17 nucleotides in length.

In some embodiments, the antisense strand is 23 nucleotides in length and the sense strand is 18 nucleotides in length.

In some embodiments, the antisense strand is 23 nucleotides in length and the sense strand is 19 nucleotides in length.

In some embodiments, the antisense strand is 23 nucleotides in length and the sense strand is 20 nucleotides in length.

In some embodiments, the antisense strand is 23 nucleotides in length and the sense strand is 21 nucleotides in length.

In some embodiments, the antisense strand is 23 nucleotides in length and the sense strand is 22 nucleotides in length.

In some embodiments, the antisense strand is 23 nucleotides in length and the sense strand is 23 nucleotides in length.

In some embodiments, the antisense strand is 24 nucleotides in length and the sense strand is 14 nucleotides in length.

In some embodiments, the antisense strand is 24 nucleotides in length and the sense strand is 15 nucleotides in length.

In some embodiments, the antisense strand is 24 nucleotides in length and the sense strand is 16 nucleotides in length.

In some embodiments, the antisense strand is 24 nucleotides in length and the sense strand is 17 nucleotides in length.

In some embodiments, the antisense strand is 24 nucleotides in length and the sense strand is 18 nucleotides in length.

In some embodiments, the antisense strand is 24 nucleotides in length and the sense strand is 19 nucleotides in length.

In some embodiments, the antisense strand is 24 nucleotides in length and the sense strand is 20 nucleotides in length.

In some embodiments, the antisense strand is 24 nucleotides in length and the sense strand is 21 nucleotides in length.

In some embodiments, the antisense strand is 24 nucleotides in length and the sense strand is 22 nucleotides in length.

In some embodiments, the antisense strand is 24 nucleotides in length and the sense strand is 23 nucleotides in length.

In some embodiments, the antisense strand is 24 nucleotides in length and the sense strand is 24 nucleotides in length.

In some embodiments, the antisense strand is 25 nucleotides in length and the sense strand is 14 nucleotides in length.

In some embodiments, the antisense strand is 25 nucleotides in length and the sense strand is 15 nucleotides in length.

In some embodiments, the antisense strand is 25 nucleotides in length and the sense strand is 16 nucleotides in length.

In some embodiments, the antisense strand is 25 nucleotides in length and the sense strand is 17 nucleotides in length.

In some embodiments, the antisense strand is 25 nucleotides in length and the sense strand is 18 nucleotides in length.

In some embodiments, the antisense strand is 25 nucleotides in length and the sense strand is 19 nucleotides in length.

In some embodiments, the antisense strand is 25 nucleotides in length and the sense strand is 20 nucleotides in length.

In some embodiments, the antisense strand is 25 nucleotides in length and the sense strand is 21 nucleotides in length.

In some embodiments, the antisense strand is 25 nucleotides in length and the sense strand is 22 nucleotides in length.

In some embodiments, the antisense strand is 25 nucleotides in length and the sense strand is 23 nucleotides in length.

In some embodiments, the antisense strand is 25 nucleotides in length and the sense strand is 24 nucleotides in length.

In some embodiments, the antisense strand is 25 nucleotides in length and the sense strand is 25 nucleotides in length.

In some embodiments, the antisense strand is 26 nucleotides in length and the sense strand is 14 nucleotides in length.

In some embodiments, the antisense strand is 26 nucleotides in length and the sense strand is 15 nucleotides in length.

In some embodiments, the antisense strand is 26 nucleotides in length and the sense strand is 16 nucleotides in length.

In some embodiments, the antisense strand is 26 nucleotides in length and the sense strand is 17 nucleotides in length.

In some embodiments, the antisense strand is 26 nucleotides in length and the sense strand is 18 nucleotides in length.

In some embodiments, the antisense strand is 26 nucleotides in length and the sense strand is 19 nucleotides in length.

In some embodiments, the antisense strand is 26 nucleotides in length and the sense strand is 20 nucleotides in length.

In some embodiments, the antisense strand is 26 nucleotides in length and the sense strand is 21 nucleotides in length.

In some embodiments, the antisense strand is 26 nucleotides in length and the sense strand is 22 nucleotides in length.

In some embodiments, the antisense strand is 26 nucleotides in length and the sense strand is 23 nucleotides in length.

In some embodiments, the antisense strand is 26 nucleotides in length and the sense strand is 24 nucleotides in length.

In some embodiments, the antisense strand is 26 nucleotides in length and the sense strand is 25 nucleotides in length.

In some embodiments, the antisense strand is 26 nucleotides in length and the sense strand is 26 nucleotides in length.

In some embodiments, the antisense strand is 27 nucleotides in length and the sense strand is 14 nucleotides in length.

In some embodiments, the antisense strand is 27 nucleotides in length and the sense strand is 15 nucleotides in length.

In some embodiments, the antisense strand is 27 nucleotides in length and the sense strand is 16 nucleotides in length.

In some embodiments, the antisense strand is 27 nucleotides in length and the sense strand is 17 nucleotides in length.

In some embodiments, the antisense strand is 27 nucleotides in length and the sense strand is 18 nucleotides in length.

In some embodiments, the antisense strand is 27 nucleotides in length and the sense strand is 19 nucleotides in length.

In some embodiments, the antisense strand is 27 nucleotides in length and the sense strand is 20 nucleotides in length.

In some embodiments, the antisense strand is 27 nucleotides in length and the sense strand is 21 nucleotides in length.

In some embodiments, the antisense strand is 27 nucleotides in length and the sense strand is 22 nucleotides in length.

In some embodiments, the antisense strand is 27 nucleotides in length and the sense strand is 23 nucleotides in length.

In some embodiments, the antisense strand is 27 nucleotides in length and the sense strand is 24 nucleotides in length.

In some embodiments, the antisense strand is 27 nucleotides in length and the sense strand is 25 nucleotides in length.

In some embodiments, the antisense strand is 27 nucleotides in length and the sense strand is 26 nucleotides in length.

In some embodiments, the antisense strand is 27 nucleotides in length and the sense strand is 27 nucleotides in length.

In some embodiments, the antisense strand is 28 nucleotides in length and the sense strand is 14 nucleotides in length.

In some embodiments, the antisense strand is 28 nucleotides in length and the sense strand is 15 nucleotides in length.

In some embodiments, the antisense strand is 28 nucleotides in length and the sense strand is 16 nucleotides in length.

In some embodiments, the antisense strand is 28 nucleotides in length and the sense strand is 17 nucleotides in length.

In some embodiments, the antisense strand is 28 nucleotides in length and the sense strand is 18 nucleotides in length.

In some embodiments, the antisense strand is 28 nucleotides in length and the sense strand is 19 nucleotides in length.

In some embodiments, the antisense strand is 28 nucleotides in length and the sense strand is 20 nucleotides in length.

In some embodiments, the antisense strand is 28 nucleotides in length and the sense strand is 21 nucleotides in length.

In some embodiments, the antisense strand is 28 nucleotides in length and the sense strand is 22 nucleotides in length.

In some embodiments, the antisense strand is 28 nucleotides in length and the sense strand is 23 nucleotides in length.

In some embodiments, the antisense strand is 28 nucleotides in length and the sense strand is 24 nucleotides in length.

In some embodiments, the antisense strand is 28 nucleotides in length and the sense strand is 25 nucleotides in length.

In some embodiments, the antisense strand is 28 nucleotides in length and the sense strand is 26 nucleotides in length.

In some embodiments, the antisense strand is 28 nucleotides in length and the sense strand is 27 nucleotides in length.

In some embodiments, the antisense strand is 28 nucleotides in length and the sense strand is 28 nucleotides in length.

In some embodiments, the antisense strand is 29 nucleotides in length and the sense strand is 14 nucleotides in length.

In some embodiments, the antisense strand is 29 nucleotides in length and the sense strand is 15 nucleotides in length.

In some embodiments, the antisense strand is 29 nucleotides in length and the sense strand is 16 nucleotides in length.

In some embodiments, the antisense strand is 29 nucleotides in length and the sense strand is 17 nucleotides in length.

In some embodiments, the antisense strand is 29 nucleotides in length and the sense strand is 18 nucleotides in length.

In some embodiments, the antisense strand is 29 nucleotides in length and the sense strand is 19 nucleotides in length.

In some embodiments, the antisense strand is 29 nucleotides in length and the sense strand is 20 nucleotides in length.

In some embodiments, the antisense strand is 29 nucleotides in length and the sense strand is 21 nucleotides in length.

In some embodiments, the antisense strand is 29 nucleotides in length and the sense strand is 22 nucleotides in length.

In some embodiments, the antisense strand is 29 nucleotides in length and the sense strand is 23 nucleotides in length.

In some embodiments, the antisense strand is 29 nucleotides in length and the sense strand is 24 nucleotides in length.

In some embodiments, the antisense strand is 29 nucleotides in length and the sense strand is 25 nucleotides in length.

In some embodiments, the antisense strand is 29 nucleotides in length and the sense strand is 26 nucleotides in length.

In some embodiments, the antisense strand is 29 nucleotides in length and the sense strand is 27 nucleotides in length.

In some embodiments, the antisense strand is 29 nucleotides in length and the sense strand is 28 nucleotides in length.

In some embodiments, the antisense strand is 29 nucleotides in length and the sense strand is 29 nucleotides in length.

In some embodiments, the antisense strand is 30 nucleotides in length and the sense strand is 14 nucleotides in length.

In some embodiments, the antisense strand is 30 nucleotides in length and the sense strand is 15 nucleotides in length.

In some embodiments, the antisense strand is 30 nucleotides in length and the sense strand is 16 nucleotides in length.

In some embodiments, the antisense strand is 30 nucleotides in length and the sense strand is 17 nucleotides in length.

In some embodiments, the antisense strand is 30 nucleotides in length and the sense strand is 18 nucleotides in length.

In some embodiments, the antisense strand is 30 nucleotides in length and the sense strand is 19 nucleotides in length.

In some embodiments, the antisense strand is 30 nucleotides in length and the sense strand is 20 nucleotides in length.

In some embodiments, the antisense strand is 30 nucleotides in length and the sense strand is 21 nucleotides in length.

In some embodiments, the antisense strand is 30 nucleotides in length and the sense strand is 22 nucleotides in length.

In some embodiments, the antisense strand is 30 nucleotides in length and the sense strand is 23 nucleotides in length.

In some embodiments, the antisense strand is 30 nucleotides in length and the sense strand is 24 nucleotides in length.

In some embodiments, the antisense strand is 30 nucleotides in length and the sense strand is 25 nucleotides in length.

In some embodiments, the antisense strand is 30 nucleotides in length and the sense strand is 26 nucleotides in length.

In some embodiments, the antisense strand is 30 nucleotides in length and the sense strand is 27 nucleotides in length.

In some embodiments, the antisense strand is 30 nucleotides in length and the sense strand is 28 nucleotides in length.

In some embodiments, the antisense strand is 30 nucleotides in length and the sense strand is 29 nucleotides in length.

In some embodiments, the dsRNA comprises a double-stranded region of 14 base pairs to 30 base pairs (e.g., 14 base pairs, 15 base pairs, 16 base pairs, 17 base pairs, 18 base pairs, 19 base pairs, 20 base pairs, 21 base pairs, 22 base pairs, 23 base pairs, 24 base pairs, 25 base pairs, 26 base pairs, 27 base pairs, 28 base pairs, 29 base pairs, or 30 base pairs). In some embodiments, the dsRNA comprises a double-stranded region of 14 base pairs. In some embodiments, the dsRNA comprises a double-stranded region of 15 base pairs. In some embodiments, the dsRNA comprises a double-stranded region of 16 base pairs. In some embodiments, the dsRNA comprises a double-stranded region of 17 base pairs. In some embodiments, the dsRNA comprises a double-stranded region of 18 base pairs. In some embodiments, the dsRNA comprises a double-stranded region of 19 base pairs. In some embodiments, the dsRNA comprises a double-stranded region of 20 base pairs. In some embodiments, the dsRNA comprises a double-stranded region of 21 base pairs. In some embodiments, the dsRNA comprises a double-stranded region of 22 base pairs. In some embodiments, the dsRNA comprises a double-stranded region of 23 base pairs. In some embodiments, the dsRNA comprises a double-stranded region of 24 base pairs. In some embodiments, the dsRNA comprises a double-stranded region of 25 base pairs. In some embodiments, the dsRNA comprises a double-stranded region of 26 base pairs. In some embodiments, the dsRNA comprises a double-stranded region of 27 base pairs. In some embodiments, the dsRNA comprises a double-stranded region of 28 base pairs. In some embodiments, the dsRNA comprises a double-stranded region of 29 base pairs. In some embodiments, the dsRNA comprises a double-stranded region of 30 base pairs.

In another aspect, the disclosure provides a branched oligonucleotide compound comprising at least two double-acting RNA silencing agents, wherein each double-acting RNA silencing agent comprises: a first guide strand comprising a 5' end and a 3' end, and a second guide strand comprising a 5' end and a 3' end, wherein the at least two double-acting RNA silencing agents are connected to one another by one or more moieties comprising a linker, a spacer, or a branching point.

In certain embodiments of the branched oligonucleotide compound, each double-acting RNA silencing agent comprises a linker, a spacer, or a branching point, at the 3' end or at the 5' end of the first or second guide strand.

In certain embodiments of the branched oligonucleotide compound, each second guide strand comprises the linker, spacer, or branching point at the 3' end.

In certain embodiments of the branched oligonucleotide compound, each linker comprises an ethylene glycol chain, an alkyl chain, a peptide, an RNA, a DNA, a phosphate, a phosphonate, a phosphoramidate, an ester, an amide, a triazole, or a combination thereof, wherein any carbon or oxygen atom of the linker is optionally replaced with a nitrogen atom, bears a hydroxyl substituent, or bears an oxo substituent.

In certain embodiments, the branched oligonucleotide compound further comprises a hydrophobic moiety or a hydrophilic moiety.

In certain embodiments of the branched oligonucleotide compound, the hydrophobic moiety comprises alkyl, alkenyl, aryl, vitamin, vitamin derivative, cholesterol, cholesterol derivative, lipophilic amino acid, or a combination thereof.

2 In certain embodiments of the branched oligonucleotide compound, the first guide strand comprising a region of complementarity, which is substantially complementary to 5' ACAAGAAAAGAC-CUGAUAAAGAUUAACCAGAAGAAAACAAGGAGG 3' (SEQ ID NO: 1).

In certain embodiments of the branched oligonucleotide compound, the second guide strand comprising a region of complementarity, which is substantially complementary to 5'UCCCUCCUUGUUUUCUUCUGGUUAAUC-UUUAUCAGGUCUUUUCUU 3' (SEQ ID NO: 3).

In certain embodiments of the branched oligonucleotide compound, the first guide strand comprises a region of complementarity, which is substantially complementary to 5' AGAAAAGAC-CUGAUAAAGAUUAACCAGAAGAAAACAAGGAGG-GAA 3' (SEQ ID NO: 2).

In certain embodiments of the branched oligonucleotide compound, the first guide strand comprises a region of complementarity, which is substantially complementary to 5' AAGAUUAACCAGAAGAAAAC 3' (SEQ ID NO: 4).

In certain embodiments of the branched oligonucleotide compound, the second guide strand comprises a region of complementarity, which is substantially complementary to 5' GUUUUCUUCUGGUUAAUCUA 3' (SEQ ID NO: 5).

In certain embodiments of the branched oligonucleotide compound, each strand comprises one or more chemically-modified nucleotides.

In certain embodiments of the branched oligonucleotide compound, the modified nucleotide comprises a 2'-O-methyl modified nucleotide, a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

In certain embodiments of the branched oligonucleotide compound, the first guide strand is substantially complementary to the second guide strand.

In certain embodiments of the branched oligonucleotide compound, at least one nucleotide is mismatched between the first guide strand 5' end and second guide strand 3' end, and at least one nucleotide is mismatched between the first strand 3' end and second strand 5' end.

In certain embodiments of the branched oligonucleotide compound, at least one dual-acting RNA silencing agent comprises at least one single stranded nucleotide overhang.

In certain embodiments of the branched oligonucleotide compound, the first guide strand 5' end and second guide strand 5' end each comprise a 1 nucleotide to 6 nucleotide single stranded nucleotide overhang.

In certain embodiments of the branched oligonucleotide compound, the first guide strand 3' end and second guide strand 3' end each comprise a 1 nucleotide to 6 nucleotide single stranded nucleotide overhang.

In another aspect, the disclosure provides a pharmaceutical composition comprising the branched oligonucleotide compound recited above and a pharmaceutically acceptable carrier.

In another aspect, the disclosure provides a method for treating or managing a disease or disorder comprising administering to a subject having a disease- or disorder-associated nucleotide repeat sequence within the C9orf72 gene a therapeutically effective amount of the branched oligonucleotide compound recited above.

In certain embodiments, the disease or disorder comprises amyotrophic lateral sclerosis.

In certain embodiments, the disease or disorder comprises frontotemporal dementia.

BRIEF DESCRIPTION OF THE DRAWINGS

The foregoing and other features and advantages of the present application will be more fully understood from the following detailed description of illustrative embodiments taken in conjunction with the accompanying drawings.

(FIG. 1B) Schematic of the non-pathological sense strand and the siRNA targeted region within exon 2. (FIG. 1C) Schematic of the pathological, hexanucleotide repeat-containing sense strand and the siRNA non-selective targeting region within exon 2 and the selective siRNA targeting region consisting of exon 1a and a region in intron 1. (FIG. 1D) Schematic of the pathological, hexanucleotide repeat containing antisense strand and the selective siRNA targeting region consisting of exon 1a and a region in intron 1.

(FIG. 12A) graphically depicts the reduction in the percentage of cells with nuclear foci between the untreated control cells in the C9.2 patient fibroblasts and the increase in the percentage of cells with no nuclear foci in these cells. (FIG. 12B) graphically depicts the reduction in the percentage of cells with cytoplasmic foci in the C9.2 patient fibroblasts treated with siRNA candidates compared to untreated patient fibroblasts and the increase in the percentage of cells with no cytoplasmic foci. (FIG. 12C) graphically depicts the reduction in the percentage of cells with nuclear foci between the untreated control cells in the C9.3 patient fibroblasts and C9.3 patient fibroblasts treated with siRNA candidates and the increase in the percentage of cells with no nuclear foci in these cells. (FIG. 12D) graphically depicts the reduction in the percentage of cells with cytoplasmic foci in the C9.3 patient fibroblasts treated with siRNA candidates compared to untreated patient fibroblasts and the increase in the percentage of cells with no cytoplasmic foci.

FIG. 13A FIG. 13B are representative images of C9.3 patient fibroblasts. (FIG. 13A) is a representative image of untreated C9.3 patient fibroblasts nuclear stained with DAPI in blue and foci in red. (FIG. 13B) is a representative image of C9.3 patient fibroblasts treated with an siRNA candidate nuclear stained with DAPI in blue and RNA foci in red. Scale bar=10 µm.

(FIG. 18A) depicts the levels of C9orf72 mRNA expression determined by qPCR in Patient C9.2 fibroblasts after siRNA treatment relative to untreated control cells. (FIG. 18B) depicts the levels of C9orf72 mRNA expression determined by qPCR in Patient C9.3 fibroblasts after siRNA treatment relative to untreated control cells. (FIG. 18C) depicts the averaged expression of both C9 patient fibroblasts relative to untreated control cells.

FIG. 24A-FIG. 24B are visual comparisons of traditional and novel dual-acting chemical scaffolds. FIG. 24A depicts an example traditional siRNA. FIG. 24B depicts an example dual-acting chemical scaffold.

FIG. 27A-FIG. 27D depict schematics of blunt-ended dual-acting RNA silencing agents, with a first guide strand targeting an antisense transcript, and a second guide strand targeting a sense transcript. The dual-acting RNA silencing agent may be in a monomer form (FIG. 27A) or a branched form (FIG. 27B, FIG. 27C, FIG. 27D).

DETAILED DESCRIPTION OF CERTAIN EXEMPLARY EMBODIMENTS

Figure 1A:
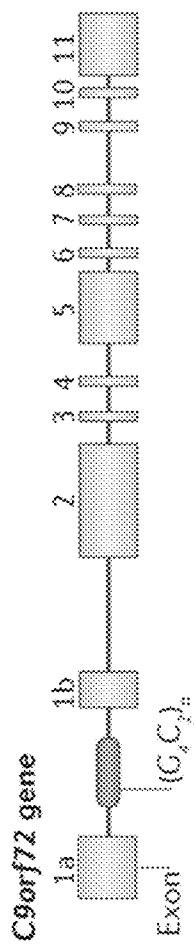
FIG. 1A-FIG. 1D is a schematic adapted from Haeusler et al. (Nature Reviews Neuroscience volume 17, pages 383-395 (2016)) that illustrates the C9orf72 gene and the regions non-selectively or selectively targeted in the sense and antisense product. (FIG. TA) Schematic of the C9orf72 gene and the intronic hexanucleotide repeat region.
Figure 1B:
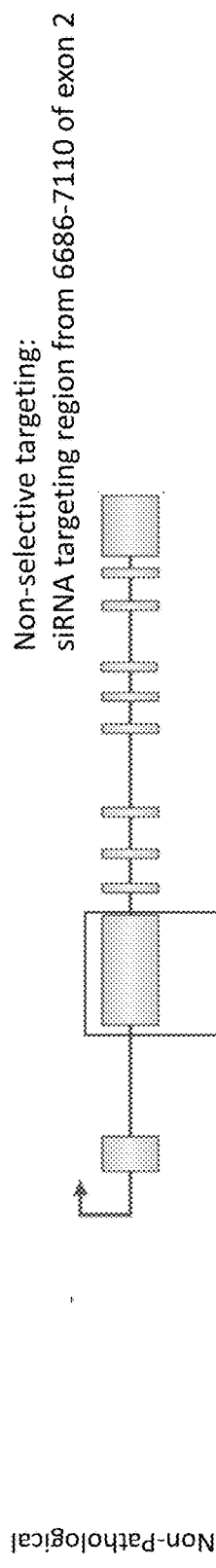
Figure 1C:
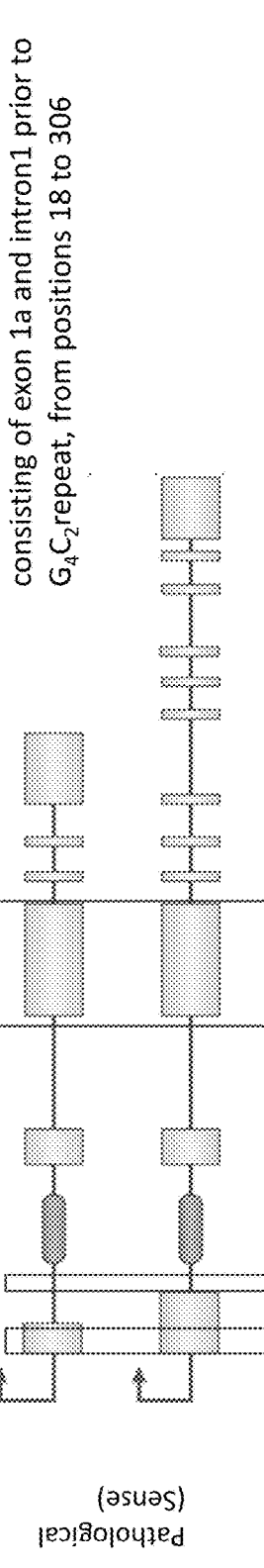
Figure 1D:
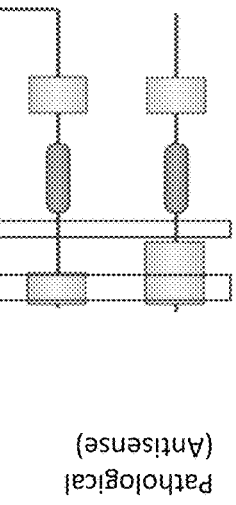

Provided herein are novel C9ORF72 target sequences, including isoform-selective and non-selective target sequences. Also provided are novel siRNAs that enable specific and non-specific mRNA variant modulation by targeting selective and non-selective target sequences of C9ORF72 mRNAs. Methods of treating C90RF72-related pathologies, for example amyotrophic lateral sclerosis (ALS) and frontotemporal degeneration (FTD) are also provided.

Using a platform of fully modified hydrophobic siRNAs (FM-hsiRNA), which provide resistance to nuclease degradation and self-delivering capabilities, a screening of more than 100 sequences targeting C9ORF72 was performed. About 15 hits targeting different regions of interest were identified. Secondary screens were performed in human patient fibroblasts and allowed identification of targeting intronic and exonic regions to enable variant specific, but also non-specific, modulation of C9ORF72. The identified compounds downregulated relevant C9ORF72 mRNA variants, and were also able to reduce RNA foci formation in the nucleus and cytoplasm. The compounds were also effective in reducing the expression of di-peptides, one of the major determinants of C9ORF72 toxicity.

RAN dipeptides are expressed from sense and antisense hexanucleotide-containing transcripts and both need to be targeted to reduce C9-related neuropathology. The current disclosure introduces for the first time the concept of dual-targeting siRNAs for non-repeat regions of C9ORF72, which carry 2 guide strands within the same molecule to enable simultaneous silencing of both sense and antisense transcripts.

As used herein, the C9ORF72 repeat region corresponds to the $G_4C_2$ hexanucleotide repeat region found in intron 1 of the C9ORF72 gene. The double-acting RNA silencing agents of the disclosure are designed to target a region outside of the hexanucleotide repeat in both the sense and antisense transcript of the C9ORF72 gene. As used herein, a "non-repeat region" corresponds to a nucleic acid sequence of the C9ORF72 gene that does not contain the hexanucleotide repeat.

Unless otherwise specified, nomenclature used in connection with cell and tissue culture, molecular biology, immunology, microbiology, genetics and protein and nucleic acid chemistry and hybridization described herein are those well-known and commonly used in the art. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the present application can be more readily understood, certain terms are first defined.

By "alteration" is meant a change (increase or decrease) in the expression levels of a gene, mRNA, or polypeptide as detected by standard art known methods such as those described herein. As used herein, an increase or decrease includes a 10% change in expression levels, a 25% change, a 40% change, or a 50% or greater change in expression levels. In certain embodiments, an increase or decrease is a change in expression levels of between about 30% and about 50% or between about 30% and about 40%. "Alteration" can also indicate a change (increase or decrease) in the biological activity of any of the mRNAs or polypeptides of the present application (e.g., C9ORF72 and RAN peptides). Examples of biological activity for C9ORF72 include one or more clinical symptoms of neurodegenerative diseases, for example ALS and FTD. As used herein, an increase or decrease includes a 10% change in biological activity, a 25% change, a 40% change, or a 50% or greater change in biological activity. In certain preferred embodiments, an increase or decrease is a change in expression levels of between about 30% and about 50% or between about 30% and about 40%.

Certain embodiments of the present application are directed to the treatment of ALS or other C9ORF72 diseases. By "treatment of a C9ORF72-related disorder" is meant use of an oligonucleotide (e.g., an siRNA) of the present application in a pharmaceutical composition for the treatment of disorders related to C9ORF72. As such, pharmaceutical compositions containing the oligonucleotide are useful for treating diseases, conditions and disorders that require inhibition of cellular processes, such as C9ORF72 expression, RAN peptide formation, and the creation of C9ORF72 nuclear or cytoplasmic foci.

By "amyotrophic lateral sclerosis" ("ALS"), is meant the nervous system disorder that is characterized by the death of neurons controlling voluntary muscles. ALS is characterized by stiff muscles, muscle twitching, and gradually worsening weakness due to muscles decreasing in size.

By "therapeutic amount" is meant an amount that when administered to a patient suffering from ALS or other disease is sufficient to cause a qualitative or quantitative reduction in the symptoms of ALS or other disease as described herein. A "therapeutic amount" can also mean an amount that when administered to a patient or subject suffering from ALS or other disease is sufficient to cause a reduction in the expression levels of one or more C9ORF72 RAN peptides or of C9ORF72 transcripts and a reduction in the formation of RAN-related foci as measured by one or more of the assays described herein.

By "subject" is meant a mammal, including, but not limited to, a human or non-human mammal, such as non-human primates or other animals such as, e.g., bovine, equine, canine, ovine, feline, murine and the like.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. In one embodiment, a siRNA comprises between about 15-30 nucleotides or nucleotide analogs, between about 16-25 nucleotides (or nucleotide analogs), between about 18-23 nucleotides (or nucleotide analogs), or between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs can, in some instances, include fewer than 19 nucleotides, e.g., 16, 17 or 18 nucleotides, provided that the shorter siRNA retains the ability to mediate RNAi. Likewise, long siRNAs can, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which can be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs can also comprise modifications to the sugar portion of the nucleotides. For example, the 2' OH-group can be replaced by a group selected from H, OR, R, F, Cl, Br, I, SH, SR, NH2, NHR, NR2, COOR, or, wherein R is substituted or unsubstituted C1-C6 alkyl, alkenyl, alkynyl, aryl, etc. Other possible modifications include those described in U.S. Pat. Nos. 5,858,988, and 6,291,438.

The phosphate group of the nucleotide can also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides can be linked with linkages which result in a lower rate of hydrolysis of the RNA analog as compared to an RNA molecule with phosphodiester linkages. For example, the nucleotides of the analog can comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts, and typically ex vivo living cells, e.g., immortalized cells, primary cells, and cell lines. The term "in vivo" also has its art recognized meaning, e.g. cells in an organism.

As used herein, the term "transgene" refers to any nucleic acid molecule, which is inserted by artifice into a cell, and becomes part of the genome of the organism that develops from the cell. Such a transgene can include a gene that is partly or entirely heterologous (i.e., foreign) to the transgenic organism, or can represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and can include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein (e.g., causes production of one or more C9ORF72 RAN peptides) or causes interactions with other proteins. In another embodiment, the gain-of-function mutation causes a decrease in or removal of normal wild-type protein, for example, by interaction of the altered, mutant protein with said normal, wild-type protein. Certain gain-of-function mutations can create toxic RNA species, the mutant RNA being toxic itself by forming RNA foci that can sequester transcription factors or exert other deleterious effects associated with neurological and neuromuscolar diseases or disorders.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism can comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population can comprise 50, 75, 100, 200, 500, 1000 or more individuals. In particular embodiments, the sample population can comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity can be calculated for a sample population using methods that are well known to those skilled in the art.

The term "trinucleotide repeat" or "trinucleotide repeat region" as used herein, refers to a segment of a nucleic acid sequence e.g.,) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE mental retardation, Friedreich's ataxia and myotonic dystrophy. Exemplary trinucleotide repeat diseases for treatment according to the present application are those characterized or caused by an expanded trinucleotide repeat region at the 5' end of the coding region of a gene, the gene encoding a mutant protein which causes or is causative of the disease or disorder.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small non-coding RNAs can be generated. Exemplary RNA silencing agents include siRNAs, miRNAs, siRNA-like duplexes, shRNas, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-µ☐, wherein T is an mRNA targeting moiety, L is a linking moiety, and p is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA targeting moiety to the miRNA recruiting moiety.

As used herein, the term "antisense strand" of an RNA silencing agent, e.g., an siRNA or RNA silencing agent, refers to a strand that is substantially complementary to a section of about 10-50 nucleotides, e.g., about 15-25, 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. In the context of dual targeting where both sense and antisense transcripts are targeted, each of the first and second strand will have complementarity to the sense or antisense transcript.

miRNA duplex intermediates or siRNA-like duplexes include a miRNA strand having sufficient complementarity to a section of about 10-50 nucleotides of the mRNA of the gene targeted for silencing and a miRNA strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant present application include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the present application into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this present application belongs. Although methods and materials similar or equivalent to those described herein can be used in the practice or testing of the present application, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the present application are described in further detail in the following subsections.

I. Novel Target Sequences

In some embodiments, the RNA silencing agents of the present application are designed to target selective and non-selective regions in C9ORF72 mRNA molecules. Certain C9ORF72 mRNAs can encode for RAN peptides.

The present application targets regions within one or more C9ORF72 mRNAs and their corresponding proteins. One strand of double-stranded RNA (siRNA) complements a target sequence within the C9ORF72 mRNA. After introduction of siRNA into a subject or cell, the siRNA partially unwinds, binds to the target region within the C9ORF72 mRNA in a site-specific manner, and activates an mRNA nuclease. This nuclease cleaves the C9ORF72 mRNA, thereby halting translation of the C9ORF72 protein or RAN peptides. Cells rid themselves of partially digested mRNA, thus precluding translation, or cells digest partially translated proteins. In certain embodiments, C9ORF72 protein or RAN peptide expression is reduced in a subject or cell by about 30% to 50%, or by about 30% to 40%.

In embodiments of the present application, RNA silencing agents of the present application are capable of targeting transcripts of one or more of the gene region target sequences listed in Tables 1-5, below. In certain exemplary embodiments, RNA silencing agents of the present application are capable of targeting transcripts of one or more of the target sequences listed at gene positions selected from the group consisting of 018, 028, 031, 048, 052, 056, 127, 129, 136, 143, 145, 148, 149, 150, 180, 182, 187, 191, 202, 211, 214, 215, 219, 226, 237, 241, 244, 250, 251, 272, 275, 282, 288, 291, 294, 305, and 306 of the human C9ORF72 gene. Particularly exemplary target sequences of the human C9ORF72 gene can be found at positions 241 (5' ACAAGAAAAGACCTGATAAAGAT-TAACCAGAAGAAAACAAGGAGG 3' (SEQ ID NO: 7)) and AS 241 (5' TCCCTCCTTGTTTTCTTCTGGT-TAATCTTTATCAGGTCTTTTCTT 3' (SEQ ID NO: 8)). Genomic sequence for each target sequence can be found in, for example, the publicly available database maintained by the NCBI.

Various aspects of the present application are described in further detail in the following subsections.

II. siRNA Design

In some embodiments, siRNAs are designed as follows. First, a portion of the target gene (e.g., the C9ORF72 gene), for example, one or more of the target sequences set forth at Tables 1-5 is selected. Cleavage of mRNA at these sites should eliminate translation of corresponding C9ORF72 protein or RAN peptides. Sense and antisense strands were designed based on the target sequence. (See Tables 1-5) In one embodiment, the portion (and corresponding sense or antisense strand) includes about 15-25 nucleotides. In another embodiment, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the present application provided that they retain the ability to mediate RNAi. Longer RNAi agents have been demonstrated to elicit an interferon or PKR response in certain mammalian cells which can be undesirable. In one embodiment, the RNAi agents of the present application do not elicit a PKR response (i.e., are of a sufficiently short length). However, longer RNAi agents can be useful, for example, in cell types incapable of generating a PKR response or in situations where the PKR response has been down-regulated or dampened by alternative means.

When the target gene is in the sense direction, the sense strand sequence is designed such that the target sequence is essentially in the middle of the strand. Moving the target sequence to an off-center position can, in some instances, reduce efficiency of cleavage by the siRNA. Such compositions, i.e., less efficient compositions, can be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2-, 3-, 4-, 5-, 6- or 7-nucleotide overhangs are generated, i.e., the 3' end of the sense strand extends 1, 2, 3, 4, 5, 6 or 7 nucleotides further than the 5' end of the antisense strand and/or the 3' end of the antisense strand extends 1, 2, 3, 4, 5, 6 or 7 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the present application, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the C9ORF72 target sequences set forth at Tables 1-5 are described in detail below. siRNAs can be designed according to the above exemplary teachings for any other target sequences found in the C9ORF72 gene. Moreover, the technology is applicable to targeting any other target sequences, e.g., non-disease-causing target sequences.

To validate the effectiveness by which siRNAs destroy mRNAs (e.g., C9ORF72 mRNA), the siRNA can be incubated with cDNA (e.g., C9ORF72 cDNA) in a *Drosophila*-based in vitro mRNA expression system. Radiolabeled with $^{32}P$, newly synthesized mRNAs (e.g., C9ORF72 mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

III. RNAi Agents

The present application includes siRNA molecules designed, for example, as described above. The siRNA molecules of the present application can be chemically synthesized, or can be transcribed in vitro from a DNA template, or in vivo from e.g., shRNA, or by using recombinant human DICER enzyme, to cleave in vitro transcribed dsRNA templates into pools of, for example, 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present application can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katand-in.cshl.org:9331/RNAi/docs/BseRI-BamHI_Strategy.pdf and katandin.cshl.org:9331/RNAi/docs/Web_version_of_PCR_strategyl.pdf).

Expression constructs of the present application include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (e.g., C9ORF72 genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct can contain multiple sequences coding for siRNAs, such as multiple regions of the gene encoding C9ORF72, targeting the same gene or multiple genes, and can be driven, for example, by separate PolIII promoter sites.

TABLE 1

C9ORF72 sequences for isoform-selective targeting (pre GGGGCC expansion) (Sense Direction)

| Oligo ID | Accession number | Gene region (45 nucleotides in length) | SEQ ID NO: |
|---|---|---|---|
| C9ORF72_018 | NM_145005.6, NM_001256054.2 | GTAACCTACGGTGTCCCGCTAGGAAAGAG AGGTGCGTCAAACAGC | 9 |
| C9ORF72_028 | NM_145005.6, NM_001256054.2 | GTGTCCCGCTAGGAAAGAGAGGTGCGTCA AACAGCGACAAGTTCC | 10 |
| C9ORF72_031 | NM_145005.6, NM_001256054.2 | TCCCGCTAGGAAAGAGAGGTGCGTCAAAC AGCGACAAGTTCCGCC | 11 |
| C9ORF72_035 | NM_145005.6, NM_001256054.2 | GCTAGGAAAGAGAGGTGCGTCAAACAGCG ACAAGTTCCGCCCACG | 12 |
| C9ORF72_048 | NM_145005.6, NM_001256054.2 | GGTGCGTCAAACAGCGACAAGTTCCGCCC ACGTAAAAGATGACGC | 13 |
| C9ORF72_052 | NM_145005.6, NM_001256054.2 | CGTCAAACAGCGACAAGTTCCGCCCACGT AAAAGATGACGCTTGG | 14 |
| C9ORF72_056 | NM_145005.6, NM_001256054.2 | AAACAGCGACAAGTTCCGCCCACGTAAAA GATGACGCTTGGTGTG | 15 |
| C9ORF72_127 | NM_001256054.2 | TCTCTTTTGGGGCGGGGTCTAGCAAGAG CAGGTGTGGGTTTAGG | 16 |
| C9ORF72_129 | NM_001256054.2 | TCTTTTGGGGCGGGGTCTAGCAAGAGCA GGTGTGGGTTTAGGAG | 17 |
| C9ORF72_136 | NM_001256054.2 | GGGGCGGGGTCTAGCAAGAGCAGGTGTGG GTTTAGGAGGTGTGTG | 18 |
| C9ORF72_143 | NM_001256054.2 | GGTCTAGCAAGAGCAGGTGTGGGTTTAGG AGGTGTGTGTTTTTGT | 19 |
| C9ORF72_148 | NM_001256054.2 | AGCAAGAGCAGGTGTGGGTTTAGGAGGTG TGTGTTTTTGTTTTTC | 20 |
| C9ORF72_149 | NM_001256054.2 | GCAAGAGCAGGTGTGGGTTTAGGAGGTGT GTGTTTTTGTTTTTCC | 21 |
| C9ORF72_150 | NM_001256054.2 | CAAGAGCAGGTGTGGGTTTAGGAGGTGTG TGTTTTTGTTTTTCCC | 22 |

TABLE 1-continued

C9ORF72 sequences for isoform-selective targeting (pre GGGGCC expansion) (Sense Direction)

| | | | |
|---|---|---|---|
| C9ORF72_180 | NG_031977.1 | GTTTTTGTTTTTCCCACCCTCTCTCCCCACTACTTGCTCTCACAG | 23 |
| C9ORF72_182 | NG_031977.1 | TTTTGTTTTTCCCACCCTCTCTCCCCACTACTTGCTCTCACAGTA | 24 |
| C9ORF72_187 | NG_031977.1 | TTTTTCCCACCCTCTCTCCCCACTACTTGCTCTCACAGTACTCGC | 25 |
| C9ORF72_191 | NG_031977.1 | TCCCACCCTCTCTCCCCACTACTTGCTCTCACAGTACTCGCTGAG | 26 |
| C9ORF72_202 | NG_031977.1 | CTCCCCACTACTTGCTCTCACAGTACTCGCTGAGGGTGAACAAGA | 27 |
| C9ORF72_211 | NG_031977.1 | ACTTGCTCTCACAGTACTCGCTGAGGGTGAACAAGAAAAGACCTG | 28 |
| C9ORF72_214 | NG_031977.1 | TGCTCTCACAGTACTCGCTGAGGGTGAACAAGAAAAGACCTGATA | 29 |
| C9ORF72_215 | NG_031977.1 | GCTCTCACAGTACTCGCTGAGGGTGAACAAGAAAAGACCTGATAA | 30 |
| C9ORF72_219 | NG_031977.1 | TCACAGTACTCGCTGAGGGTGAACAAGAAAAGACCTGATAAAGAT | 31 |
| C9ORF72_226 | NG_031977.1 | ACTCGCTGAGGGTGAACAAGAAAAGACCTGATAAAGATTAACCAG | 32 |
| C9ORF72_237 | NG_031977.1 | GTGAACAAGAAAAGACCTGATAAAGATTAACCAGAAGAAAACAAG | 33 |
| C9ORF72_243 | NG_031977.1 | AAGAAAAGACCTGATAAAGATTAACCAGAAGAAAACAAGGAGGGA | 34 |
| C9ORF72_244 | NG_031977.1 | AGAAAAGACCTGATAAAGATTAACCAGAAGAAAACAAGGAGGGAA | 35 |
| C9ORF72_250 | NG_031977.1 | GACCTGATAAAGATTAACCAGAAGAAAACAAGGAGGGAAACAACC | 36 |
| C9ORF72_251 | NG_031977.1 | ACCTGATAAAGATTAACCAGAAGAAAACAAGGAGGGAAACAACCG | 37 |
| C9ORF72_272 | NG_031977.1 | AGAAAACAAGGAGGGAAACAACCGCAGCCTGTAGCAAGCTCTGGA | 38 |
| C9ORF72_275 | NG_031977.1 | AAACAAGGAGGGAAACAACCGCAGCCTGTAGCAAGCTCTGGAACT | 39 |
| C9ORF72_282 | NG_031977.1 | GAGGGAAACAACCGCAGCCTGTAGCAAGCTCTGGAACTCAGGAGT | 40 |
| C9ORF72_288 | NG_031977.1 | AACAACCGCAGCCTGTAGCAAGCTCTGGAACTCAGGAGTCGCGCG | 41 |
| C9ORF72_291 | NG_031977.1 | AACCGCAGCCTGTAGCAAGCTCTGGAACTCAGGAGTCGCGCGCTA | 42 |
| C9ORF72_294 | NG_031977.1 | CGCAGCCTGTAGCAAGCTCTGGAACTCAGGAGTCGCGCGCTAGGG | 43 |
| C9ORF72_305 | NG_031977.1 | GCAAGCTCTGGAACTCAGGAGTCGCGCGCTAGGGGCCGGGGCCGG | 44 |
| C9ORF72_306 | NG_031977.1 | CAAGCTCTGGAACTCAGGAGTCGCGCGCTAGGGGCCGGGGCCGGG | 45 |

| Oligo ID | Targeted mRNA Sequence | SEQ ID NO: | Unmodified Guide Strands | SEQ ID NO: |
|---|---|---|---|---|
| C9ORF72_018 | CCGCUAGGAAAGAGAGGUGC | 46 | UCACCUCUCUUUCCUAGCGG | 81 |
| C9ORF72_028 | AGAGAGGUGCGUCAAACAGC | 47 | UCUGUUUGACGCACCUCUCU | 82 |

TABLE 1-continued

C9ORF72 sequences for isoform-selective targeting (pre GGGGCC expansion) (Sense Direction)

| | | | | |
|---|---|---|---|---|
| C9ORF72_031 | GAGGUGCGUCAAACAGCGAC | 48 | UUCGCUGUUUGACGCACCUC | 83 |
| C9ORF72_035 | UGCGUCAAACAGCGACAAGU | 49 | UCUUGUCGCUGUUUGACGCA | 84 |
| C9ORF72_048 | GACAAGUUCCGCCCACGUAA | 50 | UUACGUGGGCGGAACUUGUC | 85 |
| C9ORF72_052 | AGUUCCGCCCACGUAAAAGA | 51 | UCUUUUACGUGGGCGGAACU | 86 |
| C9ORF72_056 | CCGCCCACGUAAAAGAUGAC | 52 | UUCAUCUUUUACGUGGGCGG | 87 |
| C9ORF72_127 | GGGUCUAGCAAGAGCAGGUG | 53 | UACCUGCUCUUGCUAGACCC | 88 |
| C9ORF72_129 | GUCUAGCAAGAGCAGGUGUG | 54 | UACACCUGCUCUUGCUAGAC | 89 |
| C9ORF72_136 | AAGAGCAGGUGUGGGUUUAG | 55 | UUAAACCCACACCUGCUCUU | 90 |
| C9ORF72_143 | GGUGUGGGUUUAGGAGGUGU | 56 | UCACCUCCUAAACCCACACC | 91 |
| C9ORF72_148 | GGGUUUAGGAGGUGUGUGUU | 57 | UACACACCUCCUAAACCC | 92 |
| C9ORF72_149 | GGUUUAGGAGGUGUGUGUUU | 58 | UAACACACCUCCUAAACC | 93 |
| C9ORF72_150 | GUUUAGGAGGUGUGUGUUUU | 59 | UAAACACACCUCCUAAAC | 94 |
| C9ORF72_180 | ACCCUCUCUCCCCACUACUU | 60 | UAGUAGUGGGGAGAGAGGGU | 95 |
| C9ORF72_182 | CCUCUCUCCCCACUACUUGC | 61 | UCAAGUAGUGGGGAGAGAGG | 96 |
| C9ORF72_187 | CUCCCCACUACUUGCUCUCA | 62 | UGAGAGCAAGUAGUGGGGAG | 97 |
| C9ORF72_191 | CCACUACUUGCUCUCACAGU | 63 | UCUGUGAGAGCAAGUAGUGG | 98 |
| C9ORF72_202 | UCUCACAGUACUCGCUGAGG | 64 | UCUCAGCGAGUACUGUGAGA | 99 |
| C9ORF72_211 | ACUCGCUGAGGGUGAACAAG | 65 | UUUGUUCACCCUCAGCGAGU | 100 |
| C9ORF72_214 | CGCUGAGGGUGAACAAGAAA | 66 | UUUCUUGUUCACCCUCAGCG | 101 |
| C9ORF72_215 | GCUGAGGGUGAACAAGAAAA | 67 | UUUUCUUGUUCACCCUCAGC | 102 |
| C9ORF72_219 | AGGGUGAACAAGAAAAGACC | 68 | UGUCUUUUCUUGUUCACCCU | 103 |
| C9ORF72_226 | ACAAGAAAAGACCUGAUAAA | 69 | UUUAUCAGGUCUUUUCUUGU | 104 |
| C9ORF72_237 | CCUGAUAAAGAUUAACCAGA | 70 | UCUGGUUAAUCUUUAUCAGG | 105 |
| C9ORF72_244 | AAGAUUAACCAGAAGAAAAC | 4 | UUUUUCUUCUGGUUAAUCUU | 106 |
| C9ORF72_250 | AACCAGAAGAAAACAAGGAG | 71 | UUCCUUGUUUUCUUCUGGUU | 107 |
| C9ORF72_251 | ACCAGAAGAAAACAAGGAGG | 72 | UCUCCUUGUUUUCUUCUGGU | 108 |

TABLE 1-continued

C9ORF72 sequences for isoform-selective targeting (pre GGGGCC expansion) (Sense Direction)

| Oligo ID | Sequence | SEQ ID NO | Antisense | SEQ ID NO |
|---|---|---|---|---|
| C9ORF72_272 | AAACAACCGCAGCCUGUAGC | 73 | UCUACAGGCUGCGGUUGUUU | 109 |
| C9ORF72_275 | CAACCGCAGCCUGUAGCAAG | 74 | UUUGCUACAGGCUGCGGUUG | 110 |
| C9ORF72_282 | AGCCUGUAGCAAGCUCUGGA | 75 | UCCAGAGCUUGCUACAGGCU | 111 |
| C9ORF72_288 | UAGCAAGCUCUGGAACUCAG | 76 | UUGAGUUCCAGAGCUUGCUA | 112 |
| C9ORF72_291 | CAAGCUCUGGAACUCAGGAG | 77 | UUCCUGAGUUCCAGAGCUUG | 113 |
| C9ORF72_294 | GCUCUGGAACUCAGGAGUCG | 78 | UGACUCCUGAGUUCCAGAGC | 114 |
| C9ORF72_305 | CAGGAGUCGCGCGCUAGGGG | 79 | UCCCUAGCGCGCGACUCCUG | 115 |
| C9ORF72_306 | AGGAGUCGCGCGCUAGGGGC | 80 | UCCCCUAGCGCGCGACUCCU | 116 |

| Oligo ID | Modified Sequence | SEQ ID NO: |
|---|---|---|
| C9ORF72_018 | P(mU)#(fC)#(mA)(fC)(fC)(fU)(mC)(fU)(mC)(fU)(mU)(fU)(mC)#(fC)#(mU)#(fA)#(mG)#(mC)#(mG) | 117 |
| C9ORF72_028 | P(mU)#(fC)#(mU)(fG)(fU)(mU)(fG)(mA)(fC)(mG)(fC)(mA)#(fC)#(mC)#(fU)#(mC)#(mU)#(mC)#(fU) | 118 |
| C9ORF72_031 | P(mU)#(fU)#(mC)(fG)(fC)(fU)(mG)(fU)(mU)(fU)(mG)(fA)(mC)#(fG)#(mC)#(fA)#(mC)#(mC)#(mU)#(fC) | 119 |
| C9ORF72_035 | P(mU)#(fC)#(mU)(fU)(fG)(fU)(mC)(fG)(mC)(fU)(mG)(fU)(mU)#(fU)#(mG)#(fA)#(mC)#(mG)#(mC)#(fA) | 120 |
| C9ORF72_048 | P(mU)#(fU)#(mA)(fC)(fG)(fU)(mG)(fG)(mG)(fC)(mG)(fG)(mA)#(fA)#(mC)#(fU)#(mU)#(mG)#(mU)#(fC) | 121 |
| C9ORF72_052 | P(mU)#(fC)#(mU)(fU)(fU)(fU)(mA)(fC)(mG)(fU)(mG)(fG)(mG)#(fC)#(mG)#(fG)#(mA)#(mA)#(mC)#(fU) | 122 |
| C9ORF72_056 | P(mU)#(fU)#(mC)(fA)(fU)(fC)(mU)(fU)(mU)(fU)(mA)(fC)(mG)#(fU)#(mG)#(fG)#(mG)#(mC)#(mG)#(fG) | 123 |
| C9ORF72_127 | P(mU)#(fA)#(mC)(fC)(fU)(fG)(mC)(fU)(mC)(fU)(mU)(fG)(mC)#(fU)#(mA)#(fG)#(mA)#(mC)#(mC)#(fC) | 124 |
| C9ORF72_129 | P(mU)#(fA)#(mC)(fA)(fC)(fC)(mU)(fG)(mC)(fU)(mC)(fU)(mU)(fG)#(mC)#(fU)#(mA)#(mG)#(mA)#(fC) | 125 |
| C9ORF72_136 | P(mU)#(fU)#(mA)(fA)(fA)(fC)(mC)(fC)(mA)(fC)(mA)(fC)(mC)#(fU)#(mG)#(fC)#(mU)#(mC)#(mU)#(fU) | 126 |
| C9ORF72_143 | P(mU)#(fC)#(mA)(fC)(fC)(fU)(mC)(fC)(mU)(fA)(mA)(fA)(mC)#(fC)#(mC)#(fA)#(mC)#(mA)#(mC)#(fC) | 127 |
| C9ORF72_148 | P(mU)#(fA)#(mC)(fA)(fC)(fA)(mC)(fA)(mC)(fC)(mU)(fC)(mC)#(fU)#(mA)#(fA)#(mA)#(mC)#(mC)#(fC) | 128 |
| C9ORF72_149 | P(mU)#(fA)#(mA)(fC)(fA)(fC)(mA)(fC)(mA)(fC)(mC)(fU)(mC)#(fC)#(mU)#(fA)#(mA)#(mA)#(mC)#(fC) | 129 |
| C9ORF72_150 | P(mU)#(fA)#(mA)(fA)(fC)(fA)(mC)(fA)(mC)(fA)(mC)(fC)(mU)#(fC)#(mC)#(fU)#(mA)#(mA)#(mA)#(fC) | 130 |
| C9ORF72_180 | P(mU)#(fA)#(mG)(fU)(fA)(fG)(mU)(fG)(mG)(fG)(mG)(fA)(mG)#(fA)#(mG)#(fA)#(mG)#(mG)#(mG)#(fU) | 131 |
| C9ORF72_182 | P(mU)#(fC)#(mA)(fA)(fG)(fU)(mA)(fG)(mU)(fG)(mG)(fG)(mG)#(fA)#(mG)#(fA)#(mG)#(mA)#(mG)#(fG) | 132 |
| C9ORF72_187 | P(mU)#(fG)#(mA)(fG)(fA)(fG)(mC)(fA)(mA)(fG)(mU)(fA)(mG)#(fU)#(mG)#(fG)#(mG)#(mG)#(mA)#(fG) | 133 |

TABLE 1-continued

C9ORF72 sequences for isoform-selective targeting (pre GGGGCC expansion) (Sense Direction)

| | |
|---|---|
| C9ORF72_191 P(mU)#(fC)#(mU)(fG)(fU)(fG)(mA)(fG)(mA)(fG)(mC)(fA)(mA)#(fG)#(mU)#(fA)#(mG)#(mU)#(mG)#(fG) | 134 |
| C9ORF72_202 P(mU)#(fC)#(mU)(fC)(fA)(fG)(mC)(fG)(mA)(fG)(mU)(fA)(mC)#(fU)#(mG)#(fU)#(mG)#(mA)#(mG)#(fA) | 135 |
| C9ORF72_211 P(mU)#(fU)#(mU)(fG)(fU)(fU)(mC)(fA)(mC)(fC)(mC)(fU)(mC)#(fA)#(mG)#(fC)#(mG)#(mA)#(mG)#(fU) | 136 |
| C9ORF72_214 P(mU)#(fU)#(mU)(fC)(fU)(fU)(mG)(fU)(mU)(fC)(mA)(fC)(mC)#(fC)#(mU)#(fC)#(mA)#(mG)#(mC)#(fG) | 137 |
| C9ORF72_215 P(mU)#(fU)#(mU)(fU)(fC)(fU)(mU)(fG)(mU)(fU)(mC)(fA)(mC)#(fC)#(mC)#(fU)#(mC)#(mA)#(mG)#(fC) | 138 |
| C9ORF72_219 P(mU)#(fG)#(mU)(fC)(fU)(fU)(mU)(fU)(mC)(fU)(mU)(fG)(mU)#(fU)#(mC)#(fA)#(mC)#(mC)#(mC)#(fU) | 139 |
| C9ORF72_226 P(mU)#(fU)#(mU)(fA)(fU)(fC)(mA)(fG)(mG)(fU)(mC)(fU)(mU)#(fU)#(mU)#(fC)#(mU)#(mU)#(mG)#(fU) | 140 |
| C9ORF72_237 P(mU)#(fC)#(mU)(fG)(fG)(fU)(mU)(fA)(mA)(fU)(mC)(fU)(mU)#(fU)#(mA)#(fU)#(mC)#(mA)#(mG)#(fG) | 141 |
| C9ORF72_244 P(mU)#(fU)#(mU)(fU)(fU)(fC)(mU)(fU)(mU)(fC)(mU)(fG)(mG)#(fU)#(mA)#(fA)#(mU)#(mC)#(mU)#(fU) | 142 |
| C9ORF72_250 P(mU)#(fU)#(mC)(fC)(fU)(fU)(mG)(fU)(mU)(fU)(mU)(fC)(mU)#(fU)#(mC)#(fU)#(mG)#(mG)#(mU)#(fU) | 143 |
| C9ORF72_251 P(mU)#(fC)#(mU)(fC)(fC)(fU)(mU)(fG)(mU)(fU)(mU)(fU)(mC)#(fU)#(mU)#(fC)#(mU)#(mG)#(mG)#(fU) | 144 |
| C9ORF72_272 P(mU)#(fC)#(mU)(fA)(fC)(fA)(mG)(fG)(mC)(fU)(mG)(fC)(mG)#(fG)#(mU)#(fU)#(mG)#(mU)#(mU)#(fU) | 145 |
| C9ORF72_275 P(mU)#(fU)#(mU)(fG)(fC)(fU)(mA)(fC)(mA)(fG)(mG)(fC)(mU)#(fG)#(mC)#(fG)#(mG)#(mU)#(mU)#(fG) | 146 |
| C9ORF72_282 P(mU)#(fC)#(mC)(fA)(fG)(fA)(mG)(fC)(mU)(fU)(mG)(fC)(mU)#(fA)#(mC)#(fA)#(mG)#(mG)#(mC)#(fU) | 147 |
| C9ORF72_288 P(mU)#(fU)#(mG)(fA)(fG)(fU)(mU)(fC)(mC)(fA)(mG)(fA)(mG)#(fC)#(mU)#(fU)#(mG)#(mC)#(mU)#(fA) | 148 |
| C9ORF72_291 P(mU)#(fU)#(mC)(fC)(fU)(fG)(mA)(fG)(mU)(fU)(mC)(fC)(mA)#(fG)#(mA)#(fG)#(mC)#(mU)#(mU)#(fG) | 149 |
| C9ORF72_294 P(mU)#(fG)#(mA)(fC)(fU)(fC)(mC)(fU)(mG)(fA)(mG)(fU)(mU)#(fC)#(mC)#(fA)#(mG)#(mA)#(mG)#(fC) | 150 |
| C9ORF72_305 P(mU)#(fC)#(mC)(fC)(fU)(fA)(mG)(fC)(mG)(fC)(mG)(fA)#(mC)#(fU)#(mC)#(mC)#(mU)#(fG) | 151 |
| C9ORF72_306 P(mU)#(fC)#(mC)(fC)(fC)(fU)(mA)(fG)(mC)(fG)(mC)(fG)(mC)#(fG)#(mA)#(fC)#(mU)#(mC)#(mC)#(fU) | 152 |

TABLE 2

C9ORF72 sequences for isoform-selective targeting (pre GGGGCC expansion) (Antisense Direction)

| Oligo ID | Gene region | SEQ ID NO: |
|---|---|---|
| C9ORF72_AS_018 | GTAACCTACGGTGTCCCGCTAGGAAAGAGAGGTGCGTCAAACAGC | 9 |
| C9ORF72_AS_028 | GTGTCCCGCTAGGAAAGAGAGGTGCGTCAAACAGCGACAAGTTCC | 10 |
| C9ORF72_AS_031 | TCCCGCTAGGAAAGAGAGGTGCGTCAAACAGCGACAAGTTCCGCC | 11 |
| C9ORF72_AS_035 | GCTAGGAAAGAGAGGTGCGTCAAACAGCGACAAGTTCCGCCCACG | 12 |
| C9ORF72_AS_048 | GGTGCGTCAAACAGCGACAAGTTCCGCCCACGTAAAAGATGACGC | 13 |

TABLE 2-continued

C9ORF72 sequences for isoform-selective targeting (pre GGGGCC expansion) (Antisense Direction)

| Oligo ID | Sequence | SEQ ID NO: |
|---|---|---|
| C9ORF72_AS_052 | CGTCAAACAGCGACAAGTTCCGCCCACGTAAAAGATGACGCTTGG | 14 |
| C9ORF72_AS_056 | AAACAGCGACAAGTTCCGCCCACGTAAAAGATGACGCTTGGTGTG | 15 |
| C9ORF72_AS_127 | TCTCTTTTGGGGCGGGGTCTAGCAAGAGCAGGTGTGGGTTTAGG | 16 |
| C9ORF72_AS_129 | TCTTTTGGGGCGGGGTCTAGCAAGAGCAGGTGTGGGTTTAGGAG | 17 |
| C9ORF72_AS_136 | GGGGCGGGGTCTAGCAAGAGCAGGTGTGGGTTTAGGAGGTGTGTG | 18 |
| C9ORF72_AS_143 | GGTCTAGCAAGAGCAGGTGTGGGTTTAGGAGGTGTGTGTTTTTGT | 19 |
| C9ORF72_AS_145 | TCTAGCAAGAGCAGGTGTGGGTTTAGGAGGTGTGTGTTTTTGTTT | 20 |
| C9ORF72_AS_148 | AGCAAGAGCAGGTGTGGGTTTAGGAGGTGTGTGTTTTTGTTTTTC | 21 |
| C9ORF72_AS_149 | GCAAGAGCAGGTGTGGGTTTAGGAGGTGTGTGTTTTTGTTTTTCC | 22 |
| C9ORF72_AS_150 | CAAGAGCAGGTGTGGGTTTAGGAGGTGTGTGTTTTTGTTTTTCCC | 23 |
| C9ORF72_AS_180 | GTTTTTGTTTTTCCCACCCTCTCTCCCCACTACTTGCTCTCACAG | 24 |
| C9ORF72_AS_182 | TTTTGTTTTTCCCACCCTCTCTCCCCACTACTTGCTCTCACAGTA | 25 |
| C9ORF72_AS_187 | TTTTTCCCACCCTCTCTCCCCACTACTTGCTCTCACAGTACTCGC | 26 |
| C9ORF72_AS_191 | TCCCACCCTCTCTCCCCACTACTTGCTCTCACAGTACTCGCTGAG | 27 |
| C9ORF72_AS_202 | CTCCCCACTACTTGCTCTCACAGTACTCGCTGAGGGTGAACAAGA | 28 |
| C9ORF72_AS_211 | ACTTGCTCTCACAGTACTCGCTGAGGGTGAACAAGAAAAGACCTG | 29 |
| C9ORF72_AS_214 | TGCTCTCACAGTACTCGCTGAGGGTGAACAAGAAAAGACCTGATA | 30 |
| C9ORF72_AS_215 | GCTCTCACAGTACTCGCTGAGGGTGAACAAGAAAAGACCTGATAA | 31 |
| C9ORF72_AS_219 | TCACAGTACTCGCTGAGGGTGAACAAGAAAAGACCTGATAAAGAT | 32 |
| C9ORF72_AS_226 | ACTCGCTGAGGGTGAACAAGAAAAGACCTGATAAAGATTAACCAG | 33 |
| C9ORF72_AS_237 | GTGAACAAGAAAAGACCTGATAAAGATTAACCAGAAGAAACAAG | 34 |
| C9ORF72_AS_244 | AGAAAGACCTGATAAAGATTAACCAGAAGAAAACAAGGAGGGAA | 35 |
| C9ORF72_AS_250 | GACCTGATAAAGATTAACCAGAAGAAAACAAGGAGGGAAACAACC | 36 |
| C9ORF72_AS_251 | ACCTGATAAAGATTAACCAGAAGAAAACAAGGAGGGAAACAACCG | 37 |
| C9ORF72_AS_272 | AGAAAACAAGGAGGGAAACAACCGCAGCCTGTAGCAAGCTCTGGA | 38 |
| C9ORF72_AS_275 | AAACAAGGAGGGAAACAACCGCAGCCTGTAGCAAGCTCTGGAACT | 39 |
| C9ORF72_AS_282 | GAGGGAAACAACCGCAGCCTGTAGCAAGCTCTGGAACTCAGGAGT | 40 |
| C9ORF72_AS_288 | AACAACCGCAGCCTGTAGCAAGCTCTGGAACTCAGGAGTCGCGCG | 41 |
| C9ORF72_AS_291 | AACCGCAGCCTGTAGCAAGCTCTGGAACTCAGGAGTCGCGCGCTA | 42 |
| C9ORF72_AS_294 | CGCAGCCTGTAGCAAGCTCTGGAACTCAGGAGTCGCGCGCTAGGG | 43 |
| C9ORF72_AS_305 | GCAAGCTCTGGAACTCAGGAGTCGCGCGCTAGGGGCCGGGGCCGG | 44 |
| C9ORF72_AS_306 | CAAGCTCTGGAACTCAGGAGTCGCGCGCTAGGGGCCGGGCCGGG | 45 |

| Oligo ID | Targeted Antisense mRNA Sequence | SEQ ID NO: | Unmodified Guide Strands | SEQ ID NO: |
|---|---|---|---|---|
| C9ORF72_AS_018 | GCACCUCUCUUUCCUAGCGA | 154 | UCGCUAGGAAAGAGAGGUGC | 189 |
| C9ORF72_AS_028 | GCUGUUUGACGCACCUCUCA | 155 | UGAGAGGUGCGUCAAACAGC | 190 |
| C9ORF72_AS_031 | GUCGCUGUUUGACGCACCUA | 156 | UAGGUGCGUCAAACAGCGAC | 191 |
| C9ORF72_AS_035 | ACUUGUCGCUGUUUGACGCA | 157 | UGCGUCAAACAGCGACAAGU | 49 |
| C9ORF72_AS_048 | UUACGUGGGCGGAACUUGUA | 158 | UACAAGUUCCGCCCACGUAA | 192 |

TABLE 2-continued

C9ORF72 sequences for isoform-selective targeting (pre GGGGCC expansion) (Antisense Direction)

| Oligo ID | Sequence | SEQ ID NO: | Sequence | SEQ ID NO: |
|---|---|---|---|---|
| C9ORF72_AS_052 | UCUUUUACGUGGGCGGAACA | 159 | UGUUCCGCCCACGUAAAAGA | 193 |
| C9ORF72_AS_056 | GUCAUCUUUUACGUGGGCGA | 160 | UCGCCCACGUAAAAGAUGAC | 194 |
| C9ORF72_AS_127 | CACCUGCUCUUGCUAGACCA | 161 | UGGUCUAGCAAGAGCAGGUG | 195 |
| C9ORF72_AS_129 | CACACCUGCUCUUGCUAGAA | 162 | UUCUAGCAAGAGCAGGUGUG | 196 |
| C9ORF72_AS_136 | CUAAACCCACACCUGCUCUA | 163 | UAGAGCAGGUGUGGGUUUAG | 197 |
| C9ORF72_AS_143 | ACACCUCCUAAACCCACACA | 164 | UGUGUGGGUUUAGGAGGUGU | 198 |
| C9ORF72_AS_148 | AACACACACCUCCUAAACCA | 165 | UGGUUUAGGAGGUGUGUGUU | 199 |
| C9ORF72_AS_149 | AAACACACACCUCCUAAACA | 166 | UGUUUAGGAGGUGUGUGUUU | 200 |
| C9ORF72_AS_150 | AAAACACACACCUCCUAAAA | 167 | UUUUAGGAGGUGUGUGUUUU | 201 |
| C9ORF72_AS_180 | AAGUAGUGGGGAGAGAGGGA | 168 | UCCCUCUCUCCCCACUACUU | 202 |
| C9ORF72_AS_182 | GCAAGUAGUGGGGAGAGAGA | 169 | UCUCUCUCCCCACUACUUGC | 203 |
| C9ORF72_AS_187 | UGAGAGCAAGUAGUGGGGAA | 170 | UUCCCCACUACUUGCUCUCA | 204 |
| C9ORF72_AS_191 | ACUGUGAGAGCAAGUAGUGA | 171 | UCACUACUUGCUCUCACAGU | 205 |
| C9ORF72_AS_202 | CCUCAGCGAGUACUGUGAGA | 172 | UCUCACAGUACUCGCUGAGG | 64 |
| C9ORF72_AS_211 | CUUGUUCACCCUCAGCGAGA | 173 | UCUCGCUGAGGGUGAACAAG | 206 |
| C9ORF72_AS_214 | UUUCUUGUUCACCCUCAGCA | 174 | UGCUGAGGGUGAACAAGAAA | 207 |
| C9ORF72_AS_215 | UUUUCUUGUUCACCCUCAGA | 175 | UCUGAGGGUGAACAAGAAAA | 208 |
| C9ORF72_AS_219 | GGUCUUUUCUUGUUCACCCA | 176 | UGGGUGAACAAGAAAAGACC | 209 |
| C9ORF72_AS_226 | UUUAUCAGGUCUUUUCUUGA | 177 | UCAAGAAAAGACCUGAUAAA | 210 |
| C9ORF72_AS_237 | UCUGGUUAAUCUUUAUCAGA | 178 | UCUGAUAAAGAUUAACCAGA | 211 |
| C9ORF72_AS_244 | GUUUCUUCUGGUUAAUCUA | 5 | UAGAUUAACCAGAAGAAAAC | 212 |
| C9ORF72_AS_250 | CUCCUUGUUUUCUUCUGGUA | 179 | UACCAGAAGAAAACAAGGAG | 213 |
| C9ORF72_AS_251 | CCUCCUUGUUUUCUUCUGGA | 180 | UCCAGAAGAAAACAAGGAGG | 214 |
| C9ORF72_AS_272 | GCUACAGGCUGCGGUUGUUA | 181 | UAACAACCGCAGCCUGUAGC | 215 |
| C9ORF72_AS_275 | CUUGCUACAGGCUGCGGUUA | 182 | UAACCGCAGCCUGUAGCAAG | 216 |
| C9ORF72_AS_282 | UCCAGAGCUUGCUACAGGCA | 183 | UGCCUGUAGCAAGCUCUGGA | 217 |
| C9ORF72_AS_288 | CUGAGUUCCAGAGCUUGCUA | 184 | UAGCAAGCUCUGGAACUCAG | 76 |
| C9ORF72_AS_291 | CUCCUGAGUUCCAGAGCUUA | 185 | UAAGCUCUGGAACUCAGGAG | 218 |
| C9ORF72_AS_294 | CGACUCCUGAGUUCCAGAGA | 186 | UCUCUGGAACUCAGGAGUCG | 219 |
| C9ORF72_AS_305 | CCCCUAGCGCGCGACUCCUA | 187 | UAGGAGUCGCGCGCUAGGGG | 220 |
| C9ORF72_AS_306 | GCCCCUAGCGCGCGACUCCA | 188 | UGGAGUCGCGCGCUAGGGGC | 221 |

| Oligo ID | Modified Sequence | SEQ ID NO: |
|---|---|---|
| C9ORF72_AS_018 | P(mU)#(fC)#(mG)(fC)(mU)(fA)(mG)(fG)(mA)(fA)(mA)(fG)(mA)#(fG)#(mA)#(fG)#(mG)#(fU)#(mG)#(mC) | 222 |
| C9ORF72_AS_028 | P(mU)#(fG)#(mA)(fG)(mA)(fG)(mG)(fU)(mG)(fC)(mG)(fU)(mC)#(fA)#(mA)#(fA)#(mC)#(fA)#(mG)#(mC) | 223 |
| C9ORF72_AS_031 | P(mU)#(fA)#(mG)(fG)(mU)(fG)(mC)(fG)(mU)(fC)(mA)(fA)(mA)#(fC)#(mA)#(fG)#(mC)#(fG)#(mA)#(mC) | 224 |
| C9ORF72_AS_035 | P(mU)#(fG)#(mC)(fG)(mU)(fC)(mA)(fA)(mA)(fC)(mA)(fG)(mC)#(fG)#(mA)#(fC)#(mA)#(fA)#(mG)#(mU) | 225 |

TABLE 2-continued

C9ORF72 sequences for isoform-selective targeting (pre GGGGCC expansion) (Antisense Direction)

| | | |
|---|---|---|
| C9ORF72_AS_048 | P(mU)#(fA)#(mC)(fA)(mA)(fG)(mU)(fU)(mC)(fC)(mG)(fC)(mC)#(fC)#(mA)#(fC)#(mG)#(fU)#(mA)#(mA) | 226 |
| C9ORF72_AS_052 | P(mU)#(fG)#(mU)(fU)(mC)(fC)(mG)(fC)(mC)(fC)(mA)(fC)(mG)#(fU)#(mA)#(fA)#(mA)#(fA)#(mG)#(mA) | 227 |
| C9ORF72_AS_056 | P(mU)#(fC)#(mG)(fC)(mC)(fC)(mA)(fC)(mG)(fU)(mA)(fA)(mA)#(fA)#(mG)#(fA)#(mU)#(fG)#(mA)#(mC) | 228 |
| C9ORF72_AS_127 | P(mU)#(fG)#(mG)(fU)(mC)(fU)(mA)(fG)(mC)(fA)(mA)(fG)(mA)#(fG)#(mC)#(fA)#(mG)#(fG)#(mU)#(mG) | 229 |
| C9ORF72_AS_129 | P(mU)#(fU)#(mC)(fU)(mA)(fG)(mC)(fA)(mA)(fG)(mA)(fG)(mC)#(fA)#(mG)#(fG)#(mU)#(fG)#(mU)#(mG) | 230 |
| C9ORF72_AS_136 | P(mU)#(fA)#(mG)(fA)(mG)(fC)(mA)(fG)(mG)(fU)(mG)(fU)(mG)#(fG)#(mG)#(fU)#(mU)#(fU)#(mA)#(mG) | 231 |
| C9ORF72_AS_143 | P(mU)#(fG)#(mU)(fG)(mU)(fG)(mG)(fG)(mU)(fU)(mU)(fA)(mG)#(fG)#(mA)#(fG)#(mG)#(fU)#(mG)#(mU) | 232 |
| C9ORF72_AS_148 | P(mU)#(fG)#(mG)(fU)(mU)(fU)(mA)(fG)(mG)(fA)(mG)(fG)(mU)#(fG)#(mU)#(fG)#(mU)#(fG)#(mU)#(mU) | 233 |
| C9ORF72_AS_149 | P(mU)#(fG)#(mU)(fU)(mU)(fA)(mG)(fG)(mA)(fG)(mG)(fU)(mG)#(fU)#(mG)#(fU)#(mG)#(fU)#(mU)#(mU) | 234 |
| C9ORF72_AS_150 | P(mU)#(fU)#(mU)(fU)(mA)(fG)(mG)(fA)(mG)(fG)(mU)(fG)(mU)#(fG)#(mU)#(fG)#(mU)#(fU)#(mU)#(mU) | 235 |
| C9ORF72_AS_180 | P(mU)#(fC)#(mC)(fC)(mU)(fC)(mU)(fC)(mU)(fC)(mC)(fC)(mC)#(fA)#(mC)#(fU)#(mA)#(fC)#(mU)#(mU) | 236 |
| C9ORF72_AS_182 | P(mU)#(fC)#(mU)(fC)(mU)(fC)(mU)(fC)(mC)(fC)(mC)(fA)(mC)#(fU)#(mA)#(fC)#(mU)#(fU)#(mG)#(mC) | 237 |
| C9ORF72_AS_187 | P(mU)#(fU)#(mC)(fC)(mC)(fC)(mA)(fC)(mU)(fA)(mC)(fU)(mU)#(fG)#(mC)#(fU)#(mC)#(fU)#(mC)#(mA) | 238 |
| C9ORF72_AS_191 | P(mU)#(fC)#(mA)(fC)(mU)(fA)(mC)(fU)(mU)(fG)(mC)(fU)(mC)#(fU)#(mC)#(fA)#(mC)#(fA)#(mG)#(mU) | 239 |
| C9ORF72_AS_202 | P(mU)#(fC)#(mU)(fC)(mA)(fC)(mA)(fG)(mU)(fA)(mC)(fU)(mC)#(fG)#(mC)#(fU)#(mG)#(fA)#(mG)#(mG) | 240 |
| C9ORF72_AS_211 | P(mU)#(fC)#(mU)(fC)(mG)(fC)(mU)(fG)(mA)(fG)(mG)(fG)(mU)#(fG)#(mA)#(fA)#(mC)#(fA)#(mA)#(mG) | 241 |
| C9ORF72_AS_214 | P(mU)#(fG)#(mC)(fU)(mG)(fA)(mG)(fG)(mG)(fU)(mG)(fA)(mA)#(fC)#(mA)#(fA)#(mG)#(fA)#(mA)#(mA) | 242 |
| C9ORF72_AS_215 | P(mU)#(fC)#(mU)(fG)(mA)(fG)(mG)(fG)(mU)(fG)(mA)(fA)(mC)#(fA)#(mA)#(fG)#(mA)#(fA)#(mA)#(mA) | 243 |
| C9ORF72_AS_219 | P(mU)#(fG)#(mG)(fG)(mU)(fG)(mA)(fA)(mC)(fA)(mA)(fG)(mA)#(fA)#(mA)#(fA)#(mG)#(fA)#(mC)#(mC) | 244 |
| C9ORF72_AS_226 | P(mU)#(fC)#(mA)(fA)(mG)(fA)(mA)(fA)(mA)(fG)(mA)(fC)(mC)#(fU)#(mG)#(fA)#(mU)#(fA)#(mA)#(mA) | 245 |
| C9ORF72_AS_237 | P(mU)#(fC)#(mU)(fG)(mA)(fU)(mA)(fA)(mA)(fG)(mA)(fU)(mU)#(fA)#(mA)#(fC)#(mC)#(fA)#(mG)#(mA) | 246 |
| C9ORF72_AS_241 | VP(mU)#(fU)#(mC)(fU)(mU)(fC)(mU)(fG)(mG)(fU)(mU)(fA)(mA)#(fU)#(mC)#(mU)#(mU)#(mA)#(fU) | 247 |
| C9ORF72_AS_244 | P(mU)#(fA)#(mG)(fA)(mU)(fU)(mA)(fA)(mC)(fC)(mA)(fG)(mA)#(fA)#(mG)#(fA)#(mA)#(fA)#(mA)#(mC) | 248 |
| C9ORF72_AS_250 | P(mU)#(fA)#(mC)(fC)(mA)(fG)(mA)(fA)(mG)(fA)(mA)(fA)(mA)#(fC)#(mA)#(fA)#(mG)#(fG)#(mA)#(mG) | 249 |
| C9ORF72_AS_251 | P(mU)#(fC)#(mC)(fA)(mG)(fA)(mA)(fG)(mA)(fA)(mA)(fA)(mC)#(fA)#(mA)#(fG)#(mG)#(fA)#(mG)#(mG) | 250 |
| C9ORF72_AS_272 | P(mU)#(fA)#(mA)(fC)(mA)(fA)(mC)(fC)(mG)(fC)(mA)(fG)(mC)#(fC)#(mU)#(fG)#(mU)#(fA)#(mG)#(mC) | 251 |

TABLE 2-continued

C9ORF72 sequences for isoform-selective targeting (pre GGGGCC expansion) (Antisense Direction)

C9ORF72_AS_275  P(mU)#(fA)#(mA)(fC)(mC)(fG)(mC)(fA)(mG)(fC)(mC)(fU)(mG)   252
                #(fU)#(mA)#(fG)#(mC)#(fA)#(mA)#(mG)

C9ORF72_AS_282  P(mU)#(fG)#(mC)(fC)(mU)(fG)(mU)(fA)(mG)(fC)(mA)(fA)(mG)   253
                #(fC)#(mU)#(fC)#(mU)#(fG)#(mG)#(mA)

C9ORF72_AS_288  P(mU)#(fA)#(mG)(fC)(mA)(fA)(mG)(fC)(mU)(fC)(mU)(fG)(mG)   254
                #(fA)#(mA)#(fC)#(mU)#(fC)#(mA)#(mG)

C9ORF72_AS_291  P(mU)#(fA)#(mA)(fG)(mC)(fU)(mC)(fU)(mG)(fG)(mA)(fA)(mC)   255
                #(fU)#(mC)#(fA)#(mG)#(fG)#(mA)#(mG)

C9ORF72_AS_294  P(mU)#(fC)#(mU)(fC)(mU)(fG)(mG)(fA)(mA)(fC)(mU)(fC)(mA)   256
                #(fG)#(mG)#(fA)#(mG)#(fU)#(mC)#(mG)

C9ORF72_AS_305  P(mU)#(fA)#(mG)(fG)(mA)(fG)(mU)(fC)(mG)(fC)(mG)(fC)(mG)   257
                #(fC)#(mU)#(fA)#(mG)#(fG)#(mG)#(mG)

C9ORF72_AS_306  P(mU)#(fG)#(mG)(fA)(mG)(fU)(mC)(fG)(mC)(fG)(mC)(fG)(mC)   258
                #(fU)#(mA)#(fG)#(mG)#(fG)#(mG)#(mC)

TABLE 3

C9ORF72 sequences for selective targeting (Post GGGGCC expansion) (Sense Direction)

| Oligo ID | Accession number | Gene region | SEQ ID NO: |
| --- | --- | --- | --- |
| C9ORF72_541 | NC_000009.12 | GCTCGACGCATTTTTACTTTCCCTCTCATTTCTCT GACCGAAGCT | 259 |
| C9ORF72_1056 | NC_000009.12 | AGATGACACAGACTTGCTTAAAGGAAGTGACTA TTGTGACTTGGG | 260 |
| C9ORF72_1116 | NC_000009.12 | GGTAATCAGTTGTCTAAAGAAGTGCACAGATTA CATGTCCGTGTG | 261 |
| C9ORF72_1283 | NC_000009.12 | GGGAGAGTAGTTGCCTGGTTGTGGCAGTTGGTA AATTTCTATTCA | 262 |
| C9ORF72_1375 | NC_000009.12 | CTGGCATTACTTCTACTTTTGTACAAAGGATCAA AAAAAAAAAG | 263 |
| C9ORF72_1847 | NC_000009.12 | TCTACGTTAATTAGATAGTTCCCAGGAGGACTAG GTTAGCCTACC | 264 |
| C9ORF72_2065 | NC_000009.12 | TTTAGGATCCTGCTTCTCTTTGGGCTGGGAGAA AATAAACAGCAT | 265 |
| C9ORF72_2782 | NC_000009.12 | TGAGCTGATTTTTTTCAGCTGCATTTGCATGTAT GGATTTTTCTC | 266 |
| C9ORF72_2802 | NC_000009.12 | GCATTTGCATGTATGGATTTTTCTCACCAAAGAC GATGACTTCAA | 267 |
| C9ORF72_3401 | NC_000009.12 | TTGCTCCAGGGTTCAGTTCTGTTTTAGGAAATAC TTTTATTTTCA | 268 |
| C9ORF72_3450 | NC_000009.12 | AATGATGAAATATTAGAGTTGTAATATTGCCTTT ATGATTATCCA | 269 |
| C9ORF72_3962 | NC_000009.12 | TCTTGACAAGATGTGGATGAAATTCTTTAAGTA AAATTGTTTACT | 270 |
| C9ORF72_4147 | NC_000009.12 | ATTGCAATTCTTTTTACTTTCAGTCTTAGATAAC AAGTCTTCAAT | 271 |
| C9ORF72_4226 | NC_000009.12 | ATTAGGCGATTTTGTCATTATGCAAACATCATAG AGTGTACTTAC | 272 |
| C9ORF72_4677 | NC_000009.12 | TTTAACTTTTAAAATACTTAGCTTGAAACACAAA TACATTGTATA | 273 |

TABLE 3-continued

C9ORF72 sequences for selective targeting (Post GGGGCC expansion) (Sense Direction)

| | | |
|---|---|---|
| C9ORF72_5114 NC_000009.12 | GTAGTTTATTATCAAGTGTTGTACACTGTAATAAT TGTATGTGCT | 274 |
| C9ORF72_5257 NC_000009.12 | ACTACCATCATATATGCAGTCTACCATTGACTGA AACGTTACATG | 275 |
| C9ORF72_5594 NC_000009.12 | AAATGCTGTATTGGTTTCTTGGCTAGCATATTAA ATATTTTATC | 276 |
| C9ORF72_5621 NC_000009.12 | ATATTAAATATTTTTATCTTTGTCTTGATACTTCA ATGTCGTTTT | 277 |
| C9ORF72_5782 NC_000009.12 | TTTTTTTTTTTTTTGACCTTTTAGCGGCTTTAAA GTATTTCTGTT | 278 |
| C9ORF72_6030 NC_000009.12 | CCTTTCTTGCCTTGTAGTTTCAACAATCCAGTAT CTGCCTTTGT | 279 |
| C9ORF72_6236 NC_000009.12 | GGAATTGAACATATCTTTTTGGGGGACACAATTC AACCCACAAGT | 280 |
| C9ORF72_6476 NC_000009.12 | ATTTCTAAATGTATGCCCTGAATATAAGTAACAA GTTACCATGTC | 281 |
| C9ORF72_6607 NC_000009.12 | CCACATCTTTGACTTAAGAGGACAAACCAAATA TGTCTAAATCAT | 282 |

| Oligo ID | Targeted mRNA Sequence | SEQ ID NO: | Unmodified Guide Strands | SEQ ID NO: |
|---|---|---|---|---|
| C9ORF72_541 | ACUUUCCCUCUCAUUUCUCU | 283 | UGAGAAAUGAGAGGGAAAGU | 307 |
| C9ORF72_1056 | GCUUAAAGGAAGUGACUAUU | 284 | UAUAGUCACUUCCUUUAAGC | 308 |
| C9ORF72_1116 | AAAGAAGUGCACAGAUUACA | 285 | UGUAAUCUGUGCACUUCUUU | 309 |
| C9ORF72_1283 | UGGUUGUGGCAGUUGGUAAA | 286 | UUUACCAACUGCCACAACCA | 310 |
| C9ORF72_1375 | CUUUUGUACAAAGGAUCAAA | 287 | UUUGAUCCUUUGUACAAAAG | 311 |
| C9ORF72_1847 | UAGUUCCCAGGAGGACUAGG | 288 | UCUAGUCCUCCUGGGAACUA | 312 |
| C9ORF72_2065 | CUCUUUGGGCUGGGAGAAAA | 289 | UUUUCUCCCAGCCCAAAGAG | 313 |
| C9ORF72_2782 | CAGCUGCAUUUGCAUGUAUG | 290 | UAUACAUGCAAAUGCAGCUG | 314 |
| C9ORF72_2802 | GAUUUUUCUCACCAAAGACG | 291 | UGUCUUUGGUGAGAAAAAUC | 315 |
| C9ORF72_3401 | GUUCUGUUUUAGGAAAUACU | 292 | UGUAUUUCCUAAAACAGAAC | 316 |
| C9ORF72_3450 | GAGUUGUAAUAUUGCCUUUA | 293 | UAAAGGCAAUAUUACAACUC | 317 |
| C9ORF72_3962 | GAUGAAAUUCUUUAAGUAAA | 294 | UUUACUUAAAGAAUUUCAUC | 318 |
| C9ORF72_4147 | ACUUCAGUCUUAGAUAACA | 295 | UGUUAUCUAAGACUGAAAGU | 319 |
| C9ORF72_4226 | CAUUAUGCAAACAUCAUAGA | 296 | UCUAUGAUGUUUGCAUAAUG | 320 |
| C9ORF72_4677 | ACUUAGCUUGAAACACAAAU | 297 | UUUUGUGUUUCAAGCUAAGU | 321 |
| C9ORF72_5114 | GUGUUGUACACUGUAAUAAU | 298 | UUUAUUACAGUGUACAACAC | 322 |
| C9ORF72_5257 | GCAGUCUACCAUUGACUGAA | 299 | UUCAGUCAAUGGUAGACUGC | 323 |
| C9ORF72_5594 | UUCUUGGCUAGCAUAUUAAA | 300 | UUUAAUAUGCUAGCCAAGAA | 324 |
| C9ORF72_5621 | AUCUUUGUCUUGAUACUUCA | 301 | UGAAGUAUCAAGACAAAGAU | 325 |
| C9ORF72_5782 | ACCUUUUAGCGGCUUUAAAG | 302 | UUUUAAAGCCGCUAAAAGGU | 326 |
| C9ORF72_6030 | AGUUUCAACAAUCCAGUAUC | 303 | UAUACUGGAUUGUUGAAACU | 327 |
| C9ORF72_6236 | UUUUUGGGGGACACAAUUCA | 304 | UGAAUUGUGUCCCCCAAAAA | 328 |
| C9ORF72_6476 | CCCUGAAUAUAAGUAACAAG | 305 | UUUGUUACUUAUAUUCAGGG | 329 |

TABLE 3-continued

C9ORF72 sequences for selective targeting (Post GGGGCC expansion) (Sense Direction)

| | | | | |
|---|---|---|---|---|
| C9ORF72_6607 | AAGAGGACAAACCAAAUAUG | 306 | UAUAUUUGGUUUGUCCUCUU | 330 |

| Oligo ID | Modified Sequence | SEQ ID NO: |
|---|---|---|
| C9ORF72_541 | P(mU)#(fG)#(mA)(fG)(fA)(fA)(mA)(fU)(mG)(fA)(mG)(fA)(mG)#(fG)#(mG)#(fA)#(mA)#(mA)#(mG)#(fU) | 331 |
| C9ORF72_1056 | P(mU)#(fA)#(mU)(fA)(fG)(fU)(mC)(fA)(mC)(fU)(mU)(fC)(mC)#(fU)#(mU)#(fU)#(mA)#(mA)#(mG)#(fC) | 332 |
| C9ORF72_1116 | P(mU)#(fG)#(mU)(fA)(fA)(fU)(mC)(fU)(mG)(fU)(mG)(fC)(mA)#(fC)#(mU)#(fU)#(mC)#(mU)#(mU)#(fU) | 333 |
| C9ORF72_1283 | P(mU)#(fU)#(mU)(fA)(fC)(fC)(mA)(fA)(mC)(fU)(mG)(fC)(mC)#(fA)#(mC)#(fA)#(mA)#(mC)#(mC)#(fA) | 334 |
| C9ORF72_1375 | P(mU)#(fU)#(mU)(fG)(fA)(fU)(mC)(fC)(mU)(fU)(mU)(fG)(mU)#(fA)#(mC)#(fA)#(mA)#(mA)#(mA)#(fG) | 335 |
| C9ORF72_1847 | P(mU)#(fC)#(mU)(fA)(fG)(fU)(mC)(fC)(mU)(fC)(mC)(fU)(mG)#(fG)#(mG)#(fA)#(mA)#(mC)#(mU)#(fA) | 336 |
| C9ORF72_2065 | P(mU)#(fU)#(mU)(fU)(fC)(fU)(mC)(fC)(mC)(fA)(mG)(fC)(mC)#(fC)#(mA)#(fA)#(mA)#(mG)#(mA)#(fG) | 337 |
| C9ORF72_2782 | P(mU)#(fA)#(mU)(fA)(fC)(fA)(mU)(fG)(mC)(fA)(mA)(fA)(mU)#(fG)#(mC)#(fA)#(mG)#(mC)#(mU)#(fG) | 338 |
| C9ORF72_2802 | P(mU)#(fG)#(mU)(fC)(fU)(mU)(fG)(mG)(fU)(mG)(fA)(mG)#(fA)#(mA)#(fA)#(mA)#(mA)#(mU)#(fC) | 339 |
| C9ORF72_3401 | P(mU)#(fG)#(mU)(fA)(fU)(fU)(mU)(fC)(mC)(fU)(mA)(fA)(mA)#(fA)#(mC)#(fA)#(mG)#(mA)#(mA)#(fC) | 340 |
| C9ORF72_3450 | P(mU)#(fA)#(mA)(fA)(fG)(fG)(mC)(fA)(mA)(fU)(mA)(fU)(mU)#(fA)#(mC)#(fA)#(mA)#(mC)#(mU)#(fC) | 341 |
| C9ORF72_3962 | P(mU)#(fU)#(mU)(fA)(fC)(fU)(mU)(fA)(mA)(fA)(mG)(fA)(mA)#(fU)#(mU)#(fU)#(mC)#(mA)#(mU)#(fC) | 342 |
| C9ORF72_4147 | P(mU)#(fG)#(mU)(fA)(fU)(fU)(mC)(fU)(mA)(fA)(mG)(fA)(mC)#(fU)#(mG)#(fA)#(mA)#(mA)#(mG)#(fU) | 343 |
| C9ORF72_4226 | P(mU)#(fC)#(mU)(fA)(fU)(fG)(mA)(fU)(mG)(fU)(mU)(fU)(mG)#(fC)#(mA)#(fU)#(mA)#(mA)#(mU)#(fG) | 344 |
| C9ORF72_4677 | P(mU)#(fU)#(mU)(fU)(fG)(fU)(mG)(fU)(mU)(fU)(mC)(fA)(mA)#(fG)#(mC)#(fU)#(mA)#(mA)#(mG)#(fU) | 345 |
| C9ORF72_5114 | P(mU)#(fU)#(mU)(fA)(fU)(fU)(mA)(fC)(mA)(fG)(mU)(fG)(mU)#(fA)#(mC)#(fA)#(mA)#(mC)#(mA)#(fC) | 346 |
| C9ORF72_5257 | P(mU)#(fU)#(mC)(fA)(fG)(fU)(mC)(fA)(mA)(fU)(mG)(fG)(mU)#(fA)#(mG)#(fA)#(mC)#(mU)#(mG)#(fC) | 347 |
| C9ORF72_5594 | P(mU)#(fU)#(mU)(fA)(fA)(fU)(mA)(fU)(mG)(fC)(mU)(fA)(mG)#(fC)#(mC)#(fA)#(mA)#(mG)#(mA)#(fA) | 348 |
| C9ORF72_5621 | P(mU)#(fG)#(mA)(fA)(fG)(fU)(mA)(fU)(mC)(fA)(mA)(fG)(mA)#(fC)#(mA)#(fA)#(mA)#(mG)#(mA)#(fU) | 349 |
| C9ORF72_5782 | P(mU)#(fU)#(mU)(fU)(fA)(fA)(mA)(fG)(mC)(fC)(mG)(fC)(mU)#(fA)#(mA)#(fA)#(mA)#(mG)#(mG)#(fU) | 350 |
| C9ORF72_6030 | P(mU)#(fA)#(mU)(fA)(fC)(fU)(mG)(fG)(mA)(fU)(mU)(fG)(mU)#(fU)#(mG)#(fA)#(mA)#(mA)#(mC)#(fU) | 351 |
| C9ORF72_6236 | P(mU)#(fG)#(mA)(fA)(fU)(fU)(mG)(fU)(mG)(fU)(mC)(fC)(mC)#(fC)#(mC)#(fA)#(mA)#(mA)#(mA)#(fA) | 352 |
| C9ORF72_6476 | P(mU)#(fU)#(mU)(fG)(fU)(fU)(mA)(fC)(mU)(fU)(mA)(fU)(mA)#(fU)#(mU)#(fC)#(mA)#(mG)#(mG)#(fG) | 353 |
| C9ORF72_6607 | P(mU)#(fA)#(mU)(fA)(fU)(fU)(mU)(fG)(mG)(fU)(mU)(fU)(mG)#(fU)#(mC)#(fC)#(mU)#(mC)#(mU)#(fU) | 354 |

TABLE 4

C9ORF72 sequences for non-isoform selective targeting (Sense Direction)

| Oligo ID | Accession number | Gene region | SEQ ID NO: |
|---|---|---|---|
| C9ORF72_6686 | NM_001256054.2 | CCTAATCATTGGTTTCATATGTCATTGTTTAGATATCTCCGGAGC | 355 |
| C9ORF72_6702 | NM_145005.6, NM_018325.4, NM_001256054.2 | ATATGTCATTGTTTAGATATCTCCGGAGCATTTGGATAATGTGAC | 356 |
| C9ORF72_6729 | NM_145005.6, NM_018325.4, NM_001256054.2 | GCATTTGGATAATGTGACAGTTGGAATGCAGTGATGTCGACTCTT | 357 |
| C9ORF72_6793 | NM_145005.6, NM_018325.4, NM_001256054.2 | CTGTTGCCAAGACAGAGATTGCTTTAAGTGGCAAATCACCTTTAT | 358 |
| C9ORF72_6802 | NM_145005.6, NM_018325.4, NM_001256054.2 | AGACAGAGATTGCTTTAAGTGGCAAATCACCTTTATTAGCAGCTA | 359 |
| C9ORF72_6903 | NM_145005.6, NM_018325.4, NM_001256054.2 | AAGACAGAACAGGTACTTCTCAGTGATGGAGAAATAACTTTTCTT | 360 |
| C9ORF72_6906 | NM_145005.6, NM_018325.4, NM_001256054.2 | ACAGAACAGGTACTTCTCAGTGATGGAGAAATAACTTTTCTTGCC | 361 |
| C9ORF72_6974 | NM_145005.6, NM_018325.4, NM_001256054.2 | CCTTCGAAATGCAGAGAGTGGTGCTATAGATGTAAAGTTTTTTGT | 362 |
| C9ORF72_7005 | NM_145005.6, NM_018325.4, NM_001256054.2 | GTAAAGTTTTTTGTCTTGTCTGAAAAGGGAGTGATTATTGTTTCA | 363 |
| C9ORF72_7028 | NM_145005.6, NM_018325.4, NM_001256054.2 | AAAGGGAGTGATTATTGTTTCATTAATCTTTGATGGAAACTGGAA | 364 |
| C9ORF72_7032 | NM_145005.6, NM_018325.4, NM_001256054.2 | GGAGTGATTATTGTTTCATTAATCTTTGATGGAAACTGGAATGGG | 365 |
| C9ORF72_7110 | NM_145005.6, NM_018325.4, NM_001256054.2 | CCACAGACAGAACTTAGTTTCTACCTCCCACTTCATAGAGTGTGT | 366 |

| Oligo ID | Targeted mRNA Sequence | SEQ ID NO: | Unmodified Guide Strands | SEQ ID NO: |
|---|---|---|---|---|
| C9ORF72_6686 | CAUAUGUCAUUGUUUAGAUA | 367 | UAUCUAAACAAUGACAUAUG | 379 |
| C9ORF72_6702 | GAUAUCUCCGGAGCAUUUGG | 368 | UCAAAUGCUCCGGAGAUAUC | 380 |
| C9ORF72_6729 | GACAGUUGGAAUGCAGUGAU | 369 | UUCACUGCAUUCCAACUGUC | 381 |
| C9ORF72_6793 | AGAUUGCUUUAAGUGGCAAA | 370 | UUUGCCACUUAAAGCAAUCU | 382 |
| C9ORF72_6802 | UAAGUGGCAAAUCACCUUUA | 371 | UAAAGGUGAUUUGCCACUUA | 383 |
| C9ORF72_6903 | CUUCUCAGUGAUGGAGAAAU | 372 | UUUUCUCCAUCACUGAGAAG | 384 |
| C9ORF72_6906 | CUCAGUGAUGGAGAAAUAAC | 373 | UUUAUUUCUCCAUCACUGAG | 385 |
| C9ORF72_6974 | GAGUGGUGCUAUAGAUGUAA | 374 | UUACAUCUAUAGCACCACUC | 386 |
| C9ORF72_7005 | UUGUCUGAAAAGGGAGUGAU | 375 | UUCACUCCCUUUUCAGACAA | 387 |
| C9ORF72_7028 | UGUUUCAUUAAUCUUUGAUG | 376 | UAUCAAAGAUUAAUGAAACA | 388 |
| C9ORF72_7032 | UCAUUAAUCUUUGAUGGAAA | 377 | UUUCCAUCAAAGAUUAAUGA | 389 |
| C9ORF72_7110 | AGUUUCUACCUCCCACUUCA | 378 | UGAAGUGGGAGGUAGAAACU | 390 |

TABLE 4-continued

C9ORF72 sequences for non-isoform selective targeting (Sense Direction)

| Oligo ID | Modified Sequence | SEQ ID NO: |
| --- | --- | --- |
| C9ORF72_6686 | P(mU)#(fA)#(mU)(fC)(fU)(fA)(mA)(fA)(mC)(fA)(mA)(fU)(mG)#(fA)#(mC)#(fA)#(mU)#(mA)#(mU)#(fG) | 391 |
| C9ORF72_6702 | P(mU)#(fC)#(mA)(fA)(fU)(mG)(fC)(mU)(fC)(mC)(fG)(mG)#(fA)#(mG)#(fA)#(mU)#(mA)#(mU)#(fC) | 392 |
| C9ORF72_6729 | P(mU)#(fU)#(mC)(fA)(fC)(fU)(mG)(fC)(mA)(fU)(fU)(fC)(mC)#(fA)#(mA)#(fC)#(mU)#(mG)#(mU)#(fC) | 393 |
| C9ORF72_6793 | P(mU)#(fU)#(mU)(fG)(fC)(fC)(mA)(fC)(mU)(fU)(mA)(fA)(mA)#(fG)#(mC)#(fA)#(mA)#(mU)#(mC)#(fU) | 394 |
| C9ORF72_6802 | P(mU)#(fA)#(mA)(fA)(fG)(fG)(mU)(fG)(mA)(fU)(mU)(fU)(mG)#(fC)#(mC)#(fA)#(mC)#(mU)#(mU)#(fA) | 395 |
| C9ORF72_6903 | P(mU)#(fU)#(mU)(fU)(fC)(fU)(mC)(fC)(mA)(fU)(mC)(fA)(mC)#(fU)#(mG)#(fA)#(mG)#(mA)#(mA)#(fG) | 396 |
| C9ORF72_6906 | P(mU)#(fU)#(mU)(fA)(fU)(fU)(mU)(fC)(mU)(fC)(mC)(fA)(mU)#(fC)#(mA)#(fC)#(mU)#(mG)#(mA)#(fG) | 397 |
| C9ORF72_6974 | P(mU)#(fU)#(mA)(fC)(fA)(fU)(mC)(fU)(mA)(fU)(mA)(fG)(mC)#(fA)#(mC)#(fC)#(mA)#(mC)#(mU)#(fC) | 398 |
| C9ORF72_7005 | P(mU)#(fU)#(mC)(fA)(fC)(fU)(mC)(fC)(mC)(fU)(mU)(fU)(mU)#(fC)#(mA)#(fG)#(mA)#(mA)#(mA)#(fA) | 399 |
| C9ORF72_7028 | P(mU)#(fA)#(mU)(fC)(fA)(fA)(mA)(fG)(mA)(fU)(mU)(fA)(mA)#(fU)#(mG)#(fA)#(mA)#(mA)#(mC)#(fA) | 400 |
| C9ORF72_7032 | P(mU)#(fU)#(mU)(fC)(fC)(fA)(mU)(fC)(mA)(fA)(mA)(fG)(mA)#(fU)#(mU)#(fA)#(mA)#(mU)#(mG)#(fA) | 401 |
| C9ORF72_7110 | P(mU)#(fG)#(mA)(fA)(fG)(fU)(mG)(fG)(mG)(fA)(mG)(fG)(mU)#(fA)#(mG)#(fA)#(mA)#(mA)#(mC)#(fU) | 402 |

TABLE 5

C9ORF72 sequences for non-isoform selective targeting (Antisense Direction)

| Oligo ID | Gene region | SEQ ID NO: |
| --- | --- | --- |
| C9ORF72_AS_6686 | CCTAATCATTGGTTTCATATGTCATTGTTTAGATATCTCCGGAGC | 355 |
| C9ORF72_AS_6702 | ATATGTCATTGTTTAGATATCTCCGGAGCATTTGGATAATGTGAC | 356 |
| C9ORF72_AS_6729 | GCATTTGGATAATGTGACAGTTGGAATGCAGTGATGTCGACTCTT | 357 |
| C9ORF72_AS_6793 | CTGTTGCCAAGACAGAGATTGCTTTAAGTGGCAAATCACCTTTAT | 358 |
| C9ORF72_AS_6802 | AGACAGAGATTGCTTTAAGTGGCAAATCACCTTTATTAGCAGCTA | 359 |
| C9ORF72_AS_6903 | AAGACAGAACAGGTACTTCTCAGTGATGGAGAAATAACTTTTCTT | 360 |
| C9ORF72_AS_6906 | ACAGAACAGGTACTTCTCAGTGATGGAGAAATAACTTTTCTTGCC | 361 |
| C9ORF72_AS_6974 | CCTTCGAAATGCAGAGAGTGGTGCTATAGATGTAAAGTTTTTGT | 362 |
| C9ORF72_AS_7005 | GTAAAGTTTTTGTCTTGTCTGAAAAGGGAGTGATTATTGTTTCA | 363 |
| C9ORF72_AS_7028 | AAAGGGAGTGATTATTGTTTCATTAATCTTTGATGGAAACTGGAA | 364 |
| C9ORF72_AS_7032 | GGAGTGATTATTGTTTCATTAATCTTTGATGGAAACTGGAATGGG | 365 |
| C9ORF72_AS_7110 | CCACAGACAGAACTTAGTTTCTACCTCCCACTTCATAGAGTGTGT | 366 |

| Oligo ID | Targeted Antisense mRNA Sequence | SEQ ID NO: | Unmodified Guide Strands | SEQ ID NO: |
| --- | --- | --- | --- | --- |
| C9ORF72_AS_6686 | UAUCUAAACAAUGACAUAUA | 403 | UAUAUGUCAUUGUUUAGAUA | 413 |
| C9ORF72_AS_6702 | CCAAAUGCUCCGGAGAUAUA | 404 | UAUAUCUCCGGAGCAUUUGG | 414 |

TABLE 5-continued

C9ORF72 sequences for non-isoform selective targeting
(Antisense Direction)

| Oligo ID | Sequence | SEQ ID NO: | Sequence | SEQ ID NO: |
|---|---|---|---|---|
| C9ORF72_AS_6729 | AUCACUGCAUUCCAACUGUA | 405 | UACAGUUGGAAUGCAGUGAU | 415 |
| C9ORF72_AS_6793 | UUUGCCACUUAAAGCAAUCA | 406 | UGAUUGCUUUAAGUGGCAAA | 416 |
| C9ORF72_AS_6802 | UAAAGGUGAUUUGCCACUUA | 383 | UAAGUGGCAAAUCACCUUUA | 371 |
| C9ORF72_AS_6903 | AUUUCUCCAUCACUGAGAAA | 407 | UUUCUCAGUGAUGGAGAAAU | 417 |
| C9ORF72_AS_6906 | GUUAUUUCUCCAUCACUGAA | 408 | UUCAGUGAUGGAGAAAUAAC | 418 |
| C9ORF72_AS_6974 | UUACAUCUAUAGCACCACUA | 409 | UAGUGGUGCUAUAGAUGUAA | 419 |
| C9ORF72_AS_7005 | AUCACUCCCUUUUCAGACAA | 410 | UUGUCUGAAAAGGGAGUGAU | 375 |
| C9ORF72_AS_7028 | CAUCAAAGAUUAAUGAAACA | 411 | UGUUUCAUUAAUCUUUGAUG | 376 |
| C9ORF72_AS_7032 | UUUCCAUCAAAGAUUAAUGA | 389 | UCAUUAAUCUUUGAUGGAAA | 377 |
| C9ORF72_AS_7110 | UGAAGUGGGAGGUAGAAACA | 412 | UGUUUCUACCUCCCACUUCA | 420 |

| Oligo ID | Modified Sequence | SEQ ID NO: |
|---|---|---|
| C9ORF72_AS_6686 | P(mU)#(fA)#(mU)(fA)(mU)(fG)(mU)(fC)(mA)(fU)(mU)(fG)(mU)#(fU)#(mU)#(fA)#(mG)#(fA)#(mU)#(mA) | 421 |
| C9ORF72_AS_6702 | P(mU)#(fA)#(mU)(fA)(mU)(fC)(mU)(fC)(mC)(fG)(mG)(fA)(mG)#(fC)#(mA)#(fU)#(mU)#(fU)#(mG)#(mG) | 422 |
| C9ORF72_AS_6729 | P(mU)#(fA)#(mC)(fA)(mG)(fU)(mU)(fG)(mG)(fA)(mA)(fU)(mG)#(fC)#(mA)#(fG)#(mU)#(fG)#(mA)#(mU) | 423 |
| C9ORF72_AS_6793 | P(mU)#(fG)#(mA)(fU)(mU)(fG)(mC)(fU)(mU)(fU)(mA)(fA)(mG)#(fU)#(mG)#(fG)#(mC)#(fA)#(mA)#(mA) | 424 |
| C9ORF72_AS_6802 | P(mU)#(fA)#(mA)(fG)(mU)(fG)(mG)(fC)(mA)(fA)(mA)(fU)(mC)#(fA)#(mC)#(fC)#(mU)#(fU)#(mU)#(mA) | 425 |
| C9ORF72_AS_6903 | P(mU)#(fU)#(mU)(fC)(mU)(fC)(mA)(fG)(mU)(fG)(mA)(fU)(mG)#(fG)#(mA)#(fG)#(mA)#(fA)#(mA)#(mU) | 426 |
| C9ORF72_AS_6906 | P(mU)#(fU)#(mC)(fA)(mG)(fU)(mG)(fA)(mU)(fG)(mG)(fA)(mG)#(fA)#(mA)#(fA)#(mU)#(fA)#(mA)#(mC) | 427 |
| C9ORF72_AS_6974 | P(mU)#(fA)#(mG)(fU)(mG)(fG)(mU)(fG)(mC)(fU)(mA)(fU)(mA)#(fG)#(mA)#(fU)#(mG)#(fU)#(mA)#(mA) | 428 |
| C9ORF72_AS_7005 | P(mU)#(fU)#(mG)(fU)(mC)(fU)(mG)(fA)(mA)(fA)(mA)(fG)(mG)#(fG)#(mA)#(fG)#(mU)#(fG)#(mA)#(mU) | 429 |
| C9ORF72_AS_7028 | P(mU)#(fG)#(mU)(fU)(mU)(fC)(mA)(fU)(mU)(fA)(mA)(fU)(mC)#(fU)#(mU)#(fU)#(mG)#(fA)#(mU)#(mG) | 430 |
| C9ORF72_AS_7032 | P(mU)#(fC)#(mA)(fU)(mU)(fA)(mA)(fU)(mC)(fU)(mU)(fU)(mG)#(fA)#(mU)#(fG)#(mG)#(fA)#(mA)#(mA) | 431 |
| C9ORF72_AS_7110 | P(mU)#(fG)#(mU)(fU)(mU)(fC)(mU)(fA)(mC)(fC)(mU)(fC)(mC)#(fC)#(mA)#(fC)#(mU)#(fU)#(mC)#(mA) | 432 |

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms can also be useful for blocking translation of mutant proteins, in the absence of siRNA-mediated gene-silencing. Such applications can be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the present application include both unmodified siRNAs and modified siRNAs as known in the art, such as crosslinked siRNA derivatives or derivatives having non-nucleotide moieties linked, for example to their 3' or 5' ends. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the present application can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present application can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

IV. Anti-C9ORF72 RNA Silencing Agents

In one embodiment, the present application provides novel anti-C9ORF72 RNA silencing agents (e.g., siRNA and shRNAs), methods of making said RNA silencing agents, and methods (e.g., research and/or therapeutic methods) for using said improved RNA silencing agents (or portions thereof) for RNA silencing of C9ORF72 protein. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi). Also provided are a second type of RNA silencing agents (or portions thereof) for silencing C9ORF72 antisense transcripts. The second type RNA silencing agents comprise a sense strand (or portions thereof), wherein the sense strand has sufficient complementarity to an antisense transcript to mediate an RNA-mediated silencing mechanism.

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); and (5) single-stranded, fully phosphorothioated tails of 5-8 bases. The number of phosphorothioate modifications is varied from 6 to 17 total in different embodiments.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the present application having the structural properties described above and herein can be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the present application can be described in the following aspects and embodiments.

In a first aspect, provided herein is an oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide and a second oligonucleotide, wherein: (1) the first oligonucleotide is an oligonucleotide described herein (e.g., comprising one of the target sequences of Tables 1-5); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In a third aspect, provided herein is oligonucleotide having the structure:

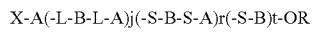

X-A(-L-B-L-A)j(-S-B-S-A)r(-S-B)t-OR wherein: X is a 5' phosphate group; A, for each occurrence, independently is a 2'-methoxy-ribonucleotide; B, for each occurrence, independently is a 2'-fluoro-ribonucleotide; L, for each occurrence independently is a phosphodiester or phosphorothioate linker; O is oxygen; S is a phosphorothioate linker; and R is selected from hydrogen and a capping group (e.g., an acyl such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein: (1) the first oligonucleotide is selected from the oligonucleotides of the third aspect; (2) a portion of the first oligonucleotide is complementary to a portion of the second oligonucleotide; and (3) the second oligonucleotide has the structure:

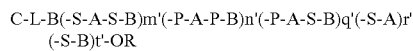

C-L-B(-S-A-S-B)m'(-P-A-P-B)n'(-P-A-S-B)q'(-S-A)r'
(-S-B)t'-OR wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-4 repeat units of ethylene glycol, a phosphodiester, and a phosphorothioate; S is a phosphorothioate linker; P is a phosphodiester linker; R is selected from hydrogen and a capping group (e.g., an acyl such as acetyl); m' is 0 or 1; n' is 4, 5 or 6; q' is 0 or 1; r' is 0 or 1; and t' is 0 or 1.

a) Design of Anti-C9ORF72 siRNA Molecules

In an example embodiment, an siRNA molecule of the present application is a duplex consisting of a sense strand and complementary antisense strand, the antisense strand having sufficient complementarity to a C9ORF72 mRNA to mediate RNAi. Also provided are siRNA molecules where the sense strand has sufficient complementarity to a C9ORF72 antisense strand to mediate RNAi. In one embodiment, the siRNA molecule has a length from about 10-50 or more nucleotides, i.e., each strand comprises 10-50 nucleotides (or nucleotide analogs). In another embodiment, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In yet a different embodiment, the strands are aligned such that there are at least 1, 2, or 3 bases at the end of the strands, which do not align (i.e., for which no complementary bases occur in the opposing strand) such that an overhang of 1, 2 or 3 residues occurs at one or both ends of the duplex when strands are annealed. In another embodiment, the siRNA molecule has a length from about 10-50 or more nucleotides, i.e., each strand comprises 10-50 nucleotides (or nucleotide analogs). In still another embodiment, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Usually, siRNAs can be designed by using any method known in the art, for instance, by using the following protocol:

1. The siRNA should be specific for a target sequence, e.g., a target sequence set forth in Tables 1-5. In one embodiment, a target sequence is found in a wild-type C9ORF72 allele. In another embodiment, a target sequence is found in both a mutant C9ORF72 allele, and a wild-type C9ORF72 allele. In another embodiment, a target sequence is found in a wild-type C9ORF72 allele. The first strand should be complementary to the target sequence, and the other strand is substantially complementary to the first strand. (See Tables 1-5 for exemplary sense and antisense strands.) Exemplary sense target sequences are selected from the 5' untranslated region (5'-UTR) of a target gene. Cleavage of mRNA at these sites should eliminate translation of corresponding C9ORF72 protein. Target sequences from other regions of the C9ORF72 gene, including a number of antisense sequences, are also suitable for targeting. A sense strand is designed based on the target sequence. Further, siRNAs with lower G/C content (35-55%) can be more active than those with G/C content higher than 55%. Thus, in one embodiment, the present application includes nucleic acid molecules having 35-55% G/C content.

2. In embodiments where the target sequence is in the sense direction, the sense strand of the siRNA is designed based on the sequence of the selected target site. In one embodiment, the sense strand includes about 19 to 25 nucleotides, e.g., 19, 20, 21, 22, 23, 24 or 25 nucleotides. In another embodiment, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant present application, provided that they retain the ability to mediate RNAi. Longer RNA silencing agents have been demonstrated to elicit an interferon or Protein Kinase R (PKR) response in certain mammalian cells which can be undesirable. In one embodiment, the RNA silencing agents of the present application do not elicit a PKR response (i.e., are of a sufficiently short length). However, longer RNA silencing agents can be useful, for example, in cell types incapable of generating a PKR response or in situations where the PKR response has been down-regulated or dampened by alternative means.

The siRNA molecules of the present application have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed to have a sequence sufficiently identical to a portion of the target. For example, the sense strand can have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The present application has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides can also be effective for mediating RNAi. Alternatively, siRNA sequences with nucleotide analog substitutions or insertions can be effective for inhibition.

Sequence identity can be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules can have a 3' overhang of 2 nucleotides, such as TT. The overhanging nucleotides can be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA can be found in "The siRNA User Guide," available at The Max-Plank-Institut fur Biophysikalische Chemie website.

Alternatively, the siRNA can be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant C9ORF72 mRNA), the siRNA can be incubated with target cDNA (e.g., C9ORF72 cDNA) in a *Drosophila*-based in vitro mRNA expression system. Radiolabeled with $^{32}$P, newly synthesized target mRNAs (e.g., C9ORF72 mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-C9ORF72 siRNAs can be designed to target any of the target sequences described supra. Said siRNAs comprise an antisense strand which is sufficiently complementary with the target sequence to mediate silencing of the target sequence. In certain embodiments, the RNA silencing agent is a siRNA.

Sites of siRNA-mRNA complementation are selected which result in optimal mRNA specificity and maximal mRNA cleavage.

b) siRNA-Like Molecules siRNA-like molecules of the present application have a sequence (i.e., have a strand having a sequence) that is "sufficiently complementary" to a target sequence of an C9ORF72 mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) can be targeted in certain embodiments.

The capacity of a siRNA-like duplex to mediate RNAi or translational repression can be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide can be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant present application provides shRNAs capable of mediating RNA silencing of an C9ORF72 target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the present application are artificial constructs based on these naturally occurring pre-miRNAs, but which are engineered to deliver desired RNA silencing agents (e.g., siRNAs of the present application). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant present application, one portion of the duplex stem is a nucleic acid sequence that is complementary (or anti-sense) to the C9ORF72 target sequence. In one embodiment, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are about 15 to about 50 nucleotides in length. In another embodiment, the two stem portions are about 18 or 19 to about 21, 22, 23, 24, 25, 30, 35, 37, 38, 39, or 40 or more nucleotides in length. In other embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors can differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors can differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the present application include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., C9ORF72 mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an intronic and/or exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the present application include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Gene Silencing Oligonucleotides

In certain exemplary embodiments, gene expression (i.e., C9ORF72 gene expression) can be modulated using oligonucleotide-based compounds comprising two or more single stranded antisense oligonucleotides that are linked through their 5'-ends that allow the presence of two or more accessible 3'-ends to effectively inhibit or decrease C9ORF72 gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and can be directly via 5', 3' or 2' hydroxyl groups, or indirectly, via a non-nucleotide linker or a nucleoside, utilizing either the 2' or 3' hydroxyl positions of the nucleoside. Linkages can also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds can comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components can be covalently attached. Some oligonucleotide-based compounds of the present application, therefore, comprise two or more oligonucleotides linked to a nucleotide or a non-nucleotide linker. Such oligonucleotides according to the present application are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides can also be modified in a number of ways without compromising their ability to hybridize to mRNA. Such modifications can include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

V. Modified Anti-C9ORF72 RNA Silencing Agents

In certain aspects of the present application, an RNA silencing agent (or any portion thereof) of the present application as described supra can be modified such that the activity of the agent is further improved. For example, the RNA silencing agents described in Section II supra can be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the present application can be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification can be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the present application are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the present application are modified by the introduction of at least one destabilizing nucleotide within 5 nucleotides from a specificity-determining nucleotide (i.e., the nucleotide which recognizes the disease-related polymorphism). For example, the destabilizing nucleotide can be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide can be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the present application can be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the present application or an siRNA produced from a shRNA) into RISC in favor of the sense strand, such that the antisense strand preferentially guides cleavage or translational repression of a target mRNA, and thus increasing or improving the efficiency of target cleavage and silencing. In one embodiment, the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the present application can be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the present application can be enhanced such that there is at least one mismatched base pair between the 5' end of the first or antisense strand and the 3' end of the sense strand portion. In one embodiment, the mismatched base pair is selected from the group consisting of G:A, C:A, C:U, G:G, A:A, C:C and U:U. In another embodiment, the asymmetry of an RNA silencing agent of the present application can be enhanced such that there is at least one wobble base pair, e.g., G:U, between the 5' end of the first or antisense strand and the 3' end of the sense strand portion. In another embodiment, the asymmetry of an RNA silencing agent of the present application can be enhanced such that there is at least one base pair comprising a rare nucleotide, e.g., inosine (I). In still another embodiment, the base pair is selected from the group consisting of an I:A, I:U and I:C. In yet another embodiment, the asymmetry of an RNA silencing agent of the present application can be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present application can be modified to improve stability in serum or in growth medium for cell cultures. In order to enhance the stability, the 3'-residues can be stabilized against degradation, e.g., they can be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the present application features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the present application features RNA silencing agents that are at least 80% chemically modified. In a preferred embodiment of the present application, the RNA silencing agents can be fully chemically modified, i.e., 100% of the nucleotides are chemically modified.

In a preferred embodiment of the present application, the RNA silencing agents can contain at least one modified nucleotide analogue. The nucleotide analogues can be located at positions where the target-specific silencing activity, e.g., the RNAi mediating activity or translational repression activity is not substantially effected, e.g., in a region at the 5'-end and/or the 3'-end of the siRNA molecule. Particularly, the ends can be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA can be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant present application. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the present application comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the present application comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases can be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications can be combined.

In other embodiments, cross-linking can be employed to alter the pharmacokinetics of the RNA silencing agent, for example, to increase half-life in the body. Thus, the present application includes RNA silencing agents having two complementary strands of nucleic acid, wherein the two strands are crosslinked. The present application also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an 0 with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents can be modified with chemical moieties, for example, to enhance cellular uptake by target cells (e.g., neuronal cells). Thus, the present application includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of present application is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine.

5) Tethered Ligands

Other entities can be tethered to an RNA silencing agent of the present application. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or Eu(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and can also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{11}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{11}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, a helical cell-permeation agent. In one embodiment, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is an alpha-helical agent, which has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

6) Branched Oligonucleotides

In other embodiments, RNA silencing agents can be connected to one another by one or more moieties independently selected from a linker, a spacer and a branching point. The branched RNA silencing agents, or branched oligonucleotides, have two to eight oligonucleotides attached through a linker. The linker can be hydrophilic or hydrophobic. In a particular embodiment, compounds of the present application have two to three oligonucleotides. In one embodiment, the oligonucleotides independently have substantial chemical stabilization (e.g., at least 40% of the constituent bases are chemically-modified). In a particular embodiment, the oligonucleotides have full chemical stabilization (i.e., all of the constituent bases are chemically-modified). In some embodiments, compounds of the present application comprise one or more single-stranded phosphorothioated tails, each independently having two to twenty nucleotides. In a particular embodiment, each single-stranded tail has eight to ten nucleotides.

In certain embodiments, compounds of the present application are characterized by three properties: (1) a branched structure, (2) full metabolic stabilization, and (3) the presence of a single-stranded tail comprising phosphorothioate linkers. In a particular embodiment, compounds of the present application have 2 or 3 branches. The increased overall size of the branched structures promote increased uptake. Also, without being bound by a particular theory of activity, multiple adjacent branches (e.g., 2 or 3) allow each branch to act cooperatively and thus dramatically enhance rates of internalization, trafficking and release.

In certain embodiments, compounds of the present application are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phoshorothioated single oligonucleotides containing at least 3, optimally 5-20 phosphorothioated bonds.

VI. Dual-Acting RNA Silencing Agents

As anticipated above, RAN dipeptides are expressed from sense and antisense hexanucleotide-containing transcripts and both need to be targeted to reduce C9orf72-related neuropathology. In an aspect, the current disclosure introduces for the first time the concept of dual-targeting RNA silencing agents for the non-repeat regions of C9orf72, which carry a first guide strand and a second guide strand within the same molecule to enable simultaneous silencing of both sense and antisense transcripts.

In representative embodiments of this aspect, the first guide strand and second guide strand form a double-stranded (ds) RNA construct such as an siRNA. In traditional siRNAs, only the guide strand is loaded onto the RISC while the other strand, the passenger strand, is degraded. In contrast, the dual-acting siRNA of the present disclosure is formed by two guide strands. The first guide strand inhibits the expression of a C9orf72 sense transcript while the second guide strand inhibits the expression of a C9orf72 antisense transcript, thereby providing a construct capable of targeting both sense and antisense RAN dipeptide transcripts. Usually, the guide strands can each independently be 15 to 30 nucleotides in length. In representative embodiments, the guide strands each independently include about 15-25 nucleotides, such as 16, at least 17, at least 18, at least 19, or at least 20 contiguous nucleotides.

In a non-limiting embodiment, the first guide strand and second guide strand form a dsRNA construct where each strand includes an overhang of about 5 nucleotides in length at the 3' end to promote entry into the RISC machinery, as seen in traditional siRNAs. Alternatively, provided herein are novel dual-acting RNAs based on a novel chemical scaffold for sense/antisense targeting which does not require single-stranded overhangs. FIG. 24 is a visual illustration of the structural differences between a traditional siRNA and the novel scaffold. The traditional siRNA of FIG. 24A features a 20 nucleotide guide strand and a 15 nucleotide passenger strand, each containing alternating 2'O-methyl and 2'-fluoro modifications, wherein the dsRNA has 100% complementarity and the guide strand has a 5 nucleotide overhang, as well as a passenger strand with a TEG linker at the 3' end. FIG. 24B depicts the novel, dual-acting siRNA chemical scaffold, including two guide strands. The first guide strand inhibits the expression of a sense transcript while the second guide strand inhibits the expression of an antisense transcript.

The strands can be the same length, e.g., 20 nucleotides long. Instead of relying on single-stranded overhangs, each strand has at least one nucleotide mismatch at the 3'end to promote entry into the RISC machinery, although the number of mismatches at each 3'end can independently be 2, 3, or more if conducive to better performance. Optionally, a single-stranded overhang can be added to either or both guide strands to further facilitate engagement with the RISC machinery.

In further embodiments of this aspect, the first guide strand and second guide strand do not form a double-stranded RNA construct with one another. Rather, the first guide strand forms a first siRNA with a first passenger strand, and the second guide strand forms a second siRNA with a second passenger strand. The first siRNA and the second siRNA are connected to one another by one or more moieties selected from the group consisting of a linker, a spacer, and a branching point. Hence, a dual-acting silencing agent including a first siRNA with a first guide strand and a second siRNA with a second guide strand is provided. In a non-limiting embodiment, each siRNA is independently connected to the linker, spacer, or branching point at the 3' end or at the 5' end of its respective guide strand or passenger strand. Example linkers include ethylene glycol chains, alkyl chains, peptides, RNA, DNA, phosphates, phosphonates, phosphoramidates, esters, amides, and triazoles. Optionally, any carbon or oxygen atom of the linker can be replaced with a nitrogen atom, bears a hydroxyl substituent, or bears an oxo substituent.

Figure 25A:
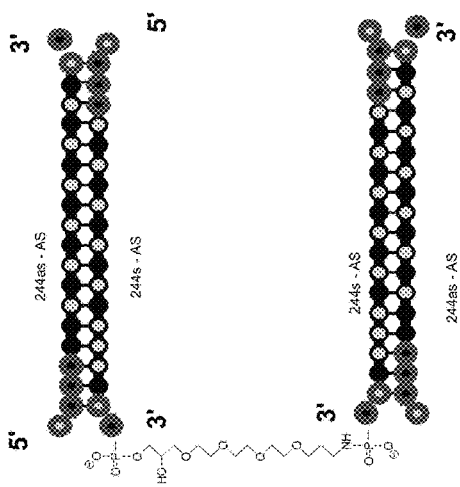
FIG. 25A-FIG. 25C depicts variants of the siRNA chemical scaffold of FIG. 24B.
Figure 25B:
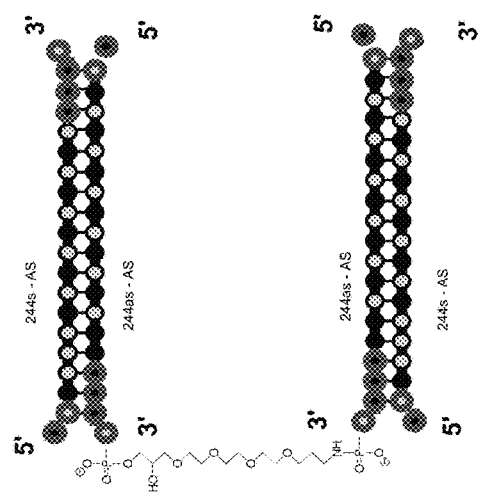
Figure 25C:
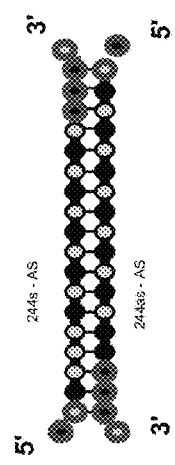

FIG. 25 depicts variants of the siRNA chemical scaffold of FIG. 24B. FIG. 25A depicts an siRNA chemical scaffold with alternating nucleotide modifications at all positions of the guide strand except positions 5 and 18 and alternating nucleotide modifications on the passenger strand except positions 16 and 18, where adjacent nucleotides are connected via either phosphorothioate bond or phosphodiester bond, and the scaffold consists of one sense-targeting and one antisense-targeting RNA. FIG. 25B depicts an siRNA chemical scaffold with alternating nucleotide modifications at all positions of the guide strand except positions 5 and 18 and alternating nucleotide modifications on the passenger strand except positions 16 and 18, where adjacent nucleotides are connected via either phosphorothioate bond or phosphodiester bond, and the scaffold consists of two sense-targeting and two antisense-targeting RNA molecules, connected via a linker at the 3' end of each antisense strand. FIG. 25C depicts an siRNA chemical scaffold with alternating nucleotide modifications at all positions of the guide strand except positions 5 and 18 and alternating nucleotide modifications on the passenger strand except positions 16 and 18, where adjacent nucleotides are connected via either phosphorothioate bond or phosphodiester bond, and the scaffold consists of two sense-targeting and two antisense-targeting RNA molecules, connected via a linker at the 3' end of each sense strand.

In the same manner as traditional RNA silencing agents, any of the dual-acting RNA silencing agents disclosed herein can be modified with chemical moieties, for example to enhance uptake by neuronal cells. In non-limiting embodiments, a dual-acting RNA silencing agent is conjugated to a lipophilic moiety. In one example, the lipophilic moiety is a ligand that includes a cationic group. In another embodiment, the lipophilic moiety is attached to the first strand, second strand, or both strands of the dual-acting RNA. In an exemplary embodiment, the lipophilic moiety is attached to one end of the first strand or to one end of the second strand. In another exemplary embodiment, the lipophilic moiety is attached to the 3' end of either the first strand or second strand. In representative embodiments, the lipophilic moiety is selected from alkyl, alkenyl, aryl, lipophilic vitamin, vitamin derivative, cholesterol, cholesterol derivative, and lipophilic amino acid. In a further non-limiting example, the RNA silencing agent can instead be conjugated to a hydrophilic moiety. Example hydrophilic moieties include aptamers, carbohydrates, and hydrophilic vitamins.

Also as disclosed herein for traditional RNA silencing agents, the strands of the dual-acting RNA silencing agent can be modified by the substitution of one or more nucleotides with chemically-modified nucleotides, such that in vivo stability is enhanced as compared to a corresponding unmodified RNA silencing agent. In some embodiments, the first strand, second strand or both strands of the dual-acting RNA silencing agent are at least 80% chemically modified. In a preferred embodiment, either or both strands can be fully chemically modified, i.e., 100% of the nucleotides are chemically modified. In a non-limiting embodiment, the modified nucleotide can be selected from 2'-O-methyl modified nucleotide, a nucleotide comprising a 5'-phosphorothioate group, 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

VII. Methods of Introducing Nucleic Acids, Vectors and Host Cells

RNA silencing agents of the present application can be directly introduced into the cell (e.g., a neural cell) (i.e., intracellularly); or introduced extracellularly into a cavity, interstitial space, into the circulation of an organism, introduced orally, or can be introduced by bathing a cell or organism in a solution containing the nucleic acid. Vascular or extravascular circulation, the blood or lymph system, and the cerebrospinal fluid are sites where the nucleic acid can be introduced.

The RNA silencing agents of the present application can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells can be used, such as lipid-mediated carrier transport, chemical-mediated transport, and cationic liposome transfection such as calcium phosphate, and the like. The nucleic acid can be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells can be used, such as lipid-mediated carrier transport, chemical-mediated transport, such as calcium phosphate, and the like. Thus, the RNA can be introduced along with components that perform one or more of the following activities: enhance RNA uptake by the cell, inhibit annealing of single strands, stabilize the single strands, or other-wise increase inhibition of the target gene.

RNA can be directly introduced into the cell (i.e., intracellularly); or introduced extracellularly into a cavity, interstitial space, into the circulation of an organism, introduced orally, or can be introduced by bathing a cell or organism in a solution containing the RNA. Vascular or extravascular circulation, the blood or lymph system, and the cerebrospinal fluid are sites where the RNA can be introduced.

The cell having the target gene can be from the germ line or somatic, totipotent or pluripotent, dividing or non-dividing, parenchyma or epithelium, immortalized or transformed, or the like. The cell can be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process can provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, Radio-ImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present application. Lower doses of injected material and longer times after administration of RNAi agent can result in inhibition in a smaller fraction of cells (e.g., at least 10%, 20%, 50%, 75%, 90%, or 95% of targeted cells). Quantization of gene expression in a cell can show similar amounts of inhibition at the level of accumulation of target mRNA or translation of target protein. As an example, the efficiency of inhibition can be determined by assessing the amount of gene product in the cell; mRNA can be detected with a hybridization probe having a nucleotide sequence outside the region used for the inhibitory double-stranded RNA, or translated polypeptide can be detected with an antibody raised against the polypeptide sequence of that region.

The RNA can be introduced in an amount which allows delivery of at least one copy per cell. Higher doses (e.g., at least 5, 10, 100, 500 or 1000 copies per cell) of material can yield more effective inhibition; lower doses can also be useful for specific applications.

In an exemplary aspect, the efficacy of an RNAi agent of the present application (e.g., an siRNA targeting an C9ORF72 target sequence) is tested for its ability to specifically degrade mutant mRNA (e.g., C9ORF72 mRNA and/or the production of C9ORF72 protein) in cells, in particular, in neurons and/or astrocytes (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant C9ORF72 cDNA). Standard siRNA, modified siRNA or vectors able to produce siRNA from U-looped mRNA are co-transfected. Selective reduction in target mRNA (e.g., C9ORF72 mRNA) and/or target protein (e.g., C9ORF72 protein) is measured. Reduction of target mRNA or protein can be compared to levels of target mRNA or protein in the absence of an RNAi agent or in the presence of an RNAi agent that does not target C9ORF72 mRNA. Exogenously-introduced mRNA or protein (or endogenous mRNA or protein) can be assayed for comparison purposes.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 Can 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs can be delivered to a subject in compositions according to any appropriate methods known in the art. An rAAV can be suspended in a physiologically compatible carrier (i.e., in a composition), and can be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject can be performed, for example, by intramuscular injection or by administration into the bloodstream of the mammalian subject. Administration into the bloodstream can be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it can be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs can be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the present application can comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and can thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present application is a "cis-acting" plasmid containing the transgene, in which the selected transgene sequence and associated regulatory elements are flanked by the 5' and 3' AAV ITR sequences. The AAV ITR sequences can be obtained from any known AAV, including mammalian AAV types described further herein.

VII. Methods of Treatment

The present application provides for both prophylactic and therapeutic methods of treating a subject at risk of (or susceptible to) a disease or disorder caused, in whole or in part, by abnormalities in the C9ORF72 gene. In one embodiment, such abnormalities have been found to be predictive of neurodegeneration progression in the brain and spinal cord. In another embodiment, the disease or disorder is a polyglutamine disorder. In a preferred embodiment, the disease or disorder one in which reduction of C9ORF72 in the CNS reduces clinical manifestations seen in neurodegenerative diseases such as AD and ALS. The double-acting, double-stranded (ds) RNAs disclosed herein also find use in inhibiting the expression of disease- or disorder-associated antisense C9ORF72 transcripts.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the present application provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the present application pertains to methods treating subjects therapeutically, i.e., alter onset of symptoms of the disease or disorder. In an exemplary embodiment, the modulatory method of the present application involves contacting a CNS cell expressing C9ORF72 with a therapeutic agent (e.g., a RNAi agent or vector or transgene encoding same) that is specific for a target sequence within the gene, such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments can be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the present application provides methods for tailoring an individual's prophylactic or therapeutic treatment with either the target gene molecules of the present application or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the present application can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or about 0.0001-0.001 mg per organ, about 0.03-3.0 mg per organ, about 0.1-3.0 mg per eye or about 0.3-3.0 mg per organ. The dosage can be an amount effective to treat or prevent a neurodegenerative disease or disorder, e.g., AD or ALS. In one embodiment, the unit dose is administered less frequently than once a day, e.g., less than every 2, 4, 8 or 30 days. In another embodiment, the unit dose is not administered with a frequency (e.g., not a regular frequency). For example, the unit dose can be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 g to 1.4 mg/kg of body weight per day, e.g., 10, 1, 0.1, 0.01, 0.001, or 0.00001 mg per kg of bodyweight per day. The maintenance doses are administered no more than once every 5, 10, or 30 days. Further, the treatment regimen can last for a period of time which will vary depending upon the nature of the particular disease, its severity and the overall condition of the patient. In preferred embodiments the dosage can be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound can either be increased in the event the patient does not respond significantly to current dosage levels, or the dose can be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir can be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it can be desirable to have the patient undergo maintenance therapy to prevent the recurrence of the disease state, wherein the compound of the present application is administered in maintenance doses, ranging from 0.01 g to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors can influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, can include a series of treatments. It will also be appreciated that the effective dosage of an RNA silencing agent for treatment can increase or decrease over the course of a particular treatment. Changes in dosage can result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages can vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

VII. Pharmaceutical Compositions and Methods of Administration

The present application pertains to uses of the above-described agents for prophylactic and/or therapeutic treatments as described infra. Accordingly, the modulators (e.g., RNAi agents) of the present application can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the present application is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the present application is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the present application are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage can vary within this range depending upon the dosage form employed and the route of administration utilized. For any compound used in the method of the present application, the therapeutically effective dose can be estimated initially from cell culture assays. A dose can be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma can be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 μg to 1000 mg can be administered; in some embodiments, 10, 30, 100 or 1000 μg can be administered. In some embodiments, 1-5 g of the compositions can be administered. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments.

The nucleic acid molecules of the present application can be inserted into expression constructs, e.g., viral vectors, retroviral vectors, expression cassettes, or plasmid viral vectors, e.g., using methods known in the art, including but not limited to those described in Xia et al., (2002), supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the present application can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs can be any construct suitable for use in the appropriate expression system and include, but are not limited to retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain exemplary embodiments, a composition that includes an RNA silencing agent of the present application can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas or cortex of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present application can be administered in a number of ways depending upon whether local or systemic treatment is desired and upon the area to be treated. Administration can be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the present application is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an anti-C9ORF72 RNA silencing agent of the present application directly into the brain (e.g., into the globus pallidus or the corpus striatum of the basal ganglia, and near the medium spiny neurons of the corpus striatum). In addition to an RNA silencing agent of the present application, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the present application can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the present application. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; E L Andaloussi S, Mager I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Miger I, Wood M J. (2013). Exosomes for targeted siRNA delivery across biological barriers. Adv Drug Deliv Rev. 2013 March; 65(3):391-7. doi: 10.1016/j.addr.2012.08.008).

In certain embodiments, one or more lipophilic molecules are used to allow delivery of an RNA silencing agent of the present application past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the present application. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the present application across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the present application can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids can be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the present application can be administered by any suitable method. As used herein, topical delivery can refer to the direct application of an RNA silencing agent to any surface of the body, including the eye, a mucous membrane, surfaces of a body cavity, or to any internal surface. Formulations for topical administration can include transdermal patches, ointments, lotions, creams, gels, drops, sprays, and liquids. Conventional pharmaceutical carriers, aqueous, powder or oily bases, thickeners and the like can be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration can include sterile aqueous solutions which can also contain buffers, diluents and other suitable additives. Compositions for intrathecal or intraventricular administration do not include a transfection reagent or an additional lipophilic moiety besides, for example, the lipophilic moiety attached to the RNA silencing agent.

Formulations for parenteral administration can include sterile aqueous solutions which can also contain buffers, diluents and other suitable additives. Intraventricular injection can be facilitated by an intraventricular catheter, for example, attached to a reservoir. For intravenous use, the total concentration of solutes should be controlled to render the preparation isotonic.

An RNA silencing agent of the present application can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that can be readily formulated as dry powders. An RNA silencing agent composition can be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers can be in a crystalline or amorphous form or can be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the present application can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

VIII. Kits

In certain other aspects, the present application provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation can be provided in one container. Alternatively, it can be desirable to provide the components of the pharmaceutical formulation separately in two or more containers, e.g., one container for an RNA silencing agent preparation, and at least another for a carrier compound. The kit can be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein can be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Figure 2:
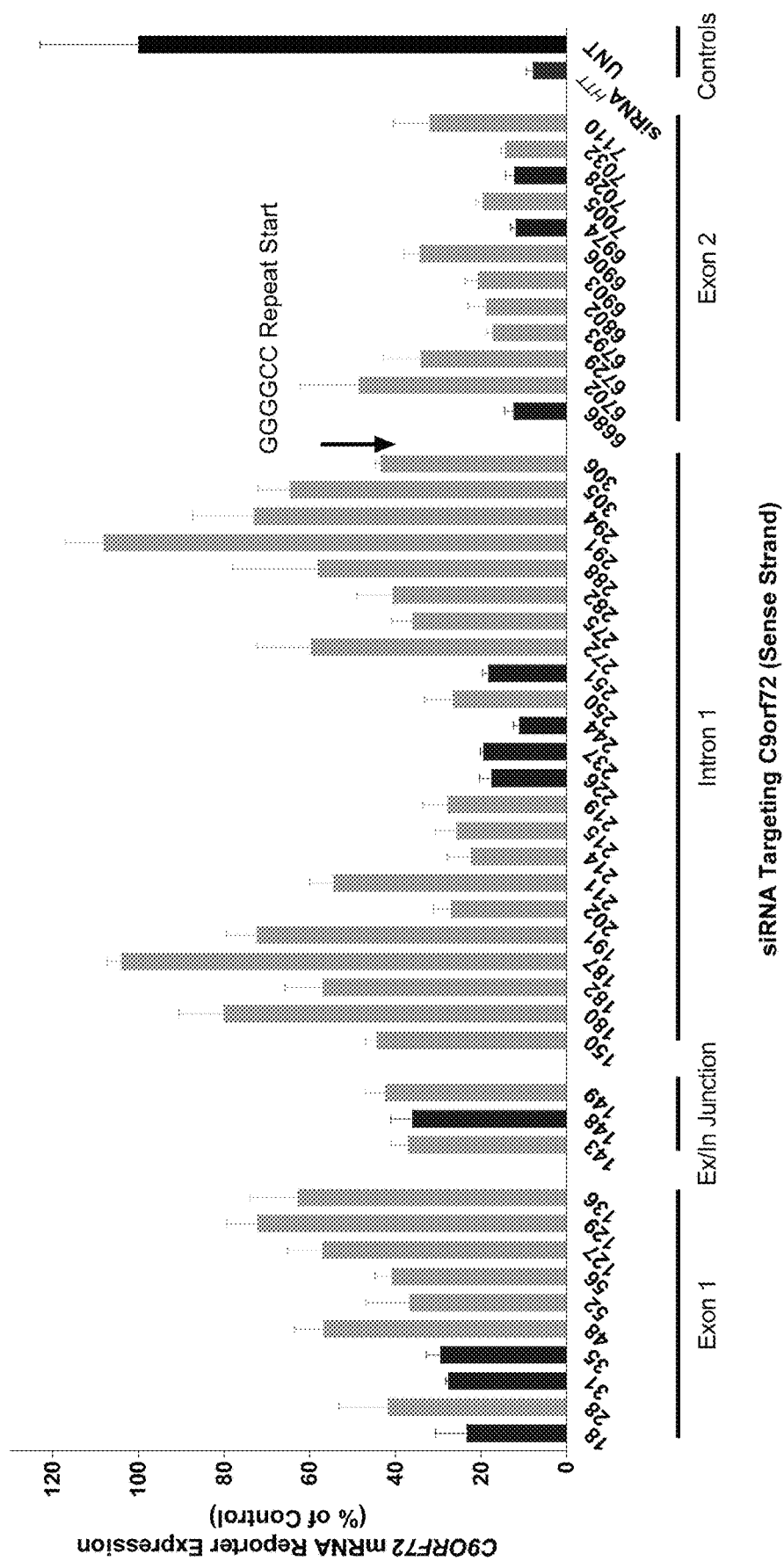
FIG. 2 is a graphical depiction of the results for the systematic screen of C9orf72 sense strand targeting siRNA (1.5 µM) molecules, using the psiCHECK2 system over 72 hours in HeLa cells. Candidates to the selective targeting region spanning exon1/intron1, as well as the non-selective region of exon 2 were tested. Knockdown was measured in cells by fluorescence detection of luciferase reporter relative to control untreated cells. Robust knockdown was observed with three candidates in exon 1, one candidate at the junction between exon 1 and intron 1, four candidates in intron 1, and three candidates in exon 2.
Figure 3:
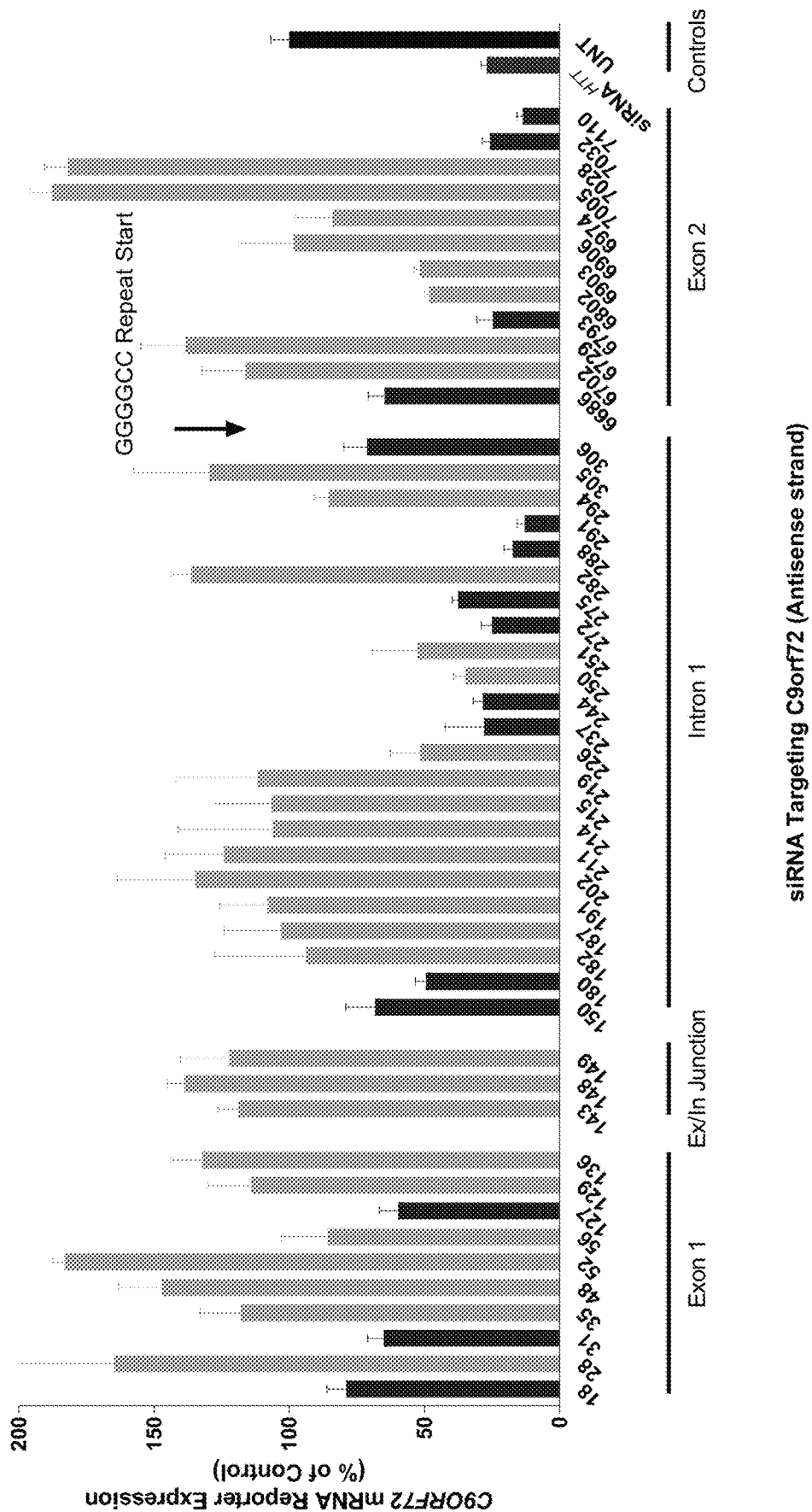
FIG. 3 is a graphical depiction of the results for the systematic screen of C9orf72 antisense strand targeting siRNA (1.5 µM) molecules, using the psiCHECK2 system over 72 hours in HeLa cells. Candidates to the selective targeting region spanning exon1/intron1, as well as the non-selective region of exon 2 were tested. Knockdown was measured in cells by fluorescence detection of luciferase reporter relative to control untreated cells. Robust knockdown was observed with three candidates in exon 1, nine candidates in intron 1, and 4 candidates in exon 2.

Example 1. Systematic Screen to Identify Functional siRNA Targeting C9orf72 in the Non-Selective Region Candidate C9orf72 functional siRNA were screened as follows. C9orf72 reporter plasmids were inserted into the psiCHECK2 system in HeLa cells. siRNA was applied at a concentration of 1.5 µM. After 72 hours, samples were analyzed by DualGlo assay for reporter expression knockdown. As shown in FIGS. 2 and 3, sense and antisense candidates were identified in each of the regions of Exon1, the Exon 1/Intron 1 junction, Intron 1, and Exon 2.

Figure 4:
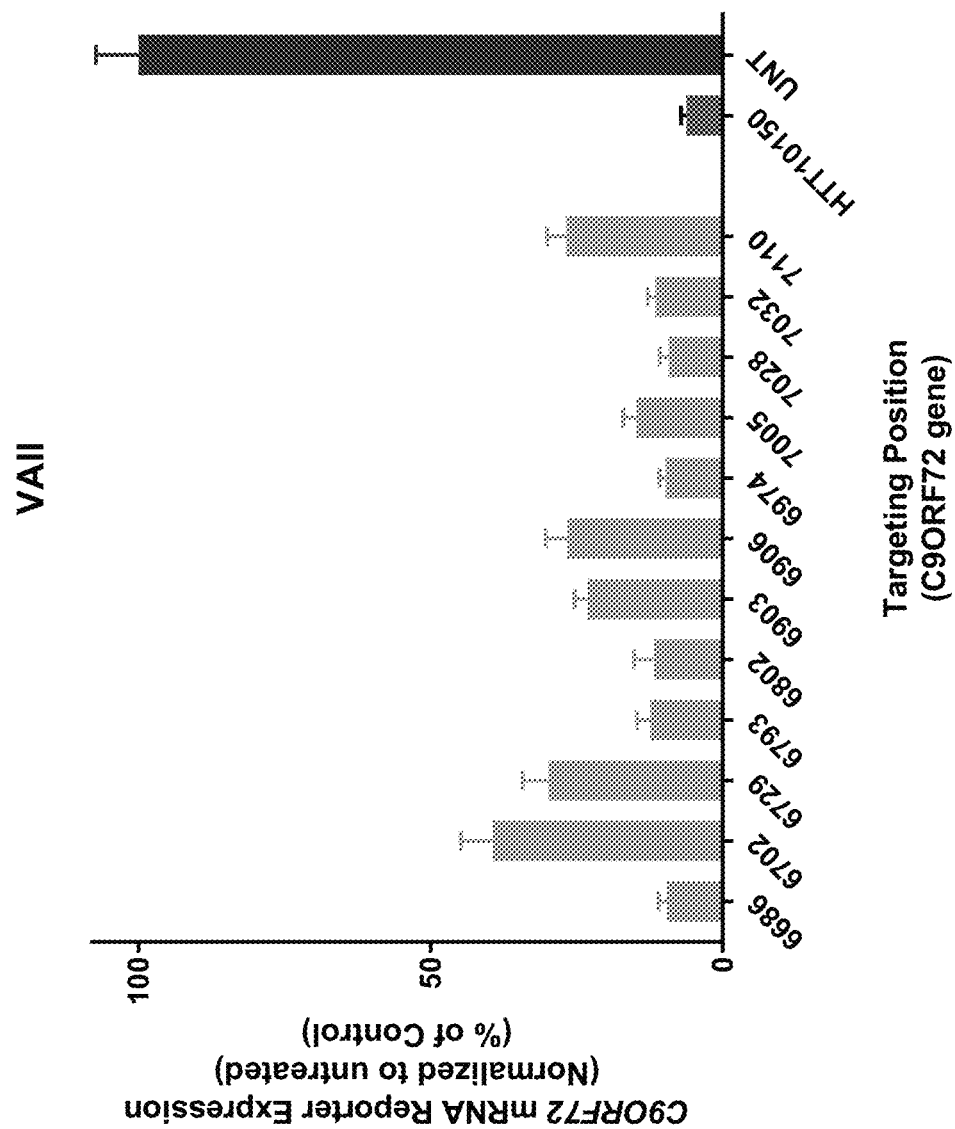
FIG. 4 is a graphical depiction of the results for the systematic screen of C9orf72 sense strand targeting siRNA (1.5 µM) molecules within the non-selective region of exon 2. Knockdown was measured in cells by fluorescence detection of luciferase reporter relative to control untreated cells.
Figure 5:
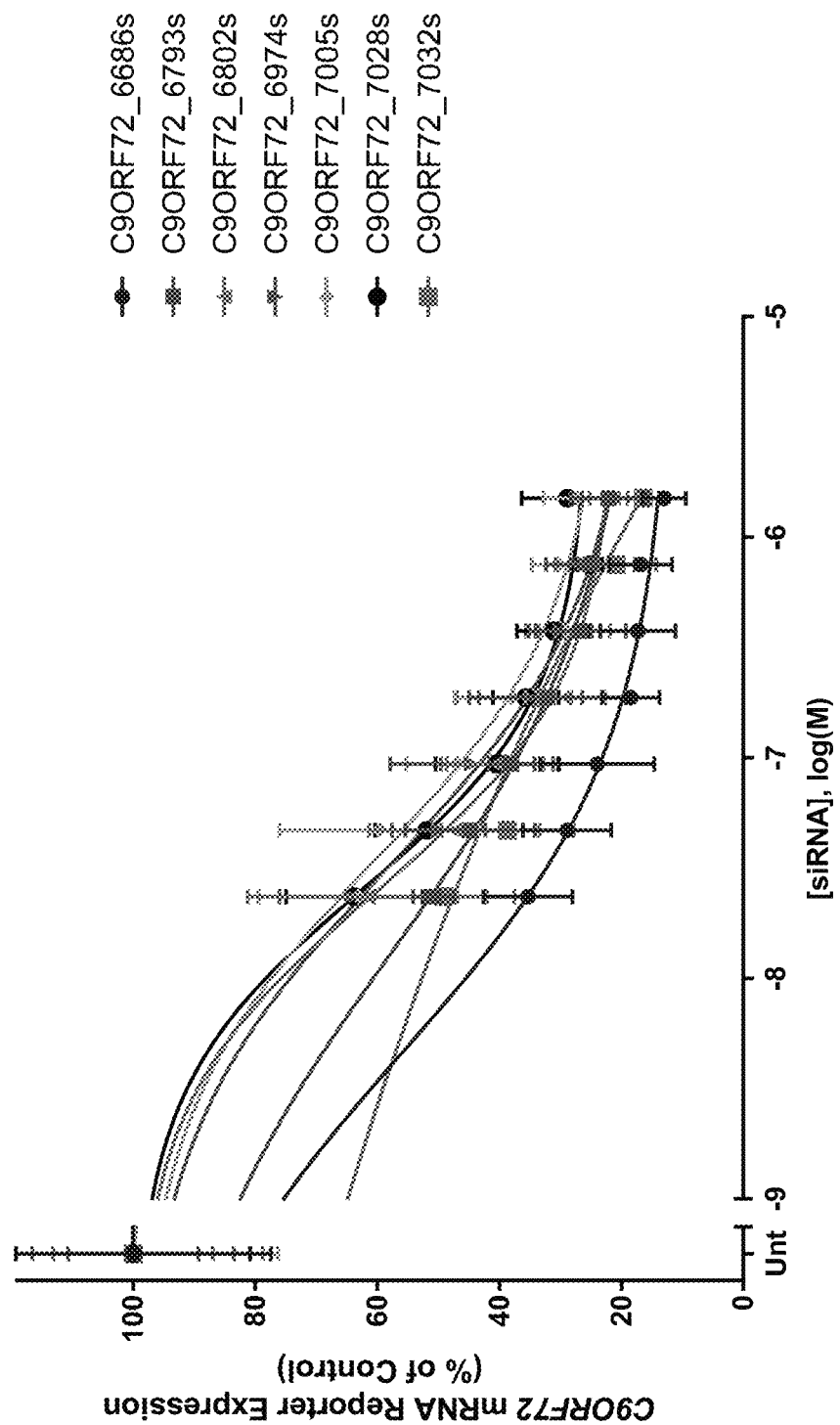
FIG. 5 depicts concentration-response curves obtained by luciferase reporter assay for seven candidate, non-selective, C9orf72 sense targeting siRNA molecules. Results were obtained using the psiCHECK2 system at varying concentrations of siRNA in HeLa cells using the DualGlo Assay. Knockdown was measured in cells by fluorescence detection of luciferase reporter relative to control untreated cells. The results allowed to establish IC50 inhibitory values for the tested molecules.
Figure 6:
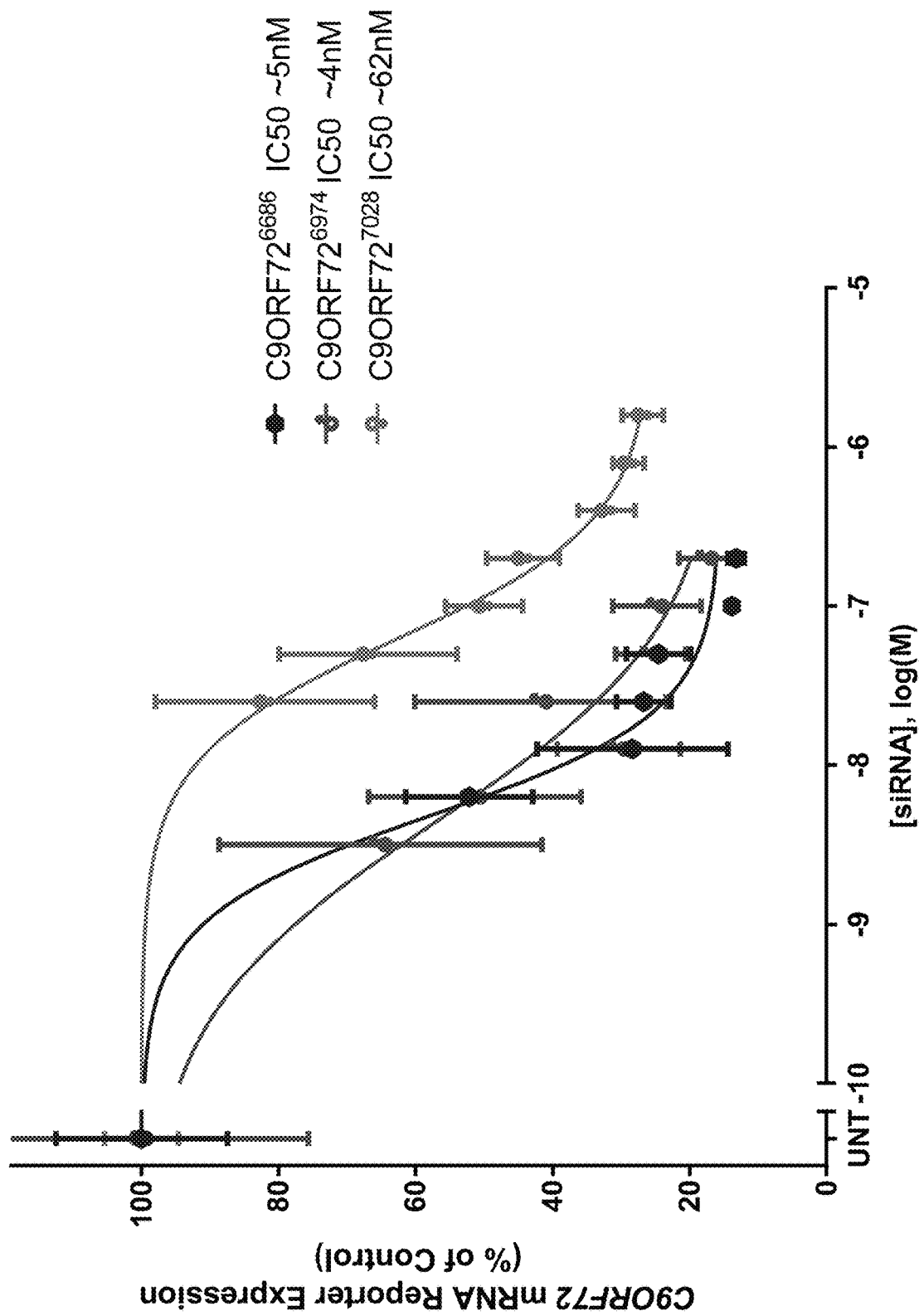
FIG. 6 depicts concentration-response curves obtained by luciferase reporter assay for three candidate siRNA molecules to determine IC50 inhibitory values. Results were obtained using the psiCHECK2 system at varying concentrations of siRNA in HeLa cells using the DualGlo Assay. Knockdown was measured in cells by fluorescence detection of luciferase reporter relative to control untreated cells.

Candidate siRNA molecules were then tested with increasing doses of siRNA in the Luciferase reporter assay. Functional candidates were identified, as illustrated in FIG. 4. IC50 values for three candidate molecules were calculated as seen in FIG. 5. Candidate 6686 exhibited an IC50 of ~5 nM, candidate 6974 exhibited an IC50 of ~4 nM, and candidate 7028 exhibited an IC50 of ~62 nM. Robust knockdown of mRNA was observed with candidates 7005 and 7032.

Figure 7:
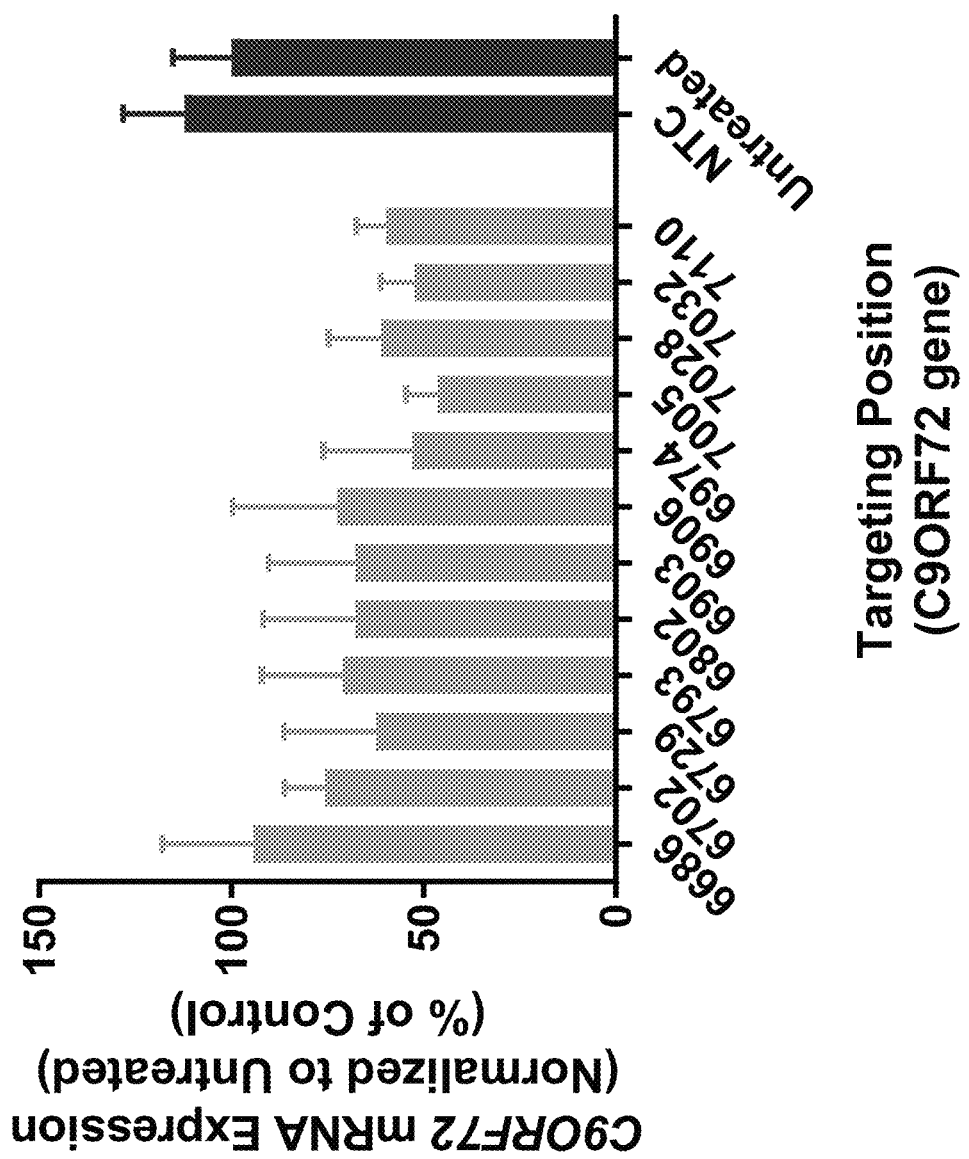
FIG. 7 depicts the results of a systematic screen in U87MG glioblastoma cells with candidate siRNA molecules targeting regions within exon 2 of C9orf72. Results were obtained by measuring levels of C9orf72 mRNA by reverse transcriptase quantitative PCR (RT-qPCR) and comparing expression to the level of expression in untreated control cells.
Figure 8:
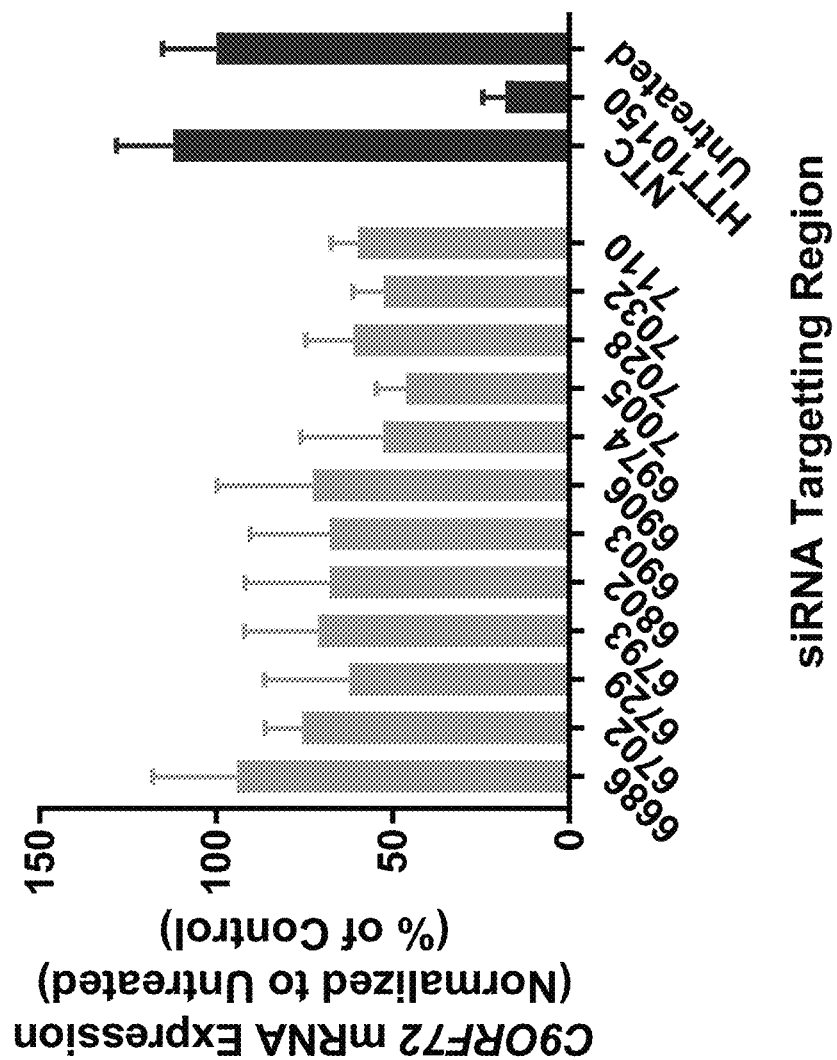
FIG. 8 depicts the mRNA levels of C9orf72 in U87MG glioblastoma cells treated with candidate siRNA molecules. Results were obtained using qPCR. mRNA levels are displayed as a percentage of control untreated cells.

To determine the effect of candidate siRNA molecules on live cells, U87MG glioblastoma cells were exposed to different siRNA molecules, and mRNA levels were assessed by qPCR. Levels of C9orf72 mRNA were compared to untreated control cells, as seen in FIGS. 7 and 8.

Figure 9:
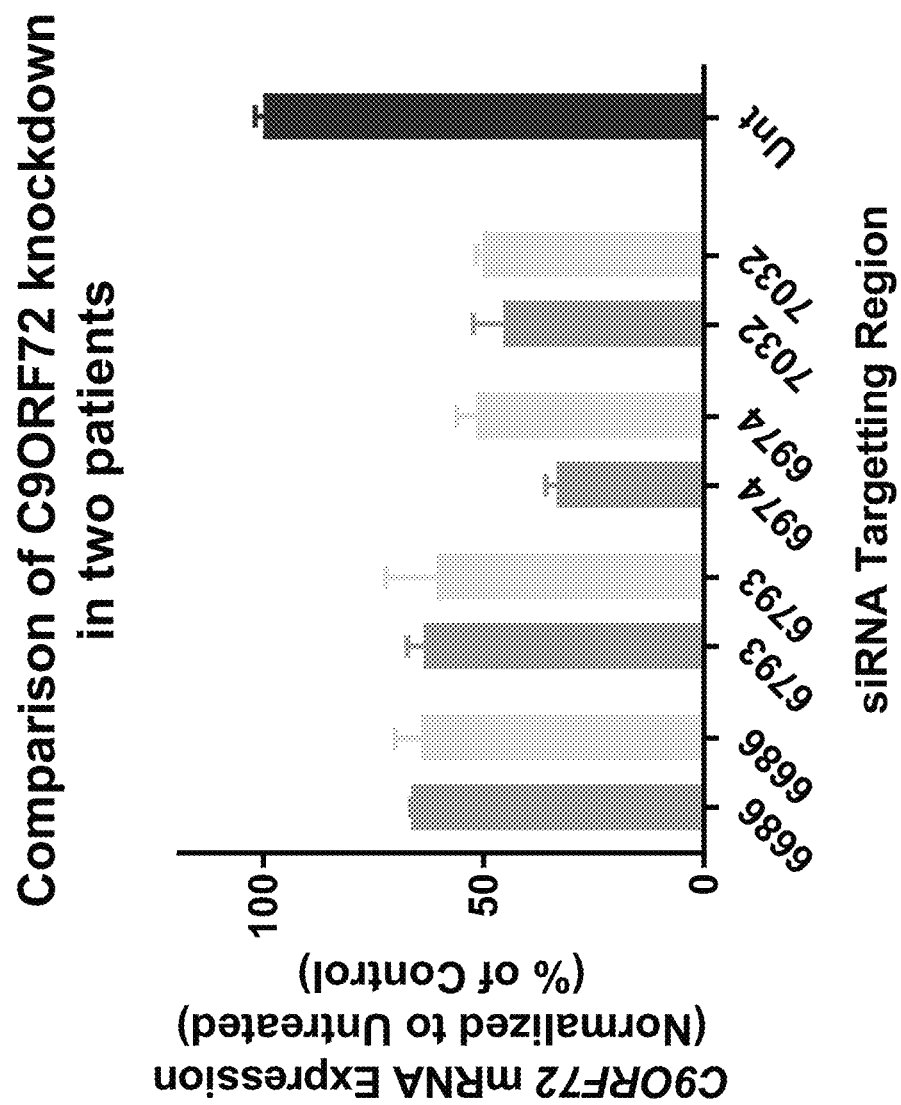
FIG. 9 depicts the mRNA levels of C9orf72 in cultured fibroblasts from two C9-ALS patients. mRNA levels were quantified using qPCR and compared to untreated control levels. C9.2 and C9.3 patient fibroblasts displayed knockdown in C9orf72 expression in all selected candidates.

Four candidate siRNA molecules were tested for efficacy in C9 ALS patient fibroblasts from two patients. mRNA levels were assessed by RT-qPCR in C9.2 and C9.3 patient fibroblasts after treatment with siRNA and compared to untreated controls. Robust knockdown of C9orf72 mRNA was observed in both patient fibroblast lines across all four candidate molecules, as displayed in FIG. 9.

Figure 11A:
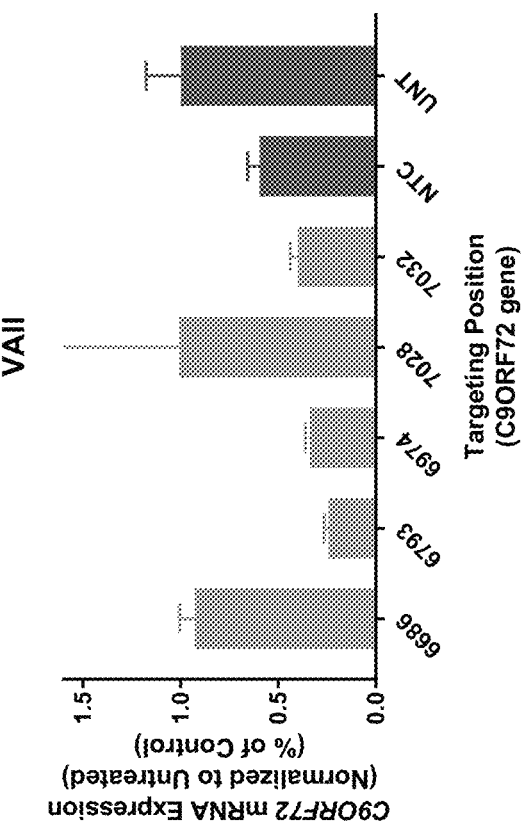
FIG. 11A-FIG. 11B depict the mRNA levels of C9orf72 in a mouse model of Amyotrophic Lateral Sclerosis after treatment with siRNA knockdown molecules, compared to untreated controls. Robust knockdown was observed in multiple candidates.
Figure 11B:
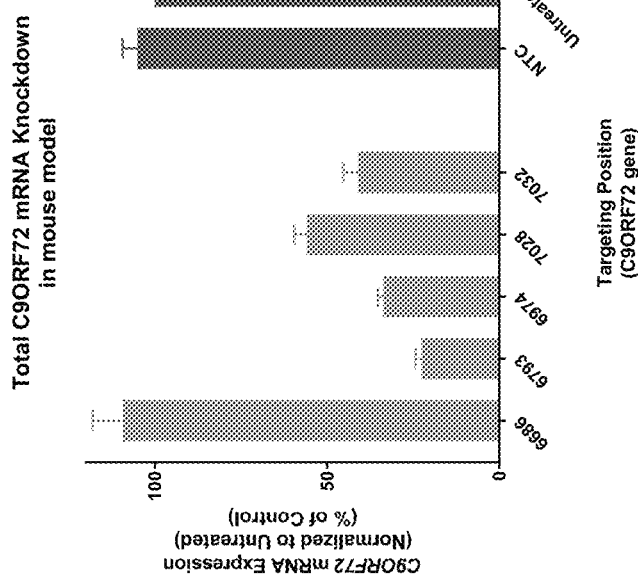

Five candidate molecules were then tested in a transgenic ALS model mice carrying a bacterial artificial chromosome (BAC) containing the full human C9orf72 gene with either a normal allele (15 repeats) or disease-associated expansion (~100-1000 repeats; C9-BACexp). ALS mice were treated with siRNA, sacrificed, and RNA was extracted from spinal cord tissue. Levels of C9orf72 mRNA were then assessed by qPCR and compared to untreated controls, as seen in FIG. 11. Robust knockdown of C9orf72 transcript was observed consistently in three candidate molecules across multiple experiments.

Figure 16:
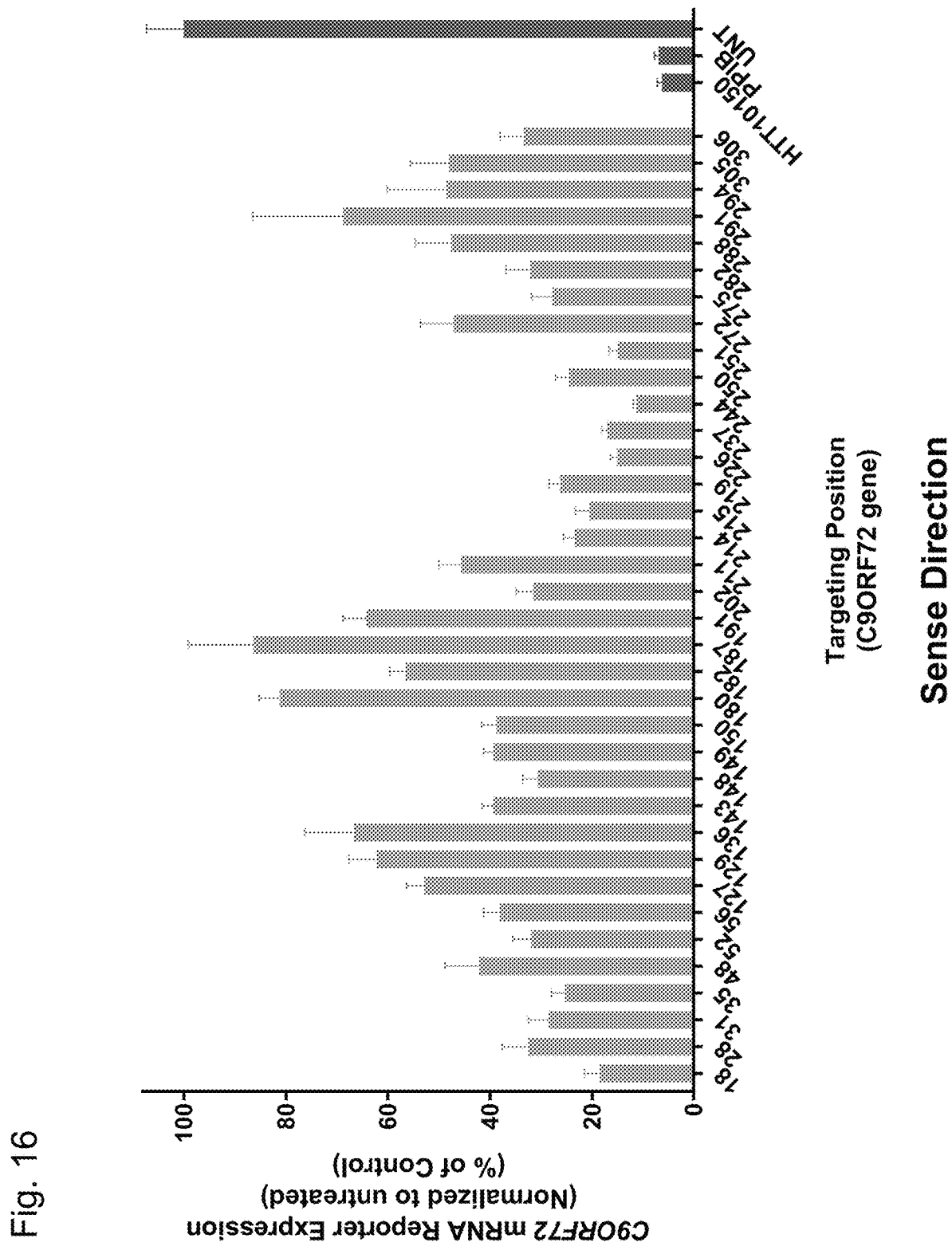
FIG. 16 depicts the results of a luciferase reporter assay for candidate selective, C9orf72 sense-strand targeting siRNA (1.5 µM) molecules within exon 1a and intron 1 of C9orf72. Knockdown was measured in cells by fluorescence detection of luciferase reporter relative to control untreated cells.

Example 2. Systematic Screen to Identify Functional siRNA Targeting C9orf72 in the Selective Region Candidate C9orf72 functional siRNAs were screened as follows. C9orf72 reporter plasmids were inserted into the psiCHECK2 system in HeLa cells. siRNA was applied at 1.5 µM. After 72 hours, samples were analyzed by DualGlo assay for reporter expression knockdown. As shown in FIG. 16, candidates were identified in the regions spanning exon 1 and intron 1. Knockdown was observed to be most robust for candidate 244.

Figure 17:
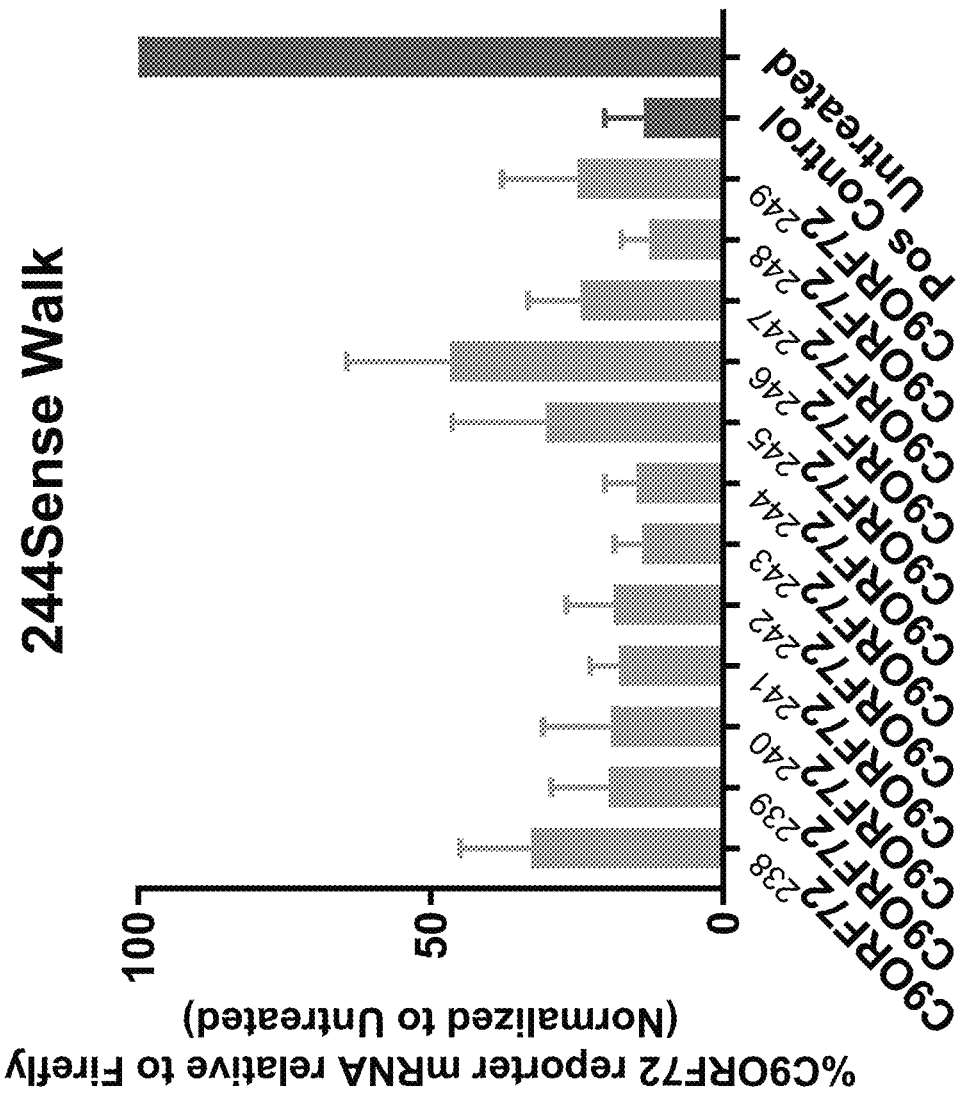
FIG. 17 depicts the results of a "sense-walk" experiment targeting individual regions between nucleotides 238 and 249 on the sense strand of C9orf72. Knockdown was measured in cells by fluorescence detection of luciferase reporter relative to control untreated cells.

A "sense walk" experiment was carried out to determine knockdown of additional candidate molecules within the selective region adjacent to candidate 244. Reporter expression was analyzed as described above. Candidate molecules were developed targeting nucleotide regions. Regions starting at nucleotide 238, 239, 240, 241, 242, 243, 244, 245, 246, 247, 248 or 249 and ending 20 nucleotides downstream were examined, and results are displayed in FIG. 17. Robust knockdown was observed among all candidates compared to untreated control reporter expression.

Figure 18A:
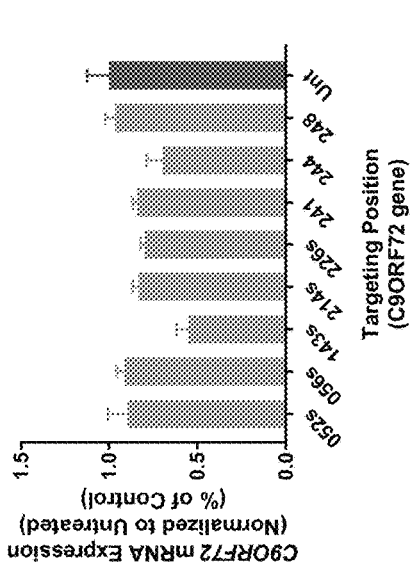
FIG. 18A-FIG. 18C depict the levels of total mRNA (all variants) expression from two C9ALS patient cultured fibroblasts after siRNA treatment.
Figure 18B:
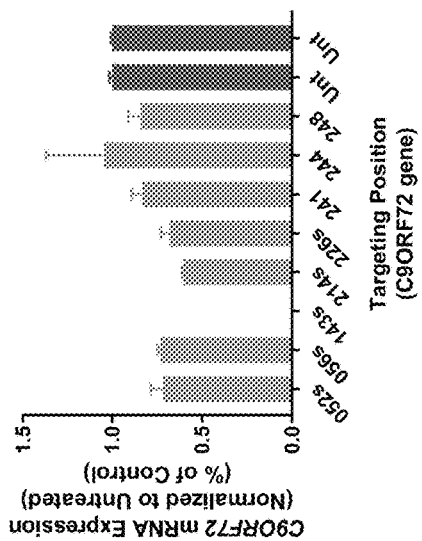
Figure 18C:
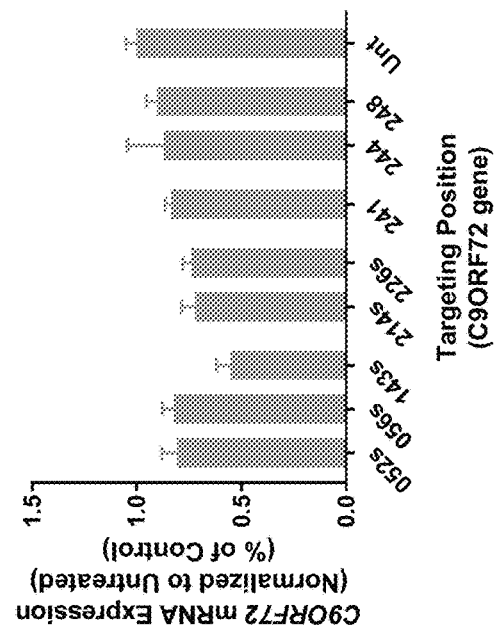
Figure 19:
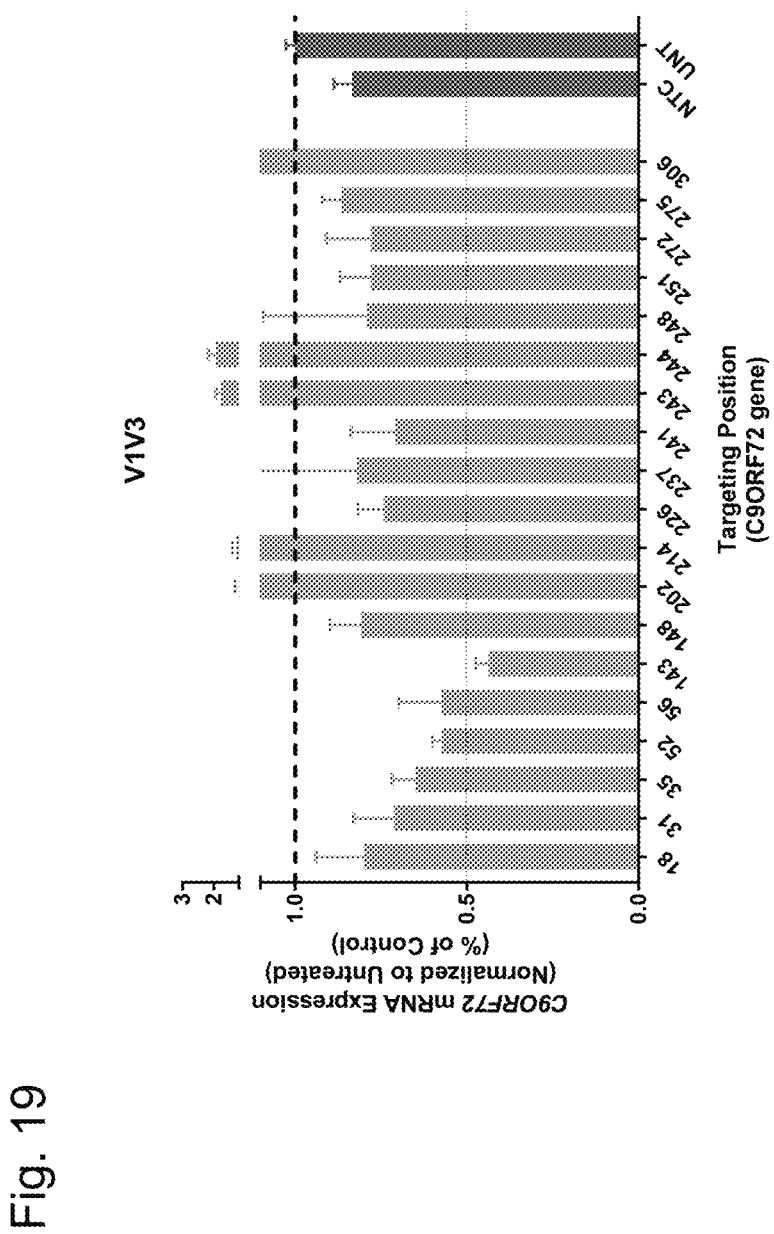
FIG. 19 depicts the level of C9orf72 Variant 1 and Variant 3 mRNA expression in cultured neurons treated with siRNA in the selective region from a C9orf72 Amyotrophic Lateral Sclerosis mouse model. Levels of mRNA were quantified and compared to control untreated neurons with qPCR.
Figure 20:
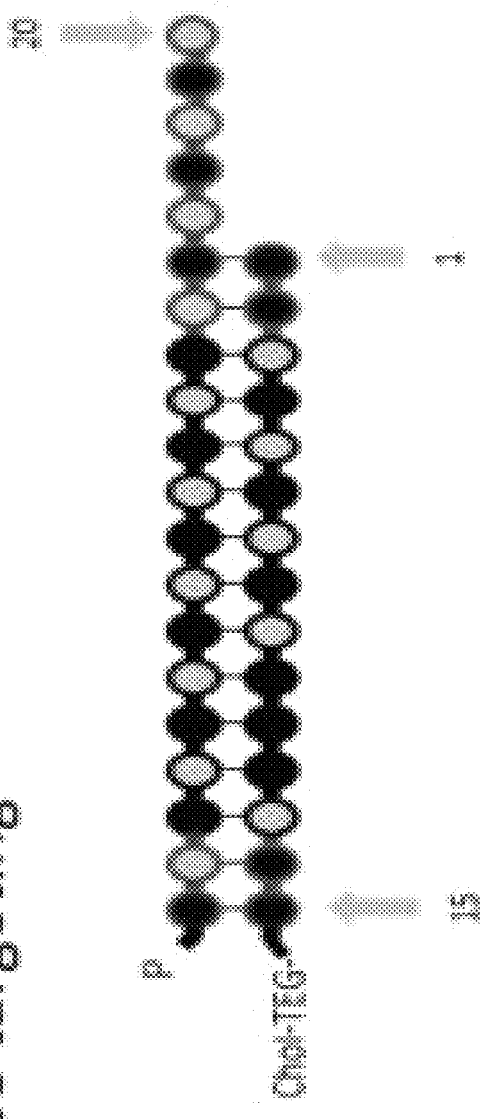
FIG. 20 depicts a dsRNA molecule for screening antisense strands with an alternating 2'O-methyl modification (black) and a 2'-Fluoro-ribonucleotide modification (gray) at all positions except positions 1 and 15 from the 5' end of the passenger strand, with a cholesterol moiety attached to the terminal nucleotide at the 3' end of the passenger strand. The red dashes indicate phosphorothioate bonds.
Figure 21:
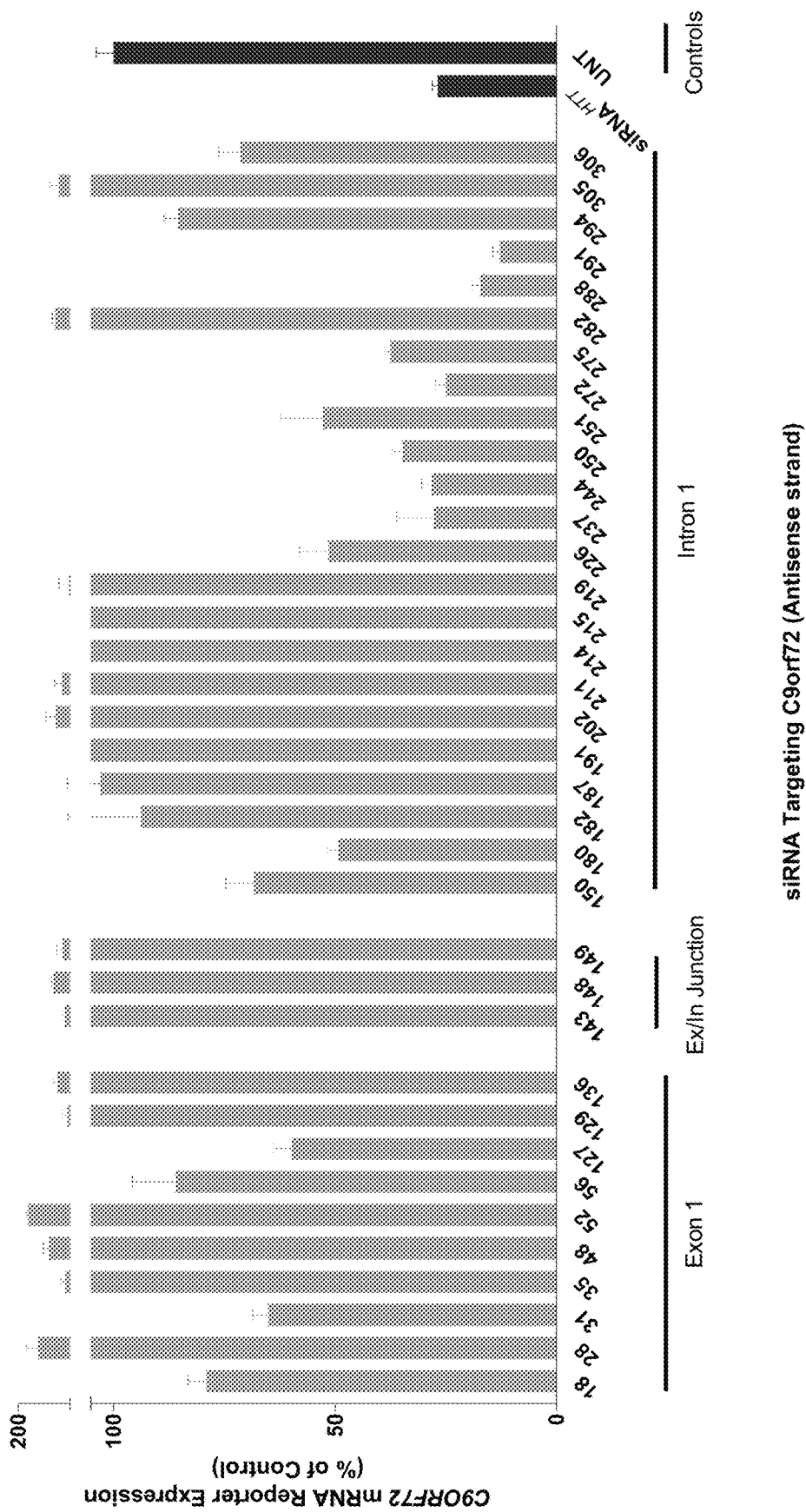
FIG. 21 is a graphical depiction of the results for the systematic screen of C9orf72 antisense strand targeting siRNA (1.5 µM) molecules, using the psiCHECK2 system over 72 hours in HeLa cells. Candidates to the selective targeting region spanning exon1/intron1 were tested. Knockdown was measured in cells by fluorescence detection of luciferase reporter relative to control untreated cells. Robust knockdown was observed with multiple candidates.
Figure 22:
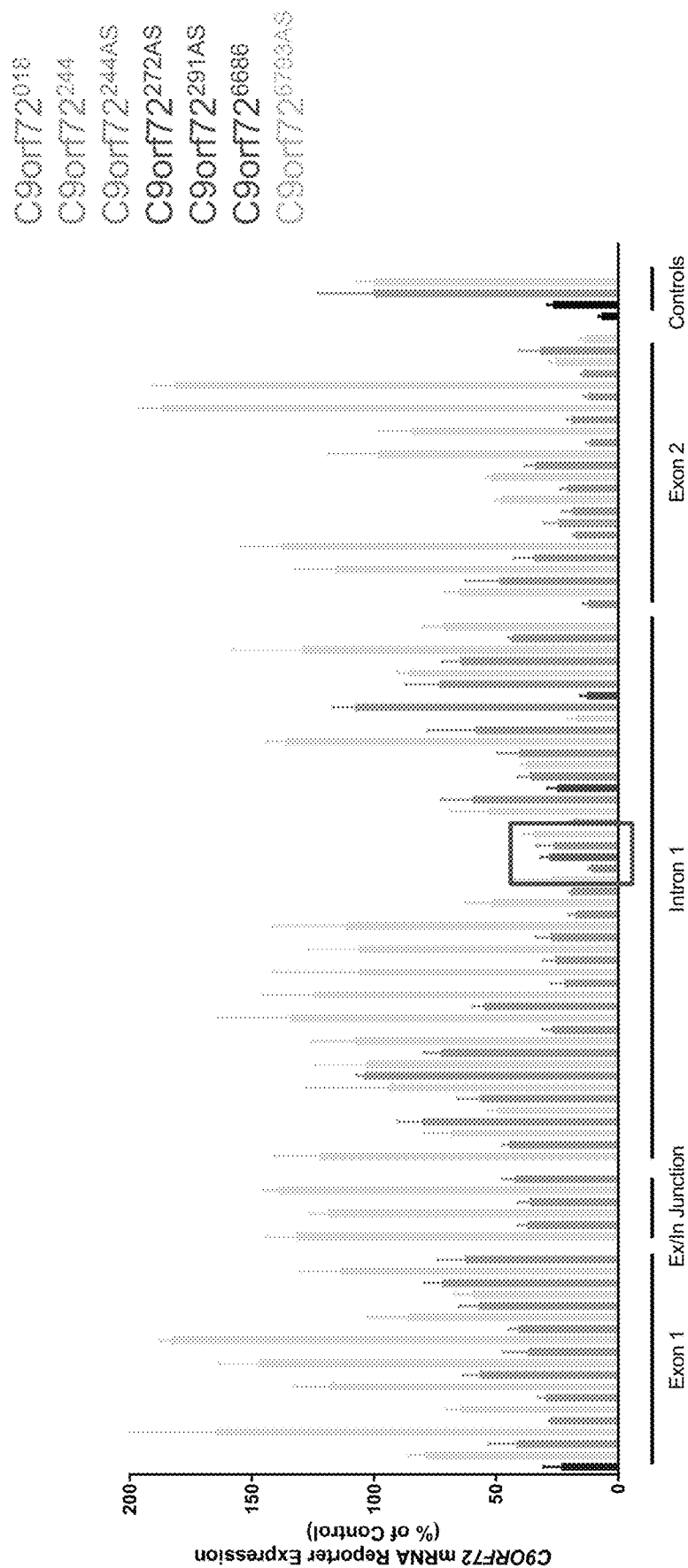
FIG. 22 depicts the common productive silencing region for the C9orf72 targeting siRNA in both sense and antisense directions. Results were obtained using the psiCHECK2 system over 72 hours in HeLa cells. Knockdown was measured in cells by fluorescence detection of luciferase reporter relative to control untreated cells.
Figure 23:
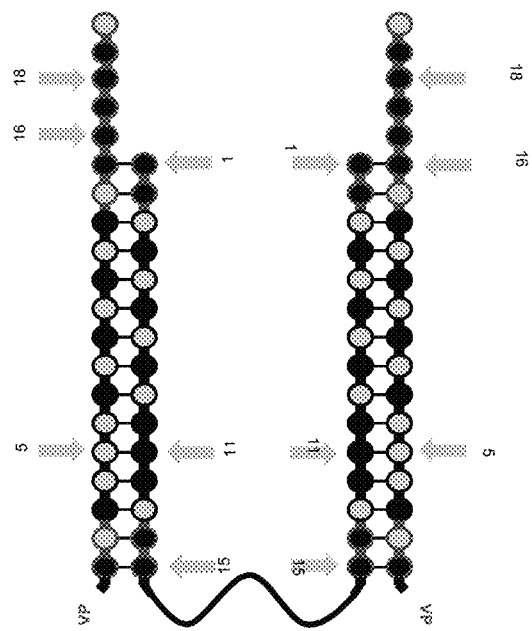
FIG. 23 depicts a schematic of a di-siRNA molecule. Black—2'-O-methyl, grey—2'-fluoro, red dash—phosphorothioate bond, linker attached to terminal nucleotide of 3'end of each passenger strand. The motif of alternating nucleotide modifications varies at positions 1, 11 and 15 of the sense targeting strand from the 5' end and at positions 5, 16, and 18 of the complimentary, linked strands from the 5'end.

Selective targeting candidates were tested in C9 ALS patient fibroblast lines C9.2 (FIG. 18A) and C9.3 (FIG. 18B). C9 patient fibroblasts were treated with siRNA of 8 different candidate molecules. RNA was extracted and total mRNA (all variants) levels of C9or72 were then assessed by qPCR. Pooled results from both patient lines are displayed in FIG. 18C. Significant reduction of mRNA was observed in several candidate molecules, including 52s, 56s, 143s, 214s, 226s, and 241.

Figure 10:
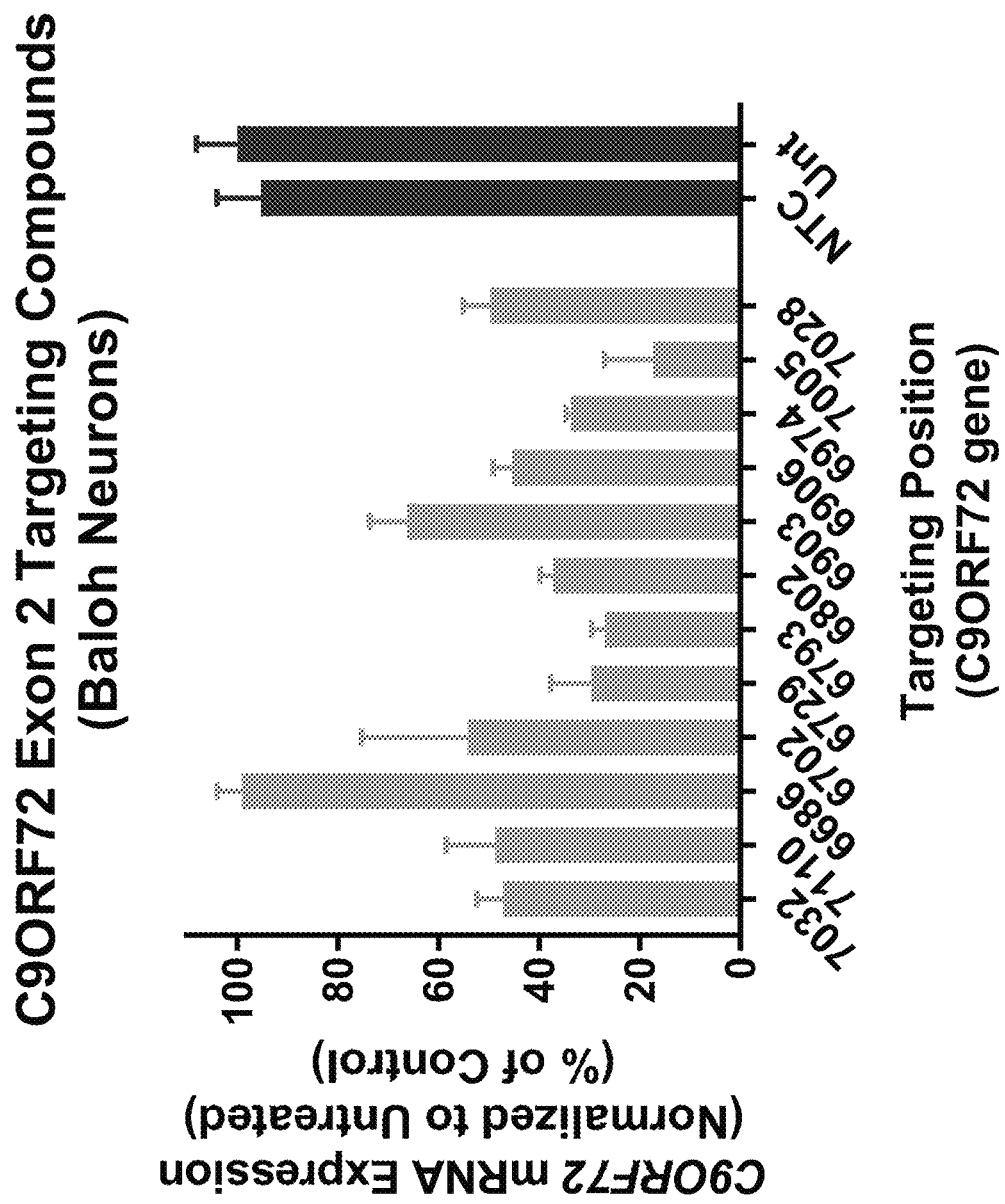
FIG. 10 depicts the mRNA levels from cultured neurons of a C9ALS mouse model targeting candidate regions in C9orf72 exon 2. mRNA levels were quantified using qPCR and compared to untreated control levels.

Selective targeting candidates were tested in primary cultured neurons from C9 ALS mice (FIG. 10). Cultured neurons were treated with 19 different siRNA candidates. RNA was extracted and mRNA levels of C9orf72 were then assessed by qPCR. Robust knockdown was observed in 12 candidate molecules when compared to control untreated neurons.

The identified compounds downregulated relevant C9 mRNA variants, and were also able to reduce RNA foci formation in the nucleus and cytoplasm. Compounds were also effective reducing the expression of di-peptides, one of the major determinants of C9 toxicity.

Example 3. RNA Foci Result from Expansion of RNA Repeats

Figure 12A:
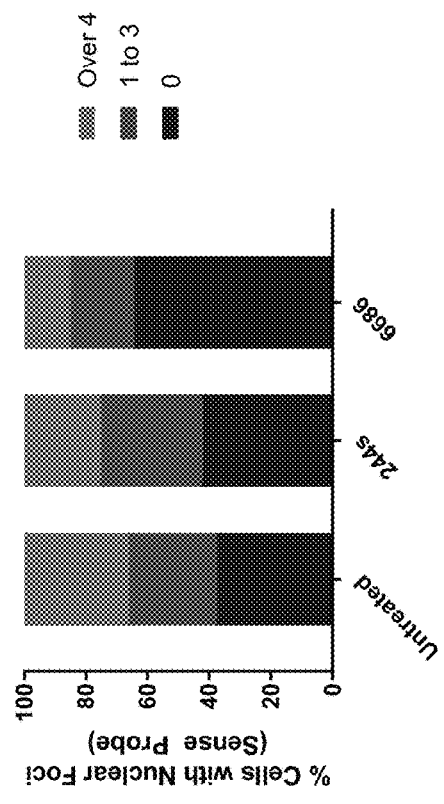
FIG. 12A-FIG. 12D visually depict the reduction in nuclear and cytoplasmic foci in cultured patient fibroblasts of two representative candidates compared to the control untreated cells.
Figure 12B:
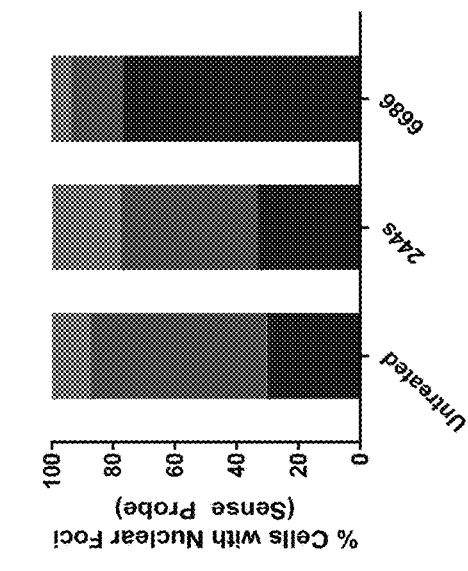
Figure 12C:
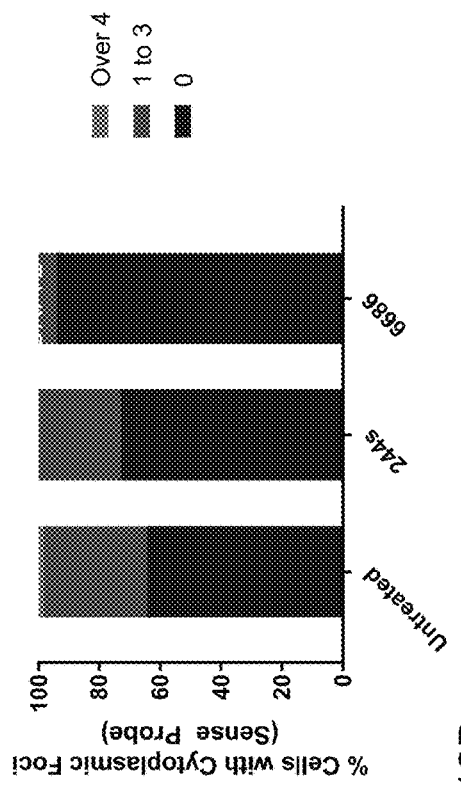
Figure 12D:
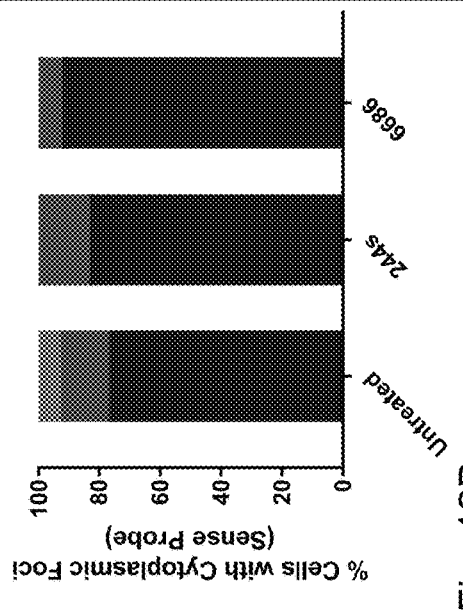
Figure 14:
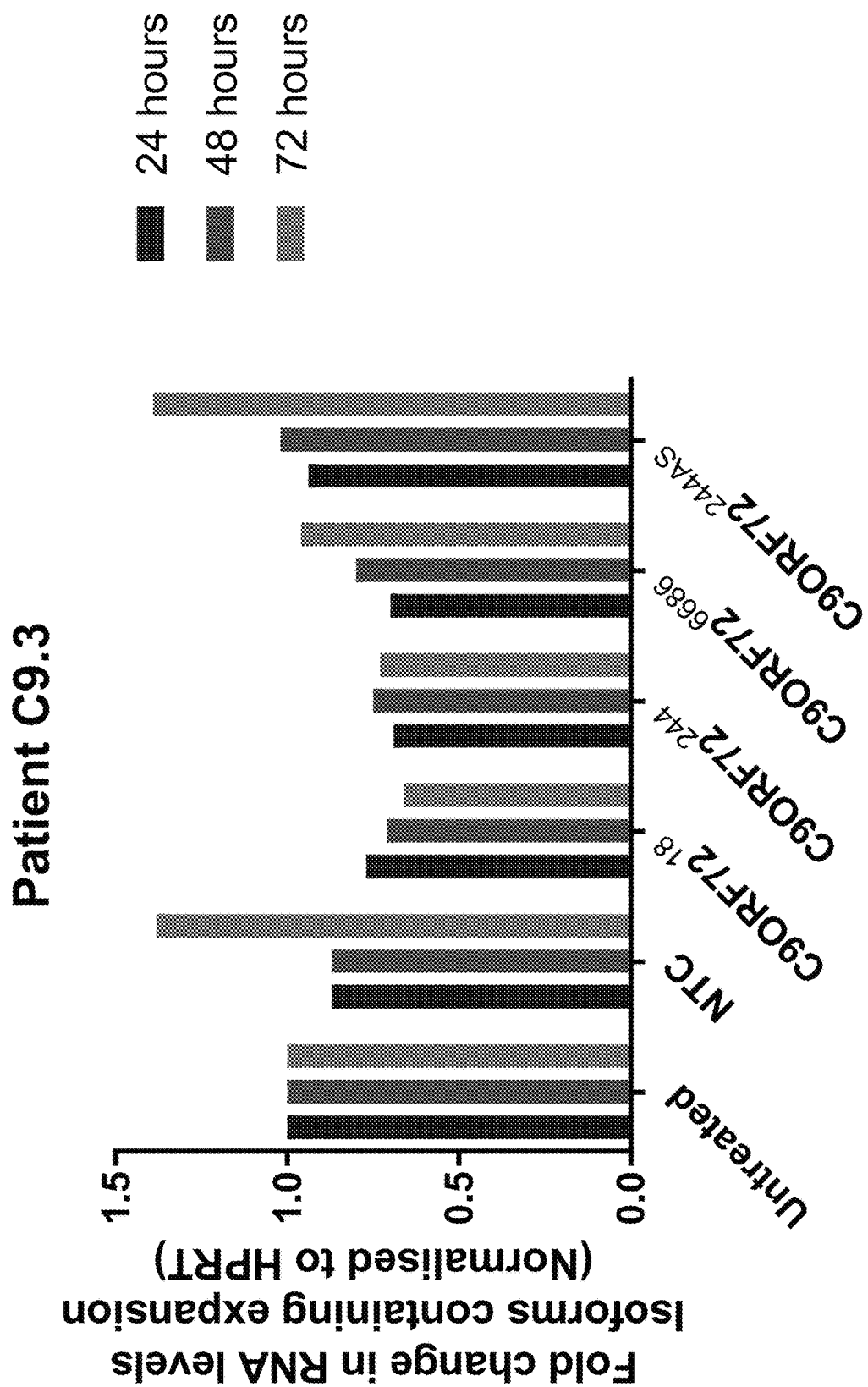
FIG. 14 depicts the fold change in RNA levels of isoforms containing expansions in Patient C9.3 fibroblasts treated with candidate siRNA molecules for 24, 48, and 72 hours. RNA levels were measured by qPCR, normalized to hypoxanthine phosphororibosyltransferase, and compared to control untreated cells.
Figure 15:
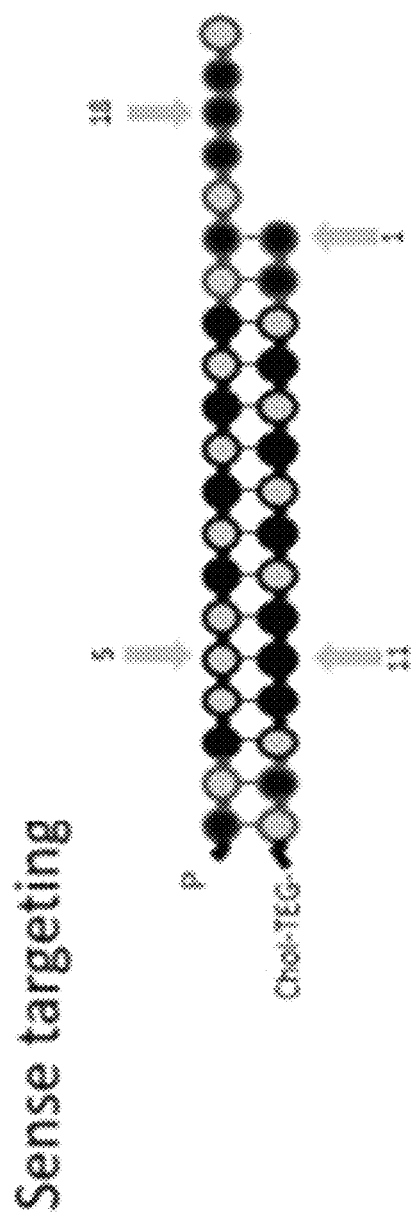
FIG. 15 depicts a dsRNA molecule for screening sense strands with an alternating 2'O-methyl modification and a 2'-Fluoro-ribonucleotide modification at all positions except positions 5 and 18 of the guide strand and positions 1 and 11 from the 5' end of the passenger strand, with a cholesterol moiety attached to the terminal nucleotide at the 3' end of the passenger strand.

Candidate C9orf72 sense targeting probes were tested for their capability of increasing the percentage of cells which contained no nuclear or cytoplasmic foci. Fibroblasts from two C9 human patients were screened using these candidates. Candidate probes 244s and 6686 were tested in Patient C9.2 and Patient C9.3. An increase in the percentage of cells with no nuclear (FIG. 12A) and no cytoplasmic (FIG. 12B) foci was observed when Patient C9.2 fibroblasts were treated with 6686 siRNA probe when compared to untreated patient fibroblasts. An increase in the percentage of cells with no nuclear (FIG. 12C) and no cytoplasmic (FIG. 12D) foci was observed when Patient C9.3 cells were treated with either siRNA probe 244s or 6686 when compared to untreated patient fibroblasts. Images of Patient C9.3 cells display the reduction of nuclear foci between untreated (FIG. 13A) and siRNA probe 6686 treated (FIG. 13B) cells.

Example 4. Reduction in Isoforms

The presence of expansion-bearing isoforms of C9orf72 mRNA was assessed in Patient C9.3 fibroblasts treated with various candidate siRNA probes normalized to hypoxanthine phosphoribosyltransferase and compared to untreated control cells. A reduction of levels of mRNA of isoforms containing expansion repeats was observed at 24, 48, and 72 hours post-treatment for cells treated with candidate probes $C9orf72^{18}$ and $C9orf72^{244}$. A reduction of levels of mRNA of isoforms containing expansion repeats was observed at 24 and 48 hours for cells treated with candidate probe $C9orf72^{6686}$. A reduction of levels of mRNA of isoforms containing expansion repeats was observed at 24 hours with candidate probe $C9orf72^{244AS}$.

Example 5. Dual Targeting Sense and Antisense Transcripts

Figure 26B:
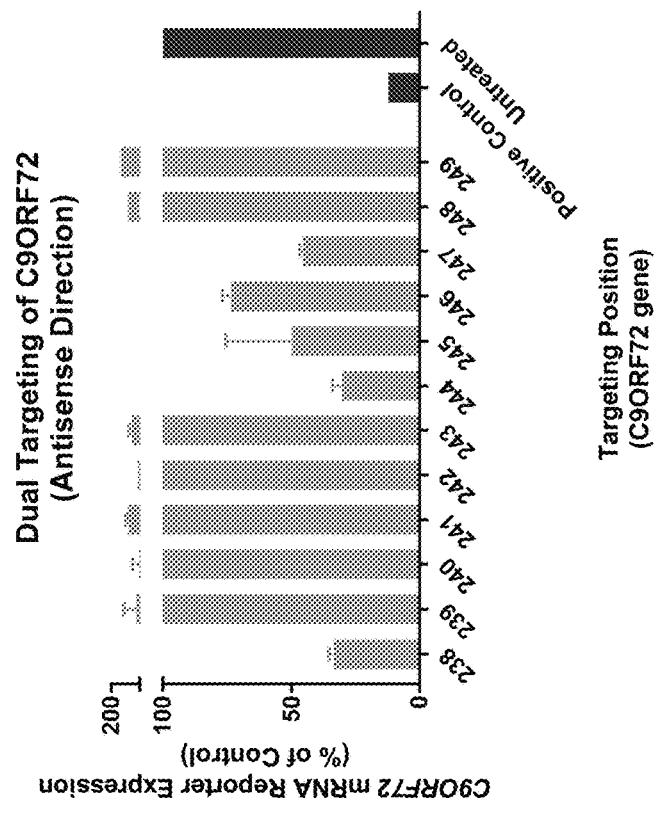
FIG. 26A-FIG. 26B is a graphical depiction of the results for the systematic screen of dual-acting RNA silencing agents in an assay measuring C9orf72 sense transcript depletion (FIG. 26A) and antisense transcript depletion (FIG. 26B). The dual-acting RNA silencing agents (1.5 µM) were tested using the psiCHECK2 system over 72 hours in HeLa cells.
Figure 26A:
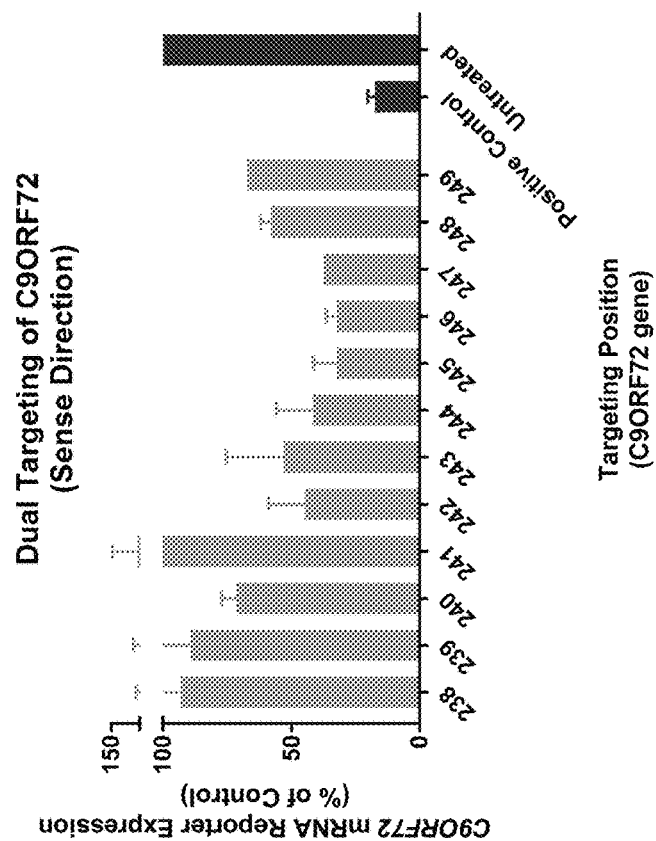

Targeting of sense and antisense transcripts with RNA silencing agents having dual targeting capabilities was assessed in a luciferase reporter assay. The dual-acting RNA silencing agents were formed with oligonucleotides synthesized to target both sense and antisense sequences within the region identified above as the "244 Sense Walk" of FIG. 17. C9orf72 sense and antisense reporter plasmids were inserted into the psiCHECK2 system in HeLa cells, and siRNA was applied at 1.5 µM. After 72 hours, samples were analyzed by DualGlo assay for reporter expression knockdown. Candidate regions beginning at nucleotides 238, 239, 240, 241, 242, 243, 244, 245, 246, 247, 248, or 249 and spanning 20 nucleotides were tested for both the sense and antisense strands. Robust knockdown was observed in targeting both sense (FIG. 26A) and antisense (FIG. 26B) strands.

Figure 28B:
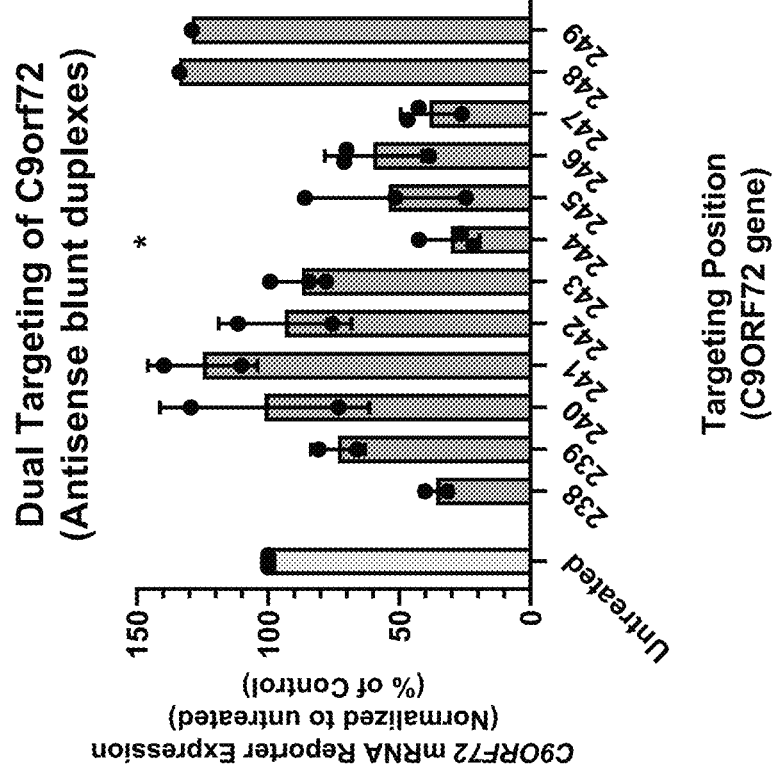
FIG. 28A-FIG. 28B is a graphical depiction of the results for the systematic screen of dual-acting RNA silencing agents including a C9orf72 sense (FIG. 28A) and antisense (FIG. 28B) strands. The dual-acting RNA silencing agents (1.5 µM) were tested using the psiCHECK2 system over 72 hours in HeLa cells.
Figure 28A:
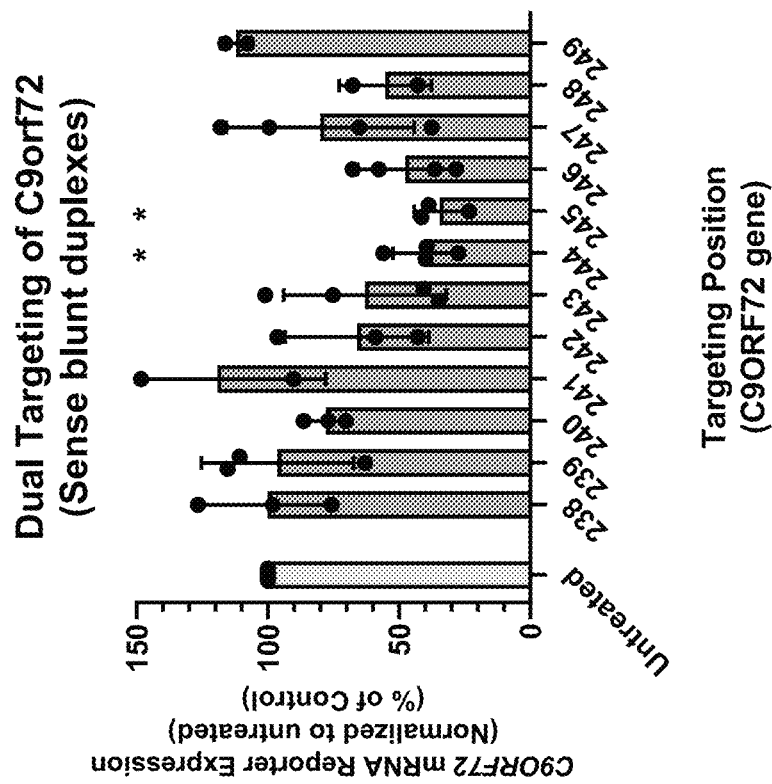

Example 6. Dual Targeting Sense and Antisense Transcripts with Blunt and Overhang-Containing Dual-Acting RNA Silencing Agents Targeting of sense and antisense transcripts with dual-targeting RNA silencing agents was assessed in a luciferase reporter assay. The dual-acting RNA silencing agents were formed with oligonucleotides synthesized to target both sense and antisense sequences within the region identified above as the "244 Sense Walk" of FIG. 17. The dual-acting RNA silencing agents, comprising a first guide strand and a second guide strand, are perfectly complementary to each other (i.e., no base pair mismatches). Schematics of the-acting RNA silencing agents are shown in FIG. 27A-FIG. 27D. C9orf72 sense and antisense reporter plasmids were inserted into the psiCHECK2 system in HeLa cells, and dual-acting RNA silencing agents were applied at 1.5 µM. After 72 hours, samples were analyzed by DualGlo assay for reporter expression knockdown. Candidate regions beginning at nucleotides 238, 239, 240, 241, 242, 243, 244, 245, 246, 247, 248, or 249 and spanning 20 nucleotides were tested for both the sense and antisense strands. Robust knockdown was observed in targeting both sense (FIG. 28A) and antisense (FIG. 28B) strands.

Figure 29:
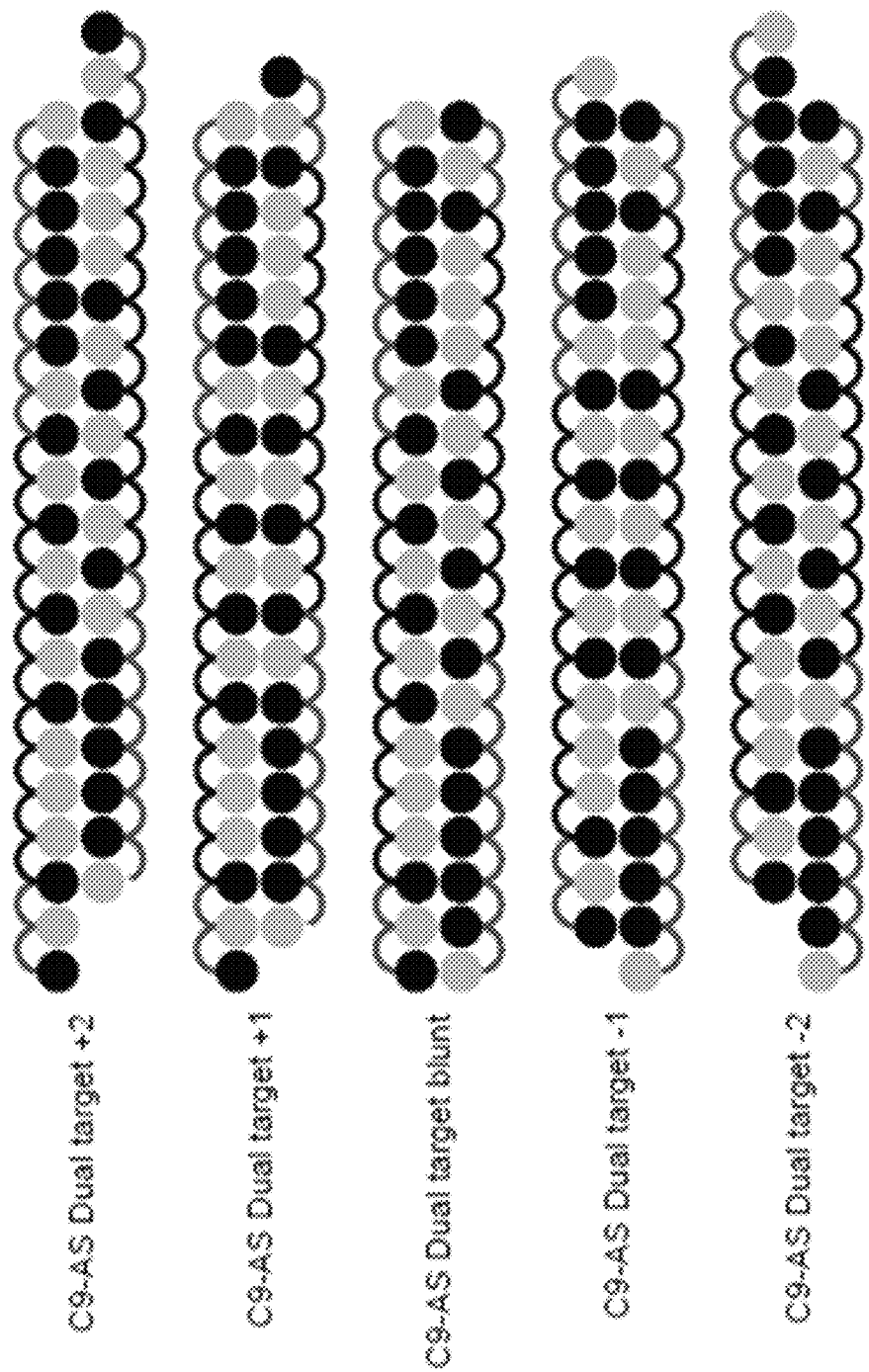
FIG. 29 depicts schematics of dual-acting RNA silencing agents with overhangs at the 5' end of the first guide strand and the second guide strand, or the 3' end of the first guide strand and the second guide strand. The schematics depict 5' end overhangs of 1 nucleotide (+1) and 2 nucleotides (+2), but 5' overhangs of up to 4 nucleotides (+4) were also made and tested. The schematics depict 3' end overhangs of 1 nucleotide (−1) and 2 nucleotides (−2), but 3' overhangs of up to 6 nucleotides (−6) were also made and tested. The overhang-containing dual-acting RNA silencing agents can be in a branched form, as shown in FIG. 27B-FIG. 27D.
Figure 30:
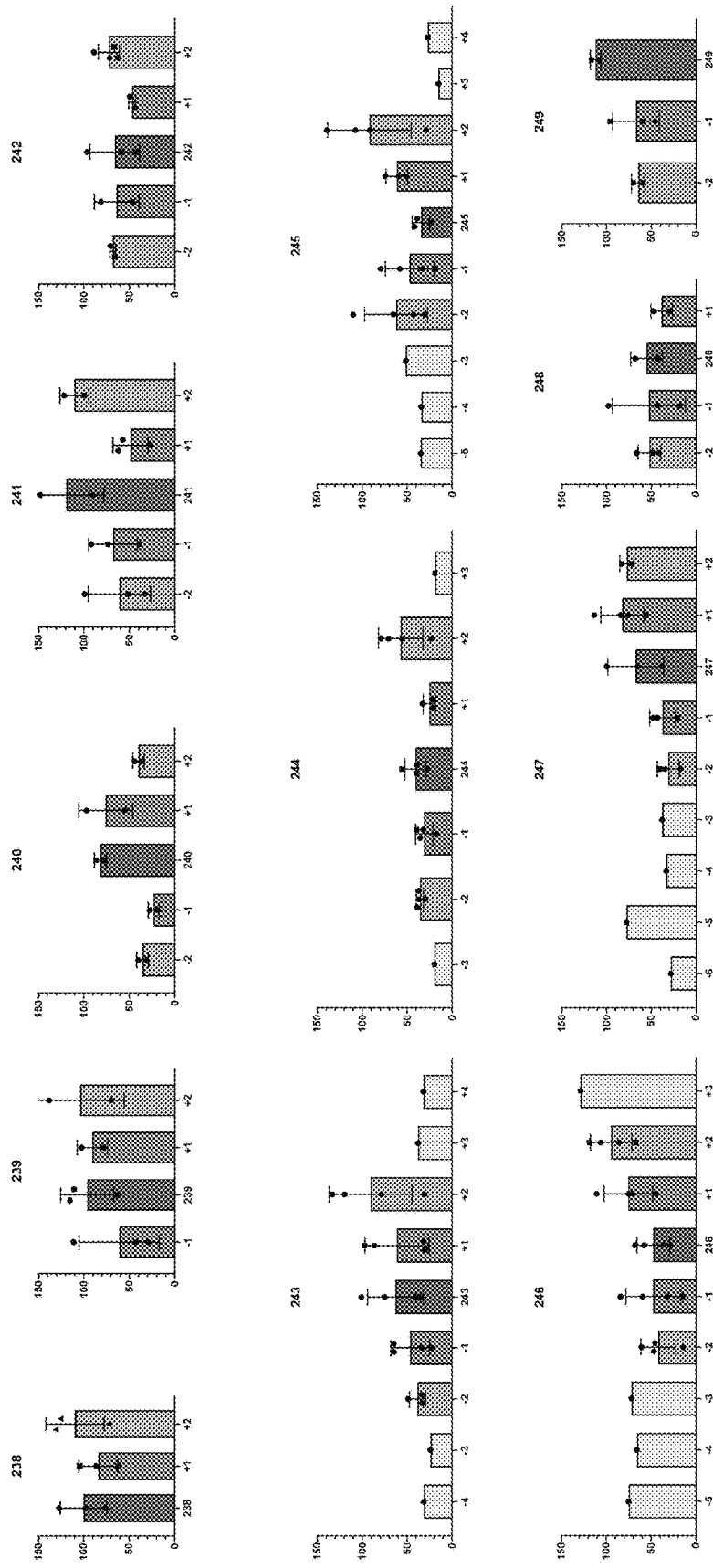
FIG. 30 is a graphical depiction of the results of a screen of overhang-containing dual-acting RNA silencing agents in an assay measuring C9orf72 sense transcript depletion. The dual-acting RNA silencing agents (1.5 µM) were tested using the psiCHECK2 system over 72 hours in HeLa cells.
Figure 31:
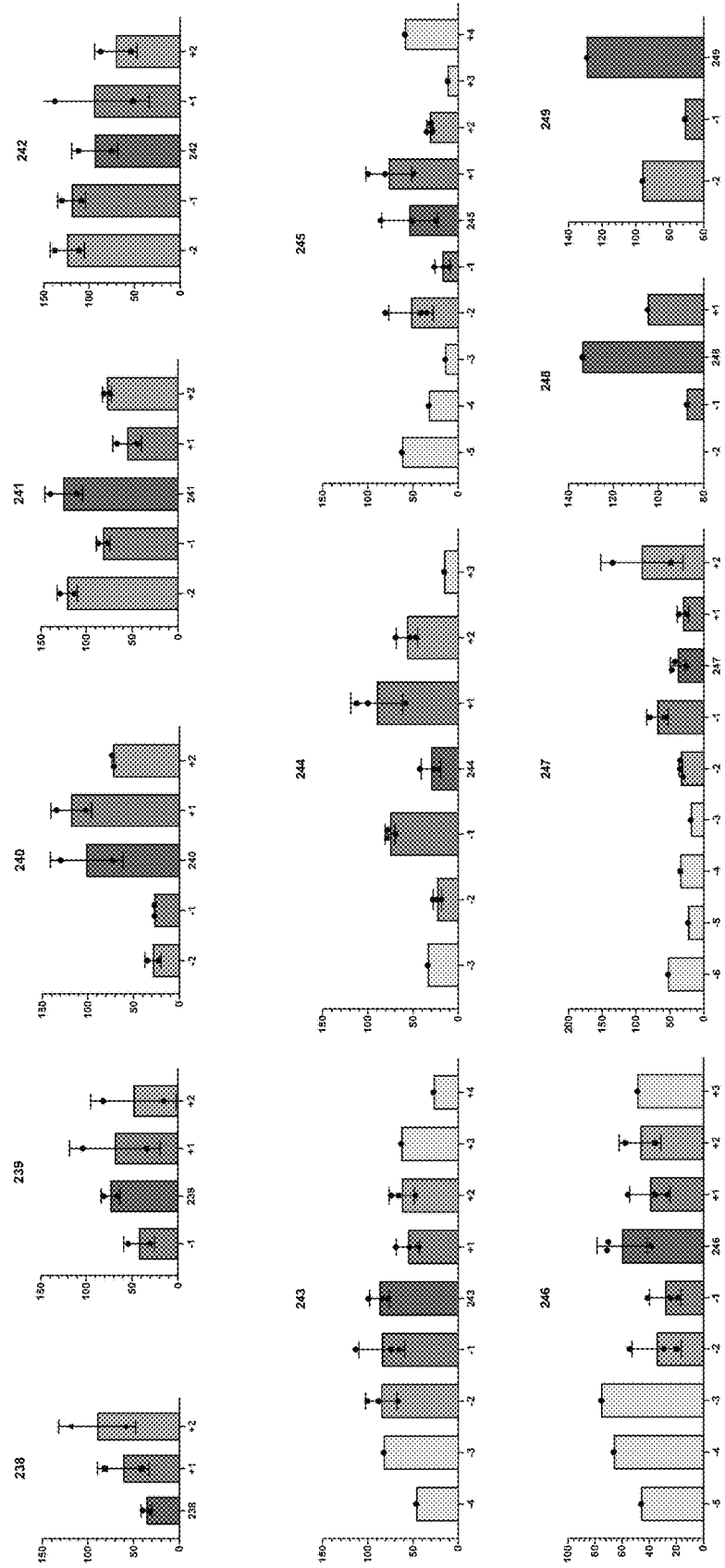
FIG. 31 is a graphical depiction of the results of a screen of overhang-containing dual-acting RNA silencing agents in an assay measuring C9orf72 antisense transcript depletion. The dual-acting RNA silencing agents (1.5 µM) were tested using the psiCHECK2 system over 72 hours in HeLa cells.

A similar experiment was performed with overhang-containing dual-acting RNA silencing agents. Exemplary formats are shown in FIG. 29. The overhang-containing dual-acting RNA silencing agents comprise overhangs for various lengths at the 5' end of the first guide strand and the second guide strand, or the 3' end of the first guide strand and the second guide strand. 5' end overhangs of 1 nucleotide (+1), 2 nucleotides (+2), 3 nucleotides (+3), and 4 nucleotides (+4) were employed. 3' end overhangs of 1 nucleotide (−1), 2 nucleotides (−2), 3 nucleotides (−3), 4 nucleotides (−4), 5 nucleotides (−5), and 6 nucleotides (−6) were employed as well. Robust knockdown was observed in targeting both sense (FIG. 30) and antisense (FIG. 31) strands. Moreover, several overhang-containing dual-acting RNA silencing agents exhibited greater silencing efficacy than the blunt-ended counterparts.

INCORPORATION BY REFERENCE

The contents of all cited references (including literature references, patents, patent applications, and websites) that can be cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;
Ausubel et al. (eds.), CURRENT PROTOCOLS IN MOLECULAR BIOLOGY, John Wiley & Sons, NY (1993);
Ausubel, F. M. et al. eds., SHORT PROTOCOLS IN MOLECULAR BIOLOGY (4th Ed. 1999) John Wiley & Sons, NY. (ISBN 0-471-32938-X);
CONTROLLED DRUG BIOAVAILABILITY, DRUG PRODUCT DESIGN AND PERFORMANCE, Smolen and Ball (eds.), Wiley, New York (1984);
Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, New York, (1999);
Goodson, in MEDICAL APPLICATIONS OF CONTROLLED RELEASE, vol. 2, pp. 115-138 (1984);
Hammerling, et al., in: MONOCLONAL ANTIBODIES AND T-CELL HYBRIDOMAS 563-681 (Elsevier, N.Y., 1981;
Harlow et al., ANTIBODIES: A LABORATORY MANUAL, (Cold Spring Harbor Laboratory Press, 2nd ed. 1988);
Kabat et al., SEQUENCES OF PROTEINS OF IMMUNOLOGICAL INTEREST (National Institutes of Health, Bethesda, Md. (1987) and (1991);
Kabat, E. A., et al. (1991) SEQUENCES OF PROTEINS OF IMMUNOLOGICAL INTEREST, Fifth Edition, U.S. Department of Health and Human Services, NIH Publication No. 91-3242;
Kontermann and Dubel eds., ANTIBODY ENGINEERING (2001) Springer-Verlag. New York. 790 pp. (ISBN 3-540-41354-5).
Kriegler, Gene Transfer and Expression, A Laboratory Manual, Stockton Press, NY (1990);
Lu and Weiner eds., CLONING AND EXPRESSION VECTORS FOR GENE FUNCTION ANALYSIS (2001) BioTechniques Press. Westborough, MA. 298 pp. (ISBN 1-881299-21-X).
MEDICAL APPLICATIONS OF CONTROLLED RELEASE, Langer and Wise (eds.), CRC Pres., Boca Raton, Fla. (1974);
Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).
O'Rourke, J. G. et al. C9ORF72 BAC TRANSGENIC MICE DISPLAY TYPICAL PATHOLOGIC FEATURES OF ALS/FTD, Neuron. 2015 Dec. 2; 88(5): 892-901.
Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).
SUSTAINED AND CONTROLLED RELEASE DRUG DELIVERY SYSTEMS, J. R. Robinson, ed., Marcel Dekker, Inc., New York, 1978
Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure can be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A double-acting RNA silencing agent comprising a first oligonucleotide strand and a second oligonucleotide strand, each strand comprising a 5' end and a 3' end, wherein the first strand inhibits expression of a C9ORF72 sense transcript and the second strand inhibits expression of a C9ORF72 antisense transcript, wherein the first and second oligonucleotide strand are substantially complementary to a non-repeat region in the C9ORF72 sense and antisense transcript, respectively;

wherein nucleotides at positions 2-6 and 14 from the 3' end of the second oligonucleotide strand are 2'-methoxy-ribonucleotides.

2. The double-acting RNA silencing agent of claim 1, wherein the first strand and the second strand comprise guide strands and wherein the first and second strands forma duplex of 15 to 30 nucleotides in length.

3. The double-acting RNA silencing agent of claim 1, further comprising a hydrophilic moiety or a hydrophobic moiety.

4. The double-acting RNA silencing agent of claim 1, wherein:

the first strand comprises a region of complementarity, which is substantially complementary to

```
                                                    (SEQ ID NO: 1)
5' ACAAGAAAAGACCUGAUAAAGAUUAACCAGAAGAAAACAAGGAGG
3',
                                                    (SEQ ID NO: 2)
5' AGAAAAGACCUGAUAAAGAUUAACCAGAAGAAAACAAGGAGGGAA
3', or
                                                    (SEQ ID NO: 4)
5' AAGAUUAACCAGAAGAAAAC 3',
``` the second strand comprises a region of complementarity, which is substantially complementary to

```
                                                    (SEQ ID NO: 3)
5' UCCCUCCUUGUUUUCUUCUGGUUAAUCUUUAUCAGGUCUUUUCUU
3' or
                                                    (SEQ ID NO: 5)
5' GUUUUCUUCUGGUUAAUCUA 3'.
```

5. A double-acting RNA silencing agent comprising a first oligonucleotide strand and a second oligonucleotide strand, each strand comprising a 5' end and a 3' end, wherein the first strand inhibits expression of a C9ORF72 sense transcript and the second strand inhibits expression of a C9ORF72 antisense transcript, wherein the first and second oligonucleotide strand are substantially complementary to a non-repeat region in the C9ORF72 sense and antisense transcript, wherein the second strand comprises a region of complementarity, which is substantially complementary to

```
                                                    (SEQ ID NO: 3)
5' UCCCUCCUUGUUUUCUUCUGGUUAAUCUUUAUCAGGUCUUUUCUU
3' or
                                                    (SEQ ID NO: 5)
5' GUUUUCUUCUGGUUAAUCUA 3'.
```

6. The double-acting RNA silencing agent of claim 1, wherein nucleotides at positions 2-4 from the 3' end of the first oligonucleotide strand are 2'-methoxy-ribonucleotides.

7. The double-acting RNA silencing agent of claim 2, wherein:

the first strand 5' end and the second strand 5' end each comprise a 1 nucleotide to 6 nucleotide single stranded nucleotide overhang, or the first strand 3' end and the second strand 3' end each comprise a 1 nucleotide to 6 nucleotide single stranded nucleotide overhang.

8. A pharmaceutical composition comprising the double-acting RNA silencing agent of claim 1 and a pharmaceutically acceptable carrier.

9. A branched oligonucleotide compound comprising at least two double-acting RNA silencing agents, wherein each double-acting RNA silencing agent comprises:

a first guide strand comprising a 5' end and a 3' end, and
a second guide strand comprising a 5' end and a 3' end,
wherein the at least two double-acting RNA silencing agents are connected to one another by one or more moieties comprising a linker, a spacer, or a branching point, wherein the first guide strand inhibits expression of a sense mRNA target and the second guide strand inhibits expression of an antisense mRNA target, and wherein nucleotides at positions 2-6 and 14 from the 3' end of the second guide strand are 2'-methoxy-ribonucleotides.

10. The branched oligonucleotide compound of claim 9, wherein each double-acting RNA silencing agent comprises a linker, a spacer, or a branching point, at the 3' end or at the 5' end of the first or second guide strand;

optionally wherein each second guide strand comprises the linker, spacer, or branching point at the 3' end; and optionally wherein each linker comprises an ethylene glycol chain, an alkyl chain, a peptide, an RNA, a DNA, a phosphate, a phosphonate, a phosphoramidate, an ester, an amide, a triazole, or a combination thereof, and wherein any carbon or oxygen atom of the linker is optionally replaced with a nitrogen atom, bears a hydroxyl substituent, or bears an oxo substituent.

11. The branched oligonucleotide compound of claim 9, further comprising a hydrophobic moiety or a hydrophilic moiety; and optionally wherein the hydrophobic moiety comprises an alkyl group, an alkenyl group, an aryl group, a vitamin, a vitamin derivative, cholesterol, a cholesterol derivative, a lipophilic amino acid, or a combination thereof.

12. The branched oligonucleotide compound of claim 9, wherein:
the first guide strand comprises a region of complementarity, which is substantially complementary to

```
                                              (SEQ ID NO: 1)
5' ACAAGAAAAGACCUGAUAAAGAUUAACCAGAAGAAAACAAGGAGG
3',
                                              (SEQ ID NO: 2)
5' AGAAAAGACCUGAUAAAGAUUAACCAGAAGAAAACAAGGAGGGAA
3', or
                                              (SEQ ID NO: 4)
5' AAGAUUAACCAGAAGAAAAC 3',
``` or
the second guide strand comprises a region of complementarity, which is substantially complementary to

```
                                              (SEQ ID NO: 3)
5' UCCCUCCUUGUUUUCUUCUGGUUAAUCUUUAUCAGGUCUUUUCUU
3' or
                                              (SEQ ID NO: 5)
5' GUUUUCUUCUGGUUAAUCUA 3'.
```

13. A branched oligonucleotide compound comprising at least two double-acting RNA silencing agents, wherein each double-acting RNA silencing agent comprises:
a first guide strand comprising a 5' end and a 3' end, and
a second guide strand comprising a 5' end and a 3' end, wherein the at least two double-acting RNA silencing agents are connected to one another by one or more moieties comprising a linker, a spacer, or a branching point, and
wherein the second guide strand comprises a region of complementarity, which is substantially complementary to

```
                                              (SEQ ID NO: 3)
5' UCCCUCCUUGUUUUCUUCUGGUUAAUCUUUAUCAGGUCUUUUCUU
3' or
                                              (SEQ ID NO: 5)
5' GUUUUCUUCUGGUUAAUCUA 3'.
```

14. The branched oligonucleotide compound of claim 9, wherein at least one of the at least two double-acting RNA silencing agents comprises a modified nucleotide comprising a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

15. The branched oligonucleotide compound of claim 9, wherein the first guide strand is substantially complementary to the second guide strand and wherein nucleotides at positions 2-4 from the 3' end of the first oligonucleotide strand are 2'-methoxy-ribonucleotides; and
optionally wherein at least one nucleotide is mismatched between the first guide strand 5' end and the second guide strand 3' end, and at least one nucleotide is mismatched between the first strand 3' end and the second strand 5' end; or
optionally wherein at least one dual-acting RNA silencing agent comprises at least one single stranded nucleotide overhang.

16. The branched oligonucleotide compound of claim 15, wherein:
the first guide strand 5' end and the second guide strand 5' end each comprise a 1 nucleotide to 6 nucleotide single stranded nucleotide overhang, or
the first guide strand 3' end and the second guide strand 3' end each comprise a 1 nucleotide to 6 nucleotide single stranded nucleotide overhang.

17. A pharmaceutical composition comprising the branched oligonucleotide compound of claim 9 and a pharmaceutically acceptable carrier.

18. A double-acting, double stranded (ds) RNA comprising a first guide strand and a second guide strand, each strand comprising a 5' end and a 3' end, wherein at least one nucleotide is mismatched between the first strand 5' end and the second strand 3' end, and at least one nucleotide is mismatched between the first strand 3' end and the second strand 5' end, wherein the first guide strand inhibits expression of a sense mRNA target and the second guide strand inhibits expression of an antisense mRNA target,
wherein nucleotides at positions 2-6 and 14 from the 3' end of the second guide strand are 2'-methoxy-ribonucleotides.

19. The double-acting dsRNA of claim 18, wherein the first guide strand 5' end and the second guide strand 3' end comprise three nucleotide mismatches and the first guide strand 3' end and the second guide strand 5' end comprise three nucleotide mismatches; and optionally wherein the dsRNA comprises at least one single stranded nucleotide overhang.

20. The double-acting dsRNA of claim 18, wherein the double-acting dsRNA comprises a modified nucleotide comprising a nucleotide comprising a 5'-phosphorothioate group, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, or a non-natural base comprising nucleotide.

21. The double-acting dsRNA of claim 18, wherein:
the first guide strand comprises a region of complementarity, which is substantially complementary to

```
                                              (SEQ ID NO: 1)
5' ACAAGAAAAGACCUGAUAAAGAUUAACCAGAAGAAAACAAGGAGG
3', or
                                              (SEQ ID NO: 4)
5' AAGAUUAACCAGAAGAAAAC 3',
``` or
the second guide strand comprises a region of complementarity, which is substantially complementary to

```
                                                     (SEQ ID NO: 3)
5' UCCCUCCUUGUUUUCUUCUGGUUAAUCUUUAUCAGGUCUUUUCUU
3' or (SEQ ID NO: 5)
5' GUUUUCUUCUGGUUAAUCUA 3'.
```

22. A double-acting, double stranded (ds) RNA comprising a first guide strand and a second guide strand, each strand comprising a 5' end and a 3' end, wherein at least one nucleotide is mismatched between the first strand 5' end and the second strand 3' end, and at least one nucleotide is mismatched between the first strand 3' end and second strand 5' end, wherein the first guide strand inhibits expression of a sense mRNA target and the second guide strand inhibits expression of an antisense mRNA target, wherein the second guide strand comprises a region of complementarity, which is substantially complementary to

```
                                                     (SEQ ID NO: 3)
5' UCCCUCCUUGUUUUCUUCUGGUUAAUCUUUAUCAGGUCUUUUCUU
3' or (SEQ ID NO: 5)
5' GUUUUCUUCUGGUUAAUCUA 3'.
```

23. The double-acting dsRNA of claim 18, wherein the first guide strand is substantially complementary to the second guide strand; and optionally wherein at least one nucleotide is mismatched between the first guide strand 5' end and the second guide strand 3' end, and at least one nucleotide is mismatched between the first guide strand 3' end and the second guide strand 5' end.

24. The double-acting dsRNA of claim 18, wherein:
the first strand 5' end and the second strand 5' end each comprise a 1 nucleotide to 6 nucleotide single stranded nucleotide overhang, or
the first strand 3' end and the second strand 3' end each comprise a 1 nucleotide to 6 nucleotide single stranded nucleotide overhang.

25. The double-acting dsRNA of claim 18, wherein at least one of the sense mRNA target and the antisense mRNA target comprises a disease-associated nucleotide sequence.

26. A pharmaceutical composition comprising the double-acting dsRNA of claim 18 and a pharmaceutically acceptable carrier.

27. The double-acting RNA silencing agent of claim 2, wherein the first strand and the second strand independently each comprise at least 16, at least 17, at least 18, at least 19, or at least 20 contiguous nucleotides and the strands are fully complementary.

28. The double-acting RNA silencing agent of claim 3, wherein the hydrophobic moiety comprises an alkyl group, an alkenyl group, an aryl group, a vitamin, a vitamin derivative, cholesterol, a cholesterol derivative, a lipophilic amino acid, or combinations thereof.

29. The double-acting RNA silencing agent of claim 6, wherein the first oligonucleotide strand and the second oligonucleotide strand are fully modified.

30. The double-acting RNA silencing agent of claim 6, wherein the first oligonucleotide strand is substantially complementary to the second oligonucleotide strand.

31. The double-acting RNA silencing agent of claim 6, wherein at least one nucleotide is mismatched between the first strand 5' end and the second strand 3' end, and at least one nucleotide is mismatched between the first strand 3' end and the second strand 5' end.

32. The double-acting RNA silencing agent of claim 30 further comprising at least one single stranded nucleotide overhang.

* * * * *